(12) United States Patent
Letourneau et al.

(10) Patent No.: US 10,016,315 B2
(45) Date of Patent: Jul. 10, 2018

(54) WEARABLE APPARATUS FOR DETECTING A TARGET SUBSTANCE IN A LIQUID

(71) Applicant: Undercover Colors, Inc., Raleigh, NC (US)

(72) Inventors: Nicolas Letourneau, Raleigh, NC (US); Aly Khalifa, Raleigh, NC (US); Michael Gorczynski, Raleigh, NC (US); Catherina Gomes, Raleigh, NC (US); Ronald Smith, Raleigh, NC (US); Sarah Paluskiewicz, Raleigh, NC (US); Stephen Gray, Raleigh, NC (US); Tyler Confrey-Maloney, Raleigh, NC (US)

(73) Assignee: Undercover Colors, Inc., Raleigh, NC (US)

( * ) Notice: Subject to any disclaimer, the term of this patent is extended or adjusted under 35 U.S.C. 154(b) by 0 days.

(21) Appl. No.: 15/449,721

(22) Filed: Mar. 3, 2017

(65) Prior Publication Data
US 2017/0209313 A1    Jul. 27, 2017

Related U.S. Application Data

(63) Continuation of application No. 15/508,178, filed as application No. PCT/US2017/015504 on Jan. 27, 2017.
(Continued)

(51) Int. Cl.
*G01N 33/14* (2006.01)
*G01N 33/02* (2006.01)
(Continued)

(52) U.S. Cl.
CPC ........ *A61F 13/42* (2013.01); *A61F 13/00055* (2013.01); *A61F 13/15* (2013.01);
(Continued)

(58) Field of Classification Search
CPC .... A61F 13/42; A61F 13/00055; A61F 13/15; A61F 13/84; G01N 33/52; G01N 33/53
See application file for complete search history.

(56) References Cited

U.S. PATENT DOCUMENTS 4,826,759 A * 5/1989 Guire .................... B01L 3/5055
                                                           422/412
4,943,522 A * 7/1990 Eisinger .......... G01N 33/54386
                                                           422/537
(Continued)

FOREIGN PATENT DOCUMENTS

EP         0315040 B1     1/1993
WO         2014184151     11/2014
(Continued)

OTHER PUBLICATIONS

PCT/US2017/015489 , "International Search Report and Written Opinion", dated Apr. 12, 2017, 11 pages.
(Continued)

*Primary Examiner* — Robert Eom
(74) *Attorney, Agent, or Firm* — Kilpatrick Townsend & Stockton LLP

(57) ABSTRACT

Described herein are a wearable apparatus and methods for detecting the presence of a targeted substance in a liquid. For example, the wearable apparatus can be a fingernail that detects illicit drugs in a beverage. The wearable apparatus comprises a detection layer comprising an indicator that is configured to display a signal upon the detection of an interaction with the targeted substance. In some examples, the wearable apparatus can include a lateral flow assay.

17 Claims, 32 Drawing Sheets

Related U.S. Application Data

(60) Provisional application No. 62/287,623, filed on Jan. 27, 2016, provisional application No. 62/287,643, filed on Jan. 27, 2016, provisional application No. 62/287,677, filed on Jan. 27, 2016, provisional application No. 62/337,558, filed on May 17, 2016, provisional application No. 62/337,603, filed on May 17, 2016, provisional application No. 62/337,608, filed on May 17, 2016.

(51) Int. Cl.
| A61F 13/42 | (2006.01) |
| A61F 13/15 | (2006.01) |
| G01N 33/52 | (2006.01) |
| G01N 33/53 | (2006.01) |
| A61F 13/84 | (2006.01) |
| A61F 13/00 | (2006.01) |

(52) U.S. Cl.
CPC ............ *A61F 13/84* (2013.01); *G01N 33/52* (2013.01); *G01N 33/53* (2013.01); *A61F 2013/422* (2013.01); *A61F 2013/429* (2013.01); *A61F 2013/8473* (2013.01)

(56) References Cited

U.S. PATENT DOCUMENTS

| | | | |
|---|---|---|---|
| 5,267,566 | A | 12/1993 | Choucair et al. |
| 6,022,433 | A | 2/2000 | Higuchi et al. |
| 6,365,417 | B1* | 4/2002 | Fleming ............... G01N 33/558 422/412 |
| 6,528,323 | B1 | 3/2003 | Thayer et al. |
| 6,551,842 | B1 | 4/2003 | Carpenter |
| 7,148,879 | B2 | 12/2006 | Amento et al. |
| 7,238,533 | B1 | 7/2007 | Legge et al. |
| 7,749,775 | B2 | 7/2010 | Maher et al. |
| 8,003,407 | B2 | 8/2011 | Zhou et al. |
| 8,179,604 | B1 | 5/2012 | Prada Gomez et al. |
| 8,834,946 | B2 | 9/2014 | Abramson et al. |
| 8,895,293 | B2 | 11/2014 | Kanaley et al. |
| 8,920,857 | B2 | 12/2014 | Abramson et al. |
| 9,285,352 | B2 | 3/2016 | Abramson et al. |
| 9,528,973 | B2 | 12/2016 | Abramson et al. |
| 2002/0182600 | A1 | 12/2002 | Smith et al. |
| 2005/0043894 | A1 | 2/2005 | Fernandez |
| 2005/0079629 | A1 | 4/2005 | Guo et al. |
| 2006/0019406 | A1 | 1/2006 | Wei et al. |
| 2006/0134611 | A1 | 6/2006 | Danzy et al. |
| 2007/0092977 | A1 | 4/2007 | Reich |
| 2008/0257361 | A1 | 10/2008 | Hakim et al. |
| 2009/0096746 | A1 | 4/2009 | Kruse |
| 2009/0157024 | A1 | 6/2009 | Song |
| 2009/0263854 | A1* | 10/2009 | Jacono ............... G01N 33/558 435/29 |
| 2012/0160725 | A1 | 6/2012 | Abramson et al. |
| 2013/0209325 | A1 | 8/2013 | Haroon |
| 2014/0212960 | A1* | 7/2014 | Abe .................... G01N 33/523 435/288.7 |
| 2014/0228234 | A1 | 8/2014 | Zak et al. |
| 2014/0246037 | A1 | 9/2014 | Drake |
| 2015/0025347 | A1 | 1/2015 | Song |
| 2015/0064800 | A1 | 3/2015 | Chance et al. |
| 2015/0356669 | A1 | 12/2015 | Roescheisen et al. |
| 2016/0025752 | A1 | 1/2016 | Santiago et al. |
| 2016/0146773 | A1 | 5/2016 | Abramson et al. |
| 2017/0059542 | A1 | 3/2017 | Abramson et al. |
| 2017/0160253 | A1 | 6/2017 | Abramson et al. |

FOREIGN PATENT DOCUMENTS

| | | | |
|---|---|---|---|
| WO | WO2014184151 | A1 * | 11/2014 ............... B01L 3/00 |
| WO | 2015066459 | | 5/2015 |
| WO | 2017132604 | | 8/2017 |
| WO | 2017132614 | | 8/2017 |
| WO | 2017132618 | | 8/2017 |

OTHER PUBLICATIONS

PCT/US2017/015500, "International Search Report and Written Opinion", dated Apr. 7, 2017, 9 pages.
PCT/US2017/015504, "International Search Report and Written Opinion", dated Apr. 5, 2017, 9 pages.
Andreou, C., "Microfluidics device detects drugs in saliva fast," 2013, http://www.nanowerk.com/spotlight/spotid=31524.php.
Arce, N., "Meet NailO: MIT's Wearable Device That Turns Fingernail Into Trackpad," 2015, http://www.techtimes.com/articles/47120/20150418/meet-nailo-mits-wearable-device-that-turns-fingernail-into-trackpad.
Bottoms, J., et al., "The Development of Paper Microfluidic Devices for the Presumptive Determination of Seized Drugs," Criminalistics Section, 2015.
Chong, H., et al., "Paper-based Microfluidic Point-of-care Diagnostic Devices for Monitoring Drug Metabolism," J. Biotherapeut Discov, Apr. 25, 2013, https://www.omicsonline.org/paper-based-microfluidic-point-of-care-diagnostic-devices-for-monitoring-drug-metabolism.
Dume, B., "Sweatband measures tiny electrical signals in perspiration," Feb. 2, 2016, http://physicsworld.com/cws/article/news/2016/feb/02/sweatband-measures-tiny-electrical-signals-in-persipration.
Dume, B., "Tiny sweat sensor goes wireless," Feb. 1, 2016, http://nanotechweb.com/cws/article/tech/63855.
"Fingertip," Digital Trends, http://www.digitaltrends.com/cool-tech/the_next_step_to_our_cyborg_future?_fierce_fabulous_smart_nails.
Govers III, F, "InTouch tech allows files to be transferred between devices with a touch," 2013, http://newatlas.com/intouch-ring-data-transfer/29486/.
Lopatto, E., "Nail Polish Is the Next Wearable Tech," 2014, http://www.thedailybeast.com/articles/2014/06/04/nail-polish-is-the-next-wearable-tech.
Masterson, A., "In the world of wearable technology, Melbourne nails Shanghai," 2015, http://www.smh.com.au/digital-life/wearables/in-the-world-of-wearable-technology-melbourne-nails-shanghai.
Meinhold, B., "Nail Salons of the Future Offer Wearable-Tech Manicures," 2014 http://www.ecouterre.com/nail_salons_of_the_future_offer_wearable-tech_manicures.
Musile, G., et al., "The development of paper microfluidic devices for presumptive drug detection,"Anal. Methods, 2015, https://www.researchgate.net/publications/294891450_The_development_of_paper_microfluidic_devices_for_presumptive_drug_detection.
O'Callaghan, J., "Wearable technology Nailed: Smart fingernails light up when you take a call," 2014 http://www.dailymail.co.uk/sciencetech/article-2676522/wearable_technology_nailed:_smart_fingernails_light_up_when_you_take_a_call.
Starr, Michelle, "Fingernail-shaped stylus is manicure-friendly," 2014, https://www.cnet.com/news/fingernail-shaped-stylus-is-manicure-friendly/.
Wang, J., "Tiny Lab Devices Could Attack Huge Problem of Drug-Resistant Infections," Apr. 23, 2015, http://releases.jhu.edu/2015/04/23/tiny-lab-devices-could-attack-huge-problem-of-drug-resistant-infections.
"Diafactory Tinea Unguium", Dermatophyte Test Strip, Mar. 8, 2017.
"gRAD One Detection Kit", Bioporto Diagnostics, Nov. 2015.
"PartoSure Assess the Risk of Preterm Birth", 2015.
U.S. Appl. No. 15/606,119, "Restriction Requirement", dated Jun. 28, 2017, 8 pages.
U.S. Appl. No. 15/606,119, "Non Final Office Action", dated Sep. 12, 2017, 10 pages.
U.S. Appl. No. 15/606,119, "Final Office Action", dated Mar. 22, 2018, 15 pages.
PCT/US2017/015489, "International Preliminary Report on Patentability", dated Mar. 12, 2018, 7 pages.

(56) References Cited

OTHER PUBLICATIONS

PCT/US2017/015504, "Written Opinion", dated Feb. 12, 2018, 6 pages.

* cited by examiner

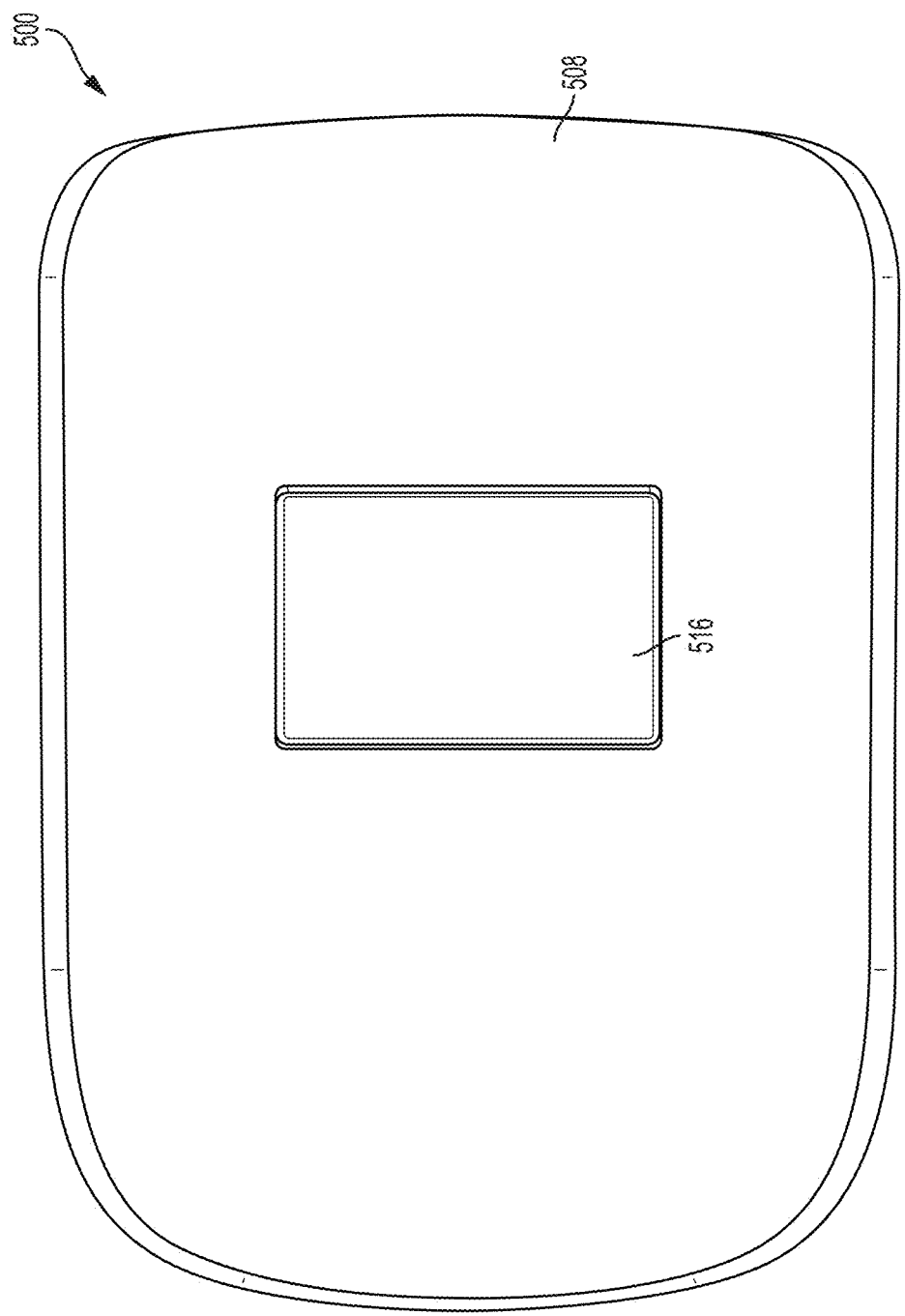

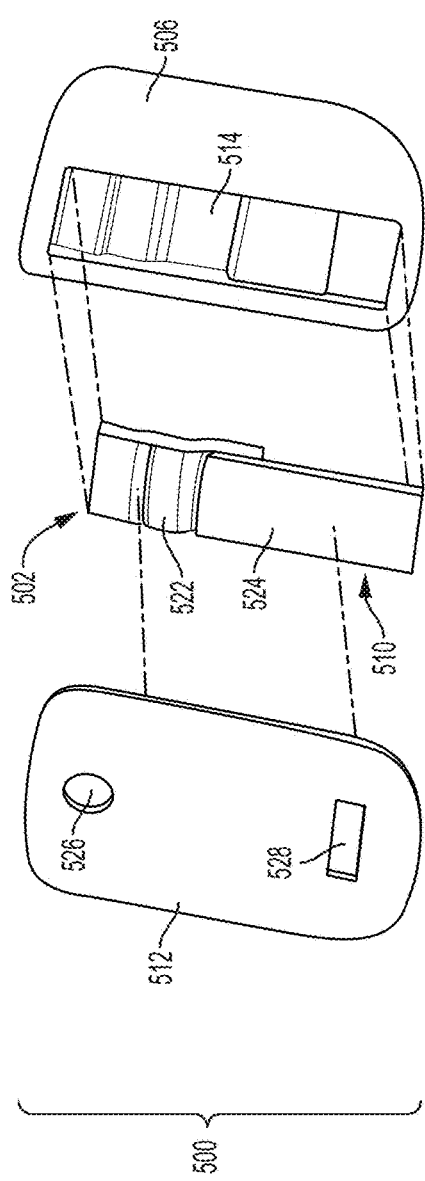
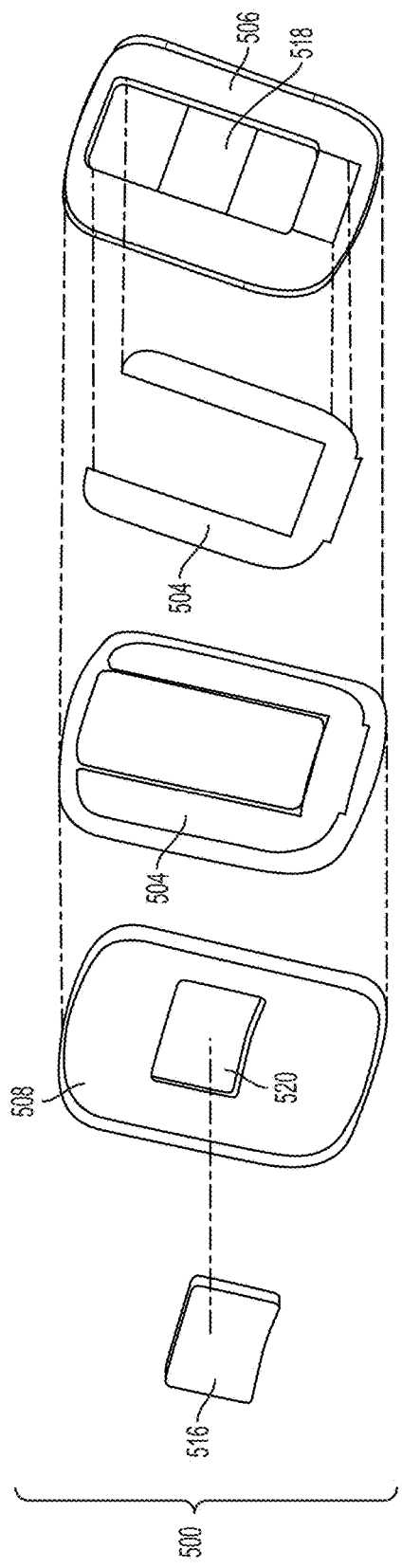

WEARABLE APPARATUS FOR DETECTING A TARGET SUBSTANCE IN A LIQUID

CROSS-REFERENCES TO RELATED APPLICATIONS

This application claims priority to U.S. patent application Ser. No. 15/508,178, which is the U.S. national phase of International Application No. PCT/US2017/15504 filed on Jan. 27, 2017, which application claims priority to U.S. Provisional Application No. 62/287,677 filed on Jan. 27, 2016; U.S. Provisional Application No. 62/287,623, filed on Jan. 27, 2016; U.S. Provisional Application No. 62/287,643, filed on Jan. 27, 2016; U.S. Provisional Application No. 62/337,603, filed on May 17, 2016; U.S. Provisional Application 62/337,558, filed on May 17, 2016; and U.S. Provisional Application 62/337,608, filed on May 17, 2016, each of which is incorporated herein by reference in its entirety.

FIELD

Described herein are apparatus and methods for detecting a target substance. For example, the apparatus and methods described herein can be used for real-time detection of illicit drugs, different compounds in liquids, and/or different compounds in solids.

BACKGROUND

The demand and need for persons to be able detect different substances on a real-time basis has increased as the prevalence of auto-immune disorders and different allergies diagnoses have increased. This increase has also corresponded with an increased frequency of drug use and abuse. In view of these trends, conventional testing methods and devices often are too cumbersome or take too long to evaluate a particular medium for a target substance. In some cases, no specific apparatus for real-time detection for certain target substances or compounds exist.

For example, an increased misuse of various psychotropic and/or sedating drugs for recreational or criminal purposes has become more problematic. A particularly troubling form of misuse is the surreptitious introduction of these drugs into ordinary drinks for the purpose of rendering the consumer of the drink disoriented or unconscious. The unknowingly sedated individual may then be taken advantage of, e.g., become the victim of robbery or sexual assault. Drug-facilitated sexual assault has become increasingly common, particularly among younger members of the population, to the degree that most universities have warning and prevention programs and policies in place to prevent drug-facilitated sexual assault. Conventional apparatus to detect such drugs prior to ingestion often are insufficient as they may be too cumbersome to use, take too long to detect the target substance, detect only a limited substance, and lack selectivity and/or are sensitive to many other non-drug compounds.

As another example, an increased frequency of diagnoses of auto-immune disorders or highly sensitive allergies has occurred in the general population. For example, Celiac's disease, peanut allergies, lactose allergies or other conditions triggered by different ingested substances have become more common in the general population. If the particular harmful substance is ingested by persons having these types of conditions occurs, significant and severe consequences for the person may result.

Viable methods, systems, and apparatus for the safe, real-time detection of targeted substances are needed.

SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

Various embodiments of the present invention relate to a wearable apparatus and methods for making a wearable apparatus for detecting a targeted substance in a liquid. For example, the wearable apparatus and methods described herein can be used for real-time detection of illicit drugs. In some embodiments, a wearable apparatus for detecting the presence of a targeted substance comprises a detection layer that includes an indicator that may be configured to display a signal upon the detection of an interaction with the targeted substance, a top layer coupled to a top surface of the detection layer, and a bottom layer coupled to a bottom surface of the detection layer.

In some embodiments, an apparatus for detecting the presence of a targeted compound in a liquid further comprises an adhesive layer coupled to a bottom surface of the bottom layer. In some embodiments, the apparatus further comprises a removable layer coupled to a top surface of the detection layer. In some such embodiments, the removable layer may be configured such that upon removing of the removable layer, at least a portion of the detection layer may be exposed to an external environment.

In some embodiments, the detection layer comprises a chromatographic membrane pad and a sample pad. In some embodiments, the detection layer further comprises a conjugate pad. In some embodiments, the detection layer further comprises an absorbent pad. In some embodiments, the absorbent pad may substantially U-shaped. In some embodiments, the absorbent pad is substantially parallel to the chromatographic membrane pad. In some embodiments, the detection layer may be configured to minimize, significantly reduce, or substantially eliminate migration of an assay component into the liquid being tested. In some embodiments, the detection layer comprises a lateral flow assay.

In some embodiments, the wearable apparatus may be positioned on a human body. In some embodiments, the apparatus may be positioned on a fingernail, and in some cases, by an adhesive. In some embodiments, the apparatus may be position on or within objects, such as a ring, bracelet, charm, lanyard, or necklace.

In other embodiments, a method of detecting the presence of a targeted substance in a liquid is described herein. In some embodiments, the method comprises providing the wearable apparatus, exposing a portion of the wearable apparatus to the liquid, and observing a visual indication to determine presence or absence of the targeted substance.

In other embodiments, a method of making a wearable apparatus is described herein. In some embodiments, the method of making an apparatus comprises providing a detection layer configured to detect the presence of a targeted substance; coupling a top layer to a top surface of the detection layer; and coupling a bottom layer to a bottom surface of the detection. In some embodiments, the method of making also includes coupling a removable layer to the top layer.

The details of one or more embodiments are set forth in the drawings and description below. Other features, objects, and advantages will be apparent from the drawings, the description, and from the claims.

BRIEF DESCRIPTION OF DRAWINGS

FIG. 10 shows a bottom view of an apparatus according to one embodiment of the present invention.

FIGS. 11A and 11B show exploded views of an apparatus according to one embodiment of the present invention. FIG. 11A shows a top perspective, and FIG. 11B shows a bottom perspective.

FIG. 12 shows a an exploded view of a top layer and a bottom layer of an apparatus according to one embodiment of the present invention.

FIG. 13A shows a top, perspective view, FIG. 13B shows a side view, FIG. 13C shows a top view, and FIG. 13D shows a front view.

FIG. 14A shows a bottom, perspective view, and FIG. 14B shows a bottom view.

FIG. 15A shows a top, perspective view, FIG. 15B shows a side view, FIG. 15C shows a top view and FIG. 15D shows a front view.

FIG. 16A shows a top, perspective view, FIG. 16B shows a top view, and FIG. 16C shows a cross-sectional view along the line B-B in FIG. 16B.

FIG. 18A shows a side view, FIG. 18B shows a cross-sectional view along the line A-A of FIG. 18A, and FIG. 18C shows a front view.

FIG. 23A shows a top, perspective view and FIG. 23B shows a bottom, perspective view.

FIG. 24A shows a top, perspective view and FIG. 24B shows a bottom, perspective view.

DETAILED DESCRIPTION

Figure 1:
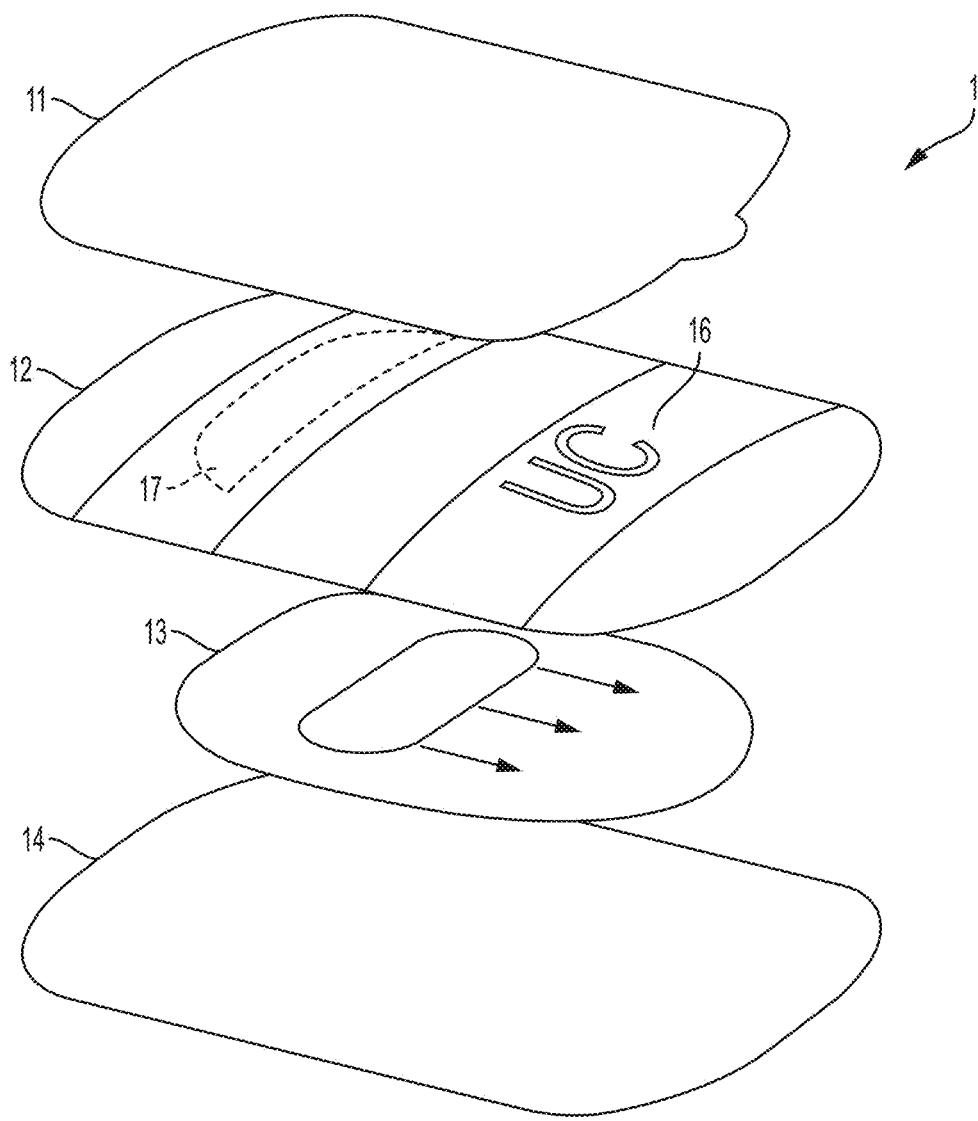
FIG. 1 shows an exploded view of an apparatus according to one embodiment of the present invention.

The subject matter of embodiments of the present invention is described herein with specificity to meet statutory requirements, but this description is not necessarily intended to limit the scope of future claims. The subject matter to be claimed may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described. The illustrative examples are given to introduce the reader to the general subject matter discussed herein and not intended to limit the scope of the disclosed concepts. The following sections describe various additional embodiments and examples with reference to the drawings in which like numerals indicate like elements and directional description are used to describe illustrative embodiments but, like the illustrative embodiments, should not be used to limit the present invention.

Unless indicated to the contrary, the numerical parameters set forth in the following specification are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10.

Described herein are methods and a wearable apparatus for detecting a target substance. In some embodiments, the methods and apparatus can detect a targeted compound in a liquid. In some embodiments, the methods and apparatus can detect a target substance in a solid. For example, the methods and apparatus described herein can be used for real-time detection of illicit drugs, e.g., amine-containing compounds or drugs, benzodiazepines, amine-containing compounds or drugs, analytes, abused narcotics, alcohol, drugs, date rape drugs, or other target compounds or analytes. As another example, the methods and apparatus described herein can be used for real-time detection of certain proteins, sugars, or allergens, e.g., gluten, peanut proteins, or lactose. In some embodiments, the methods and apparatus described herein can be used for real-time detection of other materials, for example, pesticides, steroids and their metabolites, bacteria, pathogens, fungi, poisons, toxins, chemical warfare agents, environmental poisons, explosives and the starting materials used to make them, as well as mixtures of small molecules, metals, volatile organics, and other targeted compounds.

In some embodiments, the methods and apparatus described herein can used for real-time detection of targeted substances, analytes, or compounds within ketamine, 4-hydroxybutanoic acid (GHB), ephedrine, methamphetamine, amphetamine, flunitrazepam, 3,4-methylenedioxy-methamphetamine (MDMA), also known as ecstasy or molly, tetrahydrocannabinol (THC), and benzodiazepines such as clonazepam and others, and many more. In some embodiments, the methods and apparatus described herein can used for real-time detection of targeted substances, analytes, or compounds within foods or liquids.

In some examples, the liquid comprises a consumable liquid. For example, the consumable liquid can be include beer, cider, energy drinks, flavored drinks, fruit drinks, liquor or other alcoholic beverages, milk, milk-containing beverages, soda, sports drinks, vegetable drinks, water, wine, and combinations thereof. In some examples, the liquid comprises a non-consumable liquid (e.g., blood, non-potable water, organic solvents, potable water, serum, treated waste water, untreated waste water, urine, vomit, sweat, tears, reproductive fluids, other bodily secretions, or combinations thereof). The liquid can comprise a solution, a suspension, or an emulsion. In some examples, the liquid can contain solid particles or ice suspended therein. In some examples, the liquid medium can include liquid extract from a solid. In other cases, the methods and apparatuses can be used to detect analytes in a solid material, such as extracting gluten from bread. In some examples, the methods and apparatuses can be used to detect analytes in nutritional supplements, cosmetics, or soil. In further examples, the methods and apparatuses can be used to detect the presence of heavy metals.

In some examples, the wearable apparatus may be positioned on the surface of an object. In some examples, the apparatus can be positioned, integrated, or incorporated in an object. In other examples, the apparatus can be positioned below the surface of an object. In some examples, the wearable apparatus may be positioned on a human body. Wearable as described herein includes placement on a body or a part of a body as decoration, protection, or for some other purpose. Placement may be in direct contact with the body or indirect contract with the body. Some examples of items worn include, but are not limited to a synthetic fingernails, fingernail decals, rings, bracelets, charms, necklaces, and lanyards.

In some embodiments, the apparatus is positioned on the body with adhesive. The adhesive may be coupled with the bottom surface of the bottom layer to adhere the apparatus to the desired surface. Suitable objects include, for example, a fingernail, an artificial fingernail, a layer of fingernail polish, a fingernail sticker, a fingernail decal, a sticker, a decal, a nail wrap, a mesh nail wrap, a ring, a bracelet, a necklace, a charm, a lanyard, or any other appropriate surface or structure. In some embodiments, the apparatus can have a degree of flexibility to conform to the intended application of the apparatus. In some embodiments, the bottom layer may be flexible to conform to the intended application. In some embodiments, the detection layer may be flexible to conform to the intended application. For example, when the apparatus may be positioned on an arcuate structure (e.g., a fingernail), the apparatus can be flexed and positioned on the arcuate surface of a fingernail.

In some embodiments, the apparatus comprises a thickness ranging from about 0.1 millimeters (mm) to about 10 mm. In some embodiments, the apparatus comprises a thickness ranging from about 1 mm to about 5 mm. In some embodiments, the apparatus can have a thickness of about 0.4 mm or less, 0.5 or less, 1 mm or less, 2 mm or less, 3 mm or less, 4 mm or less, 5 mm or less, 6 mm or less, 7 mm or less, 8 mm or less, 9 mm or less, or 10 mm or less.

In some embodiments, the apparatus can have a length of about 10 mm to about 25 mm, or from about 10 mm to about 20 mm. In some embodiments, the apparatus can have a length of about 10 mm or less, 11 or less, 12 mm or less, 13 mm or less, 14 mm or less, 15 mm or less, 16 mm or less, 17 mm or less, 18 mm or less, 19 mm or less, 20 mm or less, 21 mm or less, 22 mm or less, 23 mm or less, 24 mm or less, 25 mm or less, 26 mm or less, 27 mm or less, 28 mm or less, 29 mm or less, or 30 mm or less.

In some embodiments, the apparatus comprises up to about a width of about 17 mm, for example, a width of about 16 mm, about 15.5 mm, about 15 mm, about 14.5 mm, about 14 mm, about 13.5 mm, or about 13 mm. In some examples, the apparatus may have a width of about 17 mm to about 13 mm. In some embodiments, the apparatus comprises up to about a width of about 4 mm, for example, a width of about 3.8 mm, about 3.6 mm, about 3.4 mm, about 3.2 mm, about 3 mm, about 2.8 mm, or about 2.6 mm. In some embodiments, the apparatus can have a width of about 10 mm or less, 11 or less, 12 mm or less, 13 mm or less, 14 mm or less, 15 mm or less, 16 mm or less, 17 mm or less, 18 mm or less, 19 mm or less, 20 mm or less, 21 mm or less, 22 mm or less, 23 mm or less, 24 mm or less, 25 mm or less, 26 mm or less, 27 mm or less, 28 mm or less, 29 mm or less, or 30 mm or less.

Some embodiments of the apparatus described herein can have a length of less than about 25 mm, a width of about 15 mm, and a thickness of about 5 mm. In some embodiments, the apparatus described herein can have a length of less than about 20 mm, a width of about 10 mm, and a thickness of about 2.5 mm.

In some embodiments, the apparatus can be laminated to provide protection from external environment without compromising the integrity of the test by permitting gas permeability during use. In some embodiments, the apparatus can be waterproof, or substantially waterproof, until the apparatus is activated, for example, upon the removal of a removable layer or other methods.

Certain embodiments described herein provide an apparatus for detecting the presence of a compound in a liquid, where the apparatus comprises a detection layer. In some embodiments, the detection layer can detect the presence of a target substance upon being exposed to a particular medium. In some embodiments, the detection layer can detect the presence of target substance or particular compound upon receiving a liquid to be tested for the target substance or particular compounds. For example, the detection layer can be exposed to the liquid in question and then monitored by a user to determine whether there is a particular interaction between the detection layer and the liquid to indicate the presence of the target substance. In some embodiments, the target substance may be an amine-containing compound or a benzodiazepine. In some embodiments, the target substance may be a protein or sugar.

In some embodiments, the detection layer can comprise at least one of a matrix that includes a marker, a lateral flow assay, a nanofluidic device, microfluidic devices, electrochemical sensors, or a membrane. In some embodiments the detection layer can operate by relying on the wicking or drawing of a liquid through the detection layer by capillary action. In some embodiments, the detection layer can operate based on a series of capillary sections that transport fluids through a plurality of sections. In some embodiments, the detection layer can include at least one channel to control and direct the flow of fluid or particular compounds through the channels in the layer. In yet some other embodiments, the detection layer can include a membrane that separates particular compounds or targeted substances for detection, for example by phase separation or other distinguishing indicia.

In some embodiments, the detection layer may be positioned on, within, and/or below a surface of an object. In some instances, the object may be a fingernail, an artificial fingernail, a layer of fingernail polish, a fingernail sticker, a press-on nail, a fingernail decal, a sticker, a ring, a bracelet, a necklace, a charm, a lanyard, or other appropriate surface.

In some cases, the detection layer further comprises an absorbent. In some embodiments, the detection layer may be pre-treated with a desiccant. The absorbent can include chromatography paper, silica gel, or alumina.

In some instances, the detection layer comprises a lateral flow assay. In some examples, the lateral flow assay may be multiplexed for testing for the detection of multiple compounds. In some embodiments, the apparatus comprising a lateral flow assay can be laminated. In some embodiments, the lateral flow assay may be arcuate-shaped. Lateral flow assays that can be included within the present apparatus are described and set forth in a PCT patent application entitled "Methods and Apparatus for Detecting Compounds in Liquids," applied for by Undercover Colors, Inc. and filed on the same day as the present application, which is incorporated by reference in its entirety.

In some embodiments, the detection layer comprises a single layer, film, or cartridge. In some embodiments, the detection layers comprises a plurality of layers or stages that make up the detection layer. For example, the detection layer can include a plurality of sub-layers or stages are configured to absorb a liquid, provide a matrix through which the liquid can travel, and provide a reservoir for collecting liquid that travels through the matrix. In some such embodiments, the plurality of sub-layers comprise the detection layer. In some embodiments, the detection layer can comprise two, three, four, five, six, or seven sub-layers or more. For example, the detection layer could include up to twenty sub-layers. In some embodiments, the detection layer can be referred to herein as a detection subassembly.

In some embodiments, a sample pad material can be included within the detection layer. The sample pad can aid in the wetting of the detection layer. The sample pad can limit the amount of liquid that flows into the apparatus. In some embodiments, once the sample pad is saturated, the rate of absorption of the liquid can decrease and thus limit the amount of liquid that is absorbed, controlling the flow of the liquid into the apparatus.

In some embodiments, the detection layer can be configured to minimize, significantly reduce, or substantially eliminate backflow or migration of an assay component into the test liquid. This backflow or potential flow of constituents from the detection layer to the test liquid may be undesirable, especially for testing of consumable liquids. In some embodiments, the potential backflow or reverse flow may comprise the test liquid and chemical additives from the detection layer. To address the potential for backflow, in some embodiments, the detection layer may further comprise a backflow reduction component. In some embodiments, the backflow reduction component may be an untreated pad between the sample port or opening in the top layer and the sample pad. The untreated pad may minimize, significantly reduce, or substantially eliminate potential flow of material back to the test liquid due to saturation of the untreated pad upon introduction of the apparatus into the test liquid. Once introduced into the test liquid, the saturated untreated pad may serve as a constraint on backflow by minimizing the gradient and motive force of flow from the sample pad to the test liquid. In some embodiments, this constraint of flow by the saturated untreated pad may at least significantly reduce potential contact between chemical additives or buffers from the detection layer and the test liquid. In some embodiments, the constraint of flow by the saturated untreated pad may help ensure that essentially none of the chemical additives or buffers from the detection layer come in contact with the test liquid. In some embodiments, the design and configuration of the top layer and bottom layer may sufficiently encase the detection layer to substantially prevent backflow to the test liquid. In this embodiment, the opening for liquid entry is small in comparison to the size and surface area of the apparatus. For example, when the wearable apparatus is introduced to a liquid, the relatively small opening for liquid presents the only potential backflow path. The substantially small size of the opening reduces the potential for back flow. In some examples, the backflow reduction component can prevent at least about 70% of the assay components from migrating into the liquid sample, for example, at least about 75%, at least about 80%, at least about 85%, at least about 90%, at least about 95%, or at least about 99%.

In some embodiments, the apparatus comprises a boundary that may substantially prevent liquid entrainment at the boundary when the apparatus is fully submerged. In some examples, the boundary refers to the peripheral edge of the apparatus or the perimeter of two joined edges. In some embodiments, the apparatus comprises a boundary that can be configured to substantially prevent liquid entrainment at the boundary when the apparatus is fully submerged. The boundary configuration may be achieved by any one of adhesive, bond, weld, compressive force, mateable arrangements (stud/anti-stud), electrostatic interaction, and magnetic interaction or other methods. In such cases, the full submersion of the apparatus in a liquid may have no effect on the detection layer. In some embodiments, the opening for liquid entry is small in comparison to the size and surface area of the sealed apparatus. For example, when the apparatus is introduced to a liquid, the relatively small opening for liquid presents the only path to the detection layer. The substantially small size of the opening reduces the potential for flooding of the detection layer.

In some cases, the area of the opening comprises less than about 30% of the total surface area of the top of the apparatus, for example, an area of the opening of about 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, and 1%. In some examples, the area of the opening may be about 1% to 30%. In some cases, the area of the opening comprises less than about 1% of the total surface area of the top of the apparatus, for example, an area of the opening of about 0.9%, 0.8%, 0.7%, 0.6%, 0.5%, 0.4%, 0.3%, 0.2%, 0.1%. In some examples, the area of the opening may be about 5% to 0.1%.

In some embodiments, the absorbent capacity of the wick or absorbent layer may also reduce the potential for back flow. For example, the wick or absorbent layer may have an absorbent pad capacity substantially greater than the intended sample volume of the detection layer; the substantially greater absorbent pad capacity may reduce the potential for backflow by ensuring virtually all of the sample and companion detection layer chemicals are drawn into the absorbent layer. In some embodiments, the capacity of the absorbent pad may be 50 to 100% greater than the intended sample volume.

In some embodiments a detection layer comprises a chromatographic membrane pad capable of receiving a liquid and allowing for migration of the liquid. In some instances, the chromatographic membrane can include an anti-analyte antibody-particle conjugate at least a first location and an analyte-conjugate protein at least a second location. In some embodiments, the chromatographic membrane pad further comprises an anti-species antibody at at least a third location. In some instances, the apparatus further comprises a sample pad capable of receiving the liquid, and in some cases, the liquid moves from the sample pad to the chromatographic membrane. In some embodiments, the liquid moves from the chromatographic membrane to a wick or absorbent pad. In some embodiments, the detection layer further comprises a conjugate pad. In some embodiments, the sample pad and conjugate pad may be connected. In other embodiments, the sample pad and conjugate pad may be combined. In some embodiments, at least a portion of the sample pad-conjugate pad overlaps the chromatographic membrane pad. In some embodiments, the sample pad-conjugate pad and the absorbent pad are not connected. In some embodiments, the absorbent pad can be separated from the chromatographic pad with an impermeable membrane, except for the area where the absorbent pad overlaps a portion of the chromatographic membrane pad.

In some embodiments, the detection layer can be configured to direct flow of a liquid through the detection layer in a generally horizontal orientation, e.g., substantially along a single horizontal plane from a first end of the detection layer to the second end of the detection layer. In other embodiments, the detection layer can be configured to direct flow of a liquid through the detection layer in a generally vertical orientation, e.g., substantially through a plurality of vertical planes, i.e., from the bottom of the detecting layer to the top of the detecting layer. In some embodiments, the detection layer can be configured to split the flow of a liquid through the detection layer into multiple paths. In some embodiments, the liquid may flow along from a first path to a second curved path that is substantially parallel to the first path. In some embodiments, this second path may flow counter-current to the direction of the first path.

In some embodiments, the configuration of the detection layer, specifically the relationship of the chromatographic membrane pad and the absorbent to each another may result in a flow path in a portion of the detection layer being counter-current in nature. In some examples, the flow of liquid in the absorbent pad is counter-current to the direction of flow in the chromatographic membrane pad. In some embodiments, the configuration of the detection layer may allow for the overall length of the detection layer to be substantially less than a conventional detection layer that maintains a single-direction flow path throughout the length of the detection layer. By overlapping the chromatographic membrane pad and the absorbent pad, the overall length of the detection layer can be significantly reduced without reducing the length of the overall flow path of the liquid. In some embodiments, the overall length of the detection layer may be further reduced by utilizing counter-current flow paths in the detection layer.

A particular advantage of miniaturization of a lateral flow assay is timeliness of test results. For example, a conventional lateral flow assay with an 80 mm long chromatographic membrane requires a minimum of 5 minutes to display test results. In contrast, some embodiments of the miniaturized assays described herein display test results much faster. For example, a 12 mm detection layer comprising a buffer formulation as described herein requires only about 30 seconds to display test results. An additional advantage of a miniaturized lateral flow assay is reduced test fluid volume. In some examples, a sample volume of no more than 15 µL is required for an apparatus described herein, compared to 80 µL for a conventional 80 mm lateral flow assay. In some embodiments, sample volume is less than 40 µL, less than 30 µL, less than 20 µL, less than 10 µL, or less than 5 µL. In some embodiments test results are displayed in less than 1 minute, less than 30 seconds, less than 15 seconds, less than 10 seconds, or less than 5 seconds.

In some embodiments, the detection layer further comprises a cover over the chromatographic membrane. In some instances, the cover may comprise an opening to permit gas to escape, or the cover may be gas-permeable. In some cases, the cover may be an opaque cover, a tinted cover, a transparent cover, or a translucent cover. In some embodiments, the cover defines a stencil pattern, which may comprise an indication such as "yes", "no", "safe", "OK", or "☺". In some embodiments, the stencil pattern may be placed over the second position of the chromatographic membrane. Such a pattern may be helpful to the user by making the test results easy to understand.

The detection layer of certain embodiments described herein can provide an indication or signal mechanism to a user as to whether a particular compound or target substance may be present. For example, the indication can comprise the appearance of a colored dot or region, the absence of any appearance of a colored region, completing lines, logos, patterns or symbols, the printing of words, such as "SAFE," "OK," "YES," or "NO," checkmarks, emoticons or symbols such as a "☺," fluorescence, vibration, or sounds. In some embodiments, the indication can comprise the appearance of a portion of a word or symbol, for example, the indication may be the letter "A" of the word "SAFE." In some embodiments, the detection layer can provide an indication to a user by electrochemical detection, polymerization or de-polymerization in the presence of an analyte, endo- and exothermic reaction initiation, hydrogel formation, and a device-aided quantitation, for example with the aid of smartphone application or other device. In some embodiments, the presence of an indication can show a user that a target substance may be present. In other embodiments, the presence of an indication can show a user that a target substance may be absent.

In some embodiments, the detection layer can include an indication that provides a portion of a communication to the user, for example, completes a pre-printed word or symbol. For example, the detection layer (or other layers, e.g., the top layer) can include pre-printed or pre-formed characters such as the letters "S," "F," and "E." The indication can comprise the letter "A" and be aligned to display the indication of "A" between the pre-formed letters "S" and "F" such that the results of the test are displayed in the context of the pre-printed or preformed characters as "S A F E."

In some embodiments, the detection layer can include a plurality of indication or signal mechanisms. For example, the detecting layer can include a first indicator and a second indicator. In some such embodiments, the first indicator can correspond to a control, and the second indicator can correspond to a positive or negative presence of a target substance. In some embodiments, the first indicator corresponding to the control can be viewable by a user showing the user that the detecting layer was properly and sufficiently disposed to a liquid. The second indicator corresponding to the detection of a target substance can be viewable. In some embodiments, the first indicator and the second indicator can be complementary to provide a single, joined indication. For example, and not to be considered limiting, the first indicator can be a horizontal line ("—") and the second indicator can be a vertical line ("|") that intersects with the first indicator. When both the example first indicator and the example second indicator are viewable, the joined indication or character may appear as a "plus" or cross ("+"). As another example, and not to be considered limiting, the first indicator can be the letters "S," "F," and "E" and the second indicator can be the letter "A." When both the example first indicator and the example second indicator are viewable, the joined indication may appear as "S A F E." As one of ordinary skill in the art appreciates, other combinations of the first indicator and the second indicator can be utilized.

In some embodiments, the detection layer comprises a thickness ranging from about 50 microns to about 1000 microns. In some embodiments, the detection layer comprises a thickness ranging from about 200 microns to about 400 microns. In some embodiments, the detection layer can have a thickness of about 100 microns or less, 200 microns or less, 400 microns or less, 600 microns or less, 800 microns or less, or 1000 microns or less.

In some embodiments, the detection layer can be subject to different surface treatments. For example, the detection layer can be subject to a ozonation treatment. In some embodiments, the detection layer can be subject to one or more surface treatments that can increase the hydrophilicity of the layer, and can in some cases, improve wetting properties of the layer. In some embodiments, the surface treatment can aid in prevent air pockets or bubbles from forming at an opening when the apparatus is exposed to a liquid.

In some embodiments, the detection layer can be configured to detect the presence of a plurality of targeted substances. For example, the detection layer can be configured to detect multiple illicit drugs on one particular detection layer. In some embodiments, the detection layer can be physically divided to permit the detecting of multiple drugs without the inferring with the detection of another drug. As another example, a detection layer can be multiplexed with certain components to test for multiple drugs on a single detection layer. In some embodiments, the apparatus can include a plurality of discrete, physical sections positioned adjacent to each other to make up a single detection layer. For example, a plurality of matrices can be positioned side by side with each matrix configured to test for the presence of a different compound in a liquid.

In some embodiments, the apparatus comprising a detection layer can also include at least one additional layer. In some embodiments, the apparatus can include at least one of a top layer, a bottom layer, and a removable layer. In some embodiments, the apparatus can include any combination of layers described herein.

The apparatus described herein can also include a top layer positioned on a top surface of a detection layer. In some embodiments, the top layer can be coupled to the detection layer using an adhesive. In some embodiments, the adhesive can comprise acrylate copolymer microspheres, acrylic and methacrylic ester homo- or copolymers, butyl rubber based systems, silicones, urethanes, vinyl esters and amides, olefin copolymer materials, di-alkyl fumarates, natural or synthetic rubbers, and the like, including hot-melt adhesives.

Coupling as described herein may be direct or indirect. The layers may be coupled by adhesive, bond, weld, compressive force, mateable surfaces (stud/anti-stud), electrostatic interaction, magnetic interaction, otherwise covering a surface, or other methods known to those of skill in the art.

In other embodiments, the top layer can be coupled to the detection layer by heat sealing at least a portion of the respective layers, by ultrasonic welding the two layers, through the use of ultraviolet radiation curable adhesive, or through the use of pressure-sensitive adhesives. In some embodiments, other suitable binding material or methods known to those of skill in the art can be used to couple the detection layer to the top layer.

In some embodiments, the top layer defines an opening through which at least a portion the detection layer may be exposed. In some embodiments, the opening provides a channel through which the detection layer can absorb a liquid to be tested. In some embodiments, the opening can be positioned at an end or boundary edge of the top layer, for example at a tip, to provide a channel through which the detection layer can absorb a liquid to be tested.

In other embodiments, the detection layer can include an opening at an end or boundary of the detection layer, for example at a tip, to provide a channel through which the detection layer can absorb a liquid to be tested. The end or boundary of the detection layer can be positioned in proximity to an end or boundary of the apparatus.

The top layer can be an opaque cover, a tinted cover, a transparent cover, or a translucent cover. Optionally, the top layer can include one or more perforations. These perforations can allow for the escape of gaseous materials during the use of the apparatus. In some embodiments, the top layer may be a gas permeable membrane. As fluid is absorbed by the detection layer, the gas or air within the test may be displaced and escape or venting of the displaced gas may be needed.

In examples where the top layer may be opaque, tinted, or translucent, the top layer can optionally include one or more transparent windows on the top layer. In some embodiments, the transparent window can be aligned and positioned on the detection layer such that the indication or signal mechanism of the detection layer can be visible through the transparent window. Window may include opening, aperture, void, lens, or the like. In some embodiments, the transparent window of the top layer can be shaped as certain words, such as "SAFE," "OK," "YES," or "NO," checkmarks, completing lines, logos, patterns or symbols, emoticons or symbols such as a "☺," that can provide the results of the test to a user.

In some embodiments, the top layer comprises a laminate layer. In some embodiments, the top layer comprises a thin film. The top layer can be constructed of different materials. In some embodiments, the thin film comprises at least one of a metal material, polymeric material, ceramic material, inorganic material, and other suitable material. In some embodiments, the top layer can comprise one or more of ABS (acrylonitrile butadiene styrene), ABS+PC (ABS+polycarbonate alloy), acetal (POM) (polyoxymethylene), LCP (liquid crystal polymer), Nylon 6-PA (polyamide), Nylon 6/6-PA (polyamide), Nylon 11-PA (polyamide), PBT polyester (polybutylene terephthalate), PC (polycarbonate), PEI (polyetherimid), PE (polyethylene), LDPE (low density polyethylene), HDPE (high density polyethylene), PET polyester (polyethylene terephthalate), PP (polypropylene), PPA (polyphthalamide), PPS (polyphenylene sulfide), PS (polystyrene crystal), HIPS (high impact polystyrene), PSU (polysulfone), PVC (polyvinylchloride), PVDF (polyvinylidene fluoride), SAN (styrene acrylonitrile), TPE (thermoplastic elastomer), TPU (thermoplastic polyurethane elastomer), copolymers thereof, metal foils, and mixtures thereof. The polymeric materials may be thermosetting or thermoplastic. These polymers typically have a tensile strength in the range of 1,000-50,000 psi; a flexural modulus of 5,000 to 5,000,000 psi; an impact strength of 0.1 ft-lb/in notched Izod to 30 ft-lb/in notched Izod.

In some embodiments, the top layer can be subject to different surface treatments. For example, the top layer can be subject to a ozonation treatment. In some embodiments, the top layer can be subject to one or more surface treatments that can increase the hydrophilicity of the layer, and can in some cases, improve wetting properties of the layer. In some embodiments, the surface treatment can aid in prevent air pockets or bubbles from forming at an opening when the apparatus is exposed to a liquid.

In some embodiments, the top layer comprises a thickness ranging from about 10 microns to about 1000 microns. In some embodiments, the top layer comprises a thickness ranging from about 200 microns to about 400 microns. In some embodiments, the top layer can have a thickness of about 100 microns or less, 200 microns or less, 400 microns or less, 600 microns or less, 800 microns or less, or 1000 microns or less.

In some embodiments, the apparatus has sufficient structural strength to resist structural change from an external force that would damage the apparatus to the extent that the apparatus did not function to achieve an intended result. In some embodiments, the top layer provides the structural strength of the apparatus, or substantially all of the structural strength of the apparatus. In some embodiments, a bottom layer (as described below) provides the structural strength of the apparatus, or substantially all of the structural strength of the apparatus. In some embodiments, the top layer and the bottom layer provide the structural strength of the apparatus. Structural changes that could damage the apparatus, depending on the nature of the apparatus, may include deformation, collapse, creasing, puncture and the like. In some embodiments, the apparatus may have sufficient structural strength to resist deformation, collapse, creasing, or puncture. By way of non-limiting examples, a structural change may: restrict liquid flow; cause the channel liquid to flow in unintended ways; cause unwanted accumulation of the detecting substance; or cause incorrect results to occur. The type of structural change that may damage the apparatus may depend, at least in part, on apparatus design.

In some embodiments, the structural strength of the apparatus may be sufficient to sustain an external axial compressive force of >0.1 Newtons and a perpendicular compressive force of >40 Newtons without impacting the ability of the apparatus to detect the presence of a targeted substance. In some embodiments, the apparatus may sustain an external axial compressive force of >0.25 Newtons and a perpendicular compressive force of >30 Newtons without impacting the ability of the apparatus to detect the presence of a targeted substance. In some embodiments, the apparatus may sustain an external axial compressive force of >0.5 Newtons and a perpendicular compressive force of >20 Newtons without impacting the ability of the apparatus to detect the presence of a targeted substance. In some embodiments, the apparatus may sustain an external axial compressive force of >20 Newtons and a perpendicular compressive force of >35 Newtons without impacting the ability of the apparatus to detect the presence of a targeted substance. In some embodiments, the apparatus may sustain an external axial compressive force of >60 Newtons and a perpendicular compressive force of >100 Newtons without impacting the ability of the apparatus to detect the presence of a targeted sub stance.

In some embodiments, the apparatus may sustain an external perpendicular force of 1000 Newtons without impacting the ability of the apparatus to detect the presence of a targeted substance. In some embodiments, the apparatus may sustain an external force of 2500 Newtons without impacting the ability of the apparatus to detect the presence of a targeted substance.

The apparatus described herein can also include a bottom layer coupled to a bottom surface of a detection layer. In some embodiments, the bottom layer can be coupled to the detection layer using an adhesive. In some embodiments, the adhesive can comprise acrylate copolymer microspheres, acrylic and methacrylic ester homo- or copolymers, butyl rubber based systems, silicones, urethanes, vinyl esters and amides, olefin copolymer materials, di-alkyl fumarates, natural or synthetic rubbers, and the like, including hot-melt adhesives.

In other embodiments, the bottom layer can be coupled to the detection layer by heat sealing at least a portion of the respective layers, by ultrasonic welding the two layers, or through the use of pressure-sensitive adhesives. In some embodiments, other suitable binding material or methods known to those of skill in the art can be used to couple the detection layer to the bottom layer. In some embodiments, the bottom layer defines an opening through which the detection layer may be exposed. In some embodiments, the opening provides a channel through which the detection layer can absorb a liquid to be tested. In some embodiments, the opening can be positioned at an end or boundary edge of the bottom layer, for example at a tip, to provide a channel through which the detection layer can absorb a liquid to be tested.

In some embodiments where the apparatus may be positioned on an object, the bottom layer can be coupled to the object with an adhesive. For example, if the apparatus is positioned on a fingernail, the adhesive can comprise an FDA-approved adhesive for skin contact, known to those of ordinary skill in the art.

In some embodiments, the bottom layer comprises a structure of sufficient rigidity to protect the detection layer from being damaged when used or applied to a desired surface, for example, on a finger nail. In some embodiments, the bottom layer can function as an insulating layer that protects the detection layer from the environment in which the apparatus may be employed. For example, the bottom layer can be impermeable to certain fluids or materials, such as those present in fingernail polish. In some such embodiments, the bottom layer can provide a layer that eliminates or minimizes any undesired interactions between the detection layer and the external environment, for example, the fingernail polish applied to a user's fingernail.

In some embodiments, the bottom layer comprises a laminate layer. In some embodiments, the bottom layer comprises a thin film. The bottom layer can be constructed of different materials. In some embodiments, the thin film comprises at least one of a metal material, polymeric material, ceramic material, inorganic material, and other suitable material. In some embodiments, the bottom layer can comprise one or more of ABS (acrylonitrile butadiene styrene), ABS+PC (ABS+polycarbonate Alloy), acetal (POM) (polyoxymethylene), LCP (liquid crystal polymer), Nylon 6-PA (polyamide), Nylon 6/6-PA (polyamide), Nylon 11-PA (polyamide), PBT polyester (polybutylene terephthalate), PC (polycarbonate), PEI (polyetherimid), PE (polyethylene), LDPE (low density polyethylene), HDPE (high density polyethylene), PET polyester (polyethylene terephthalate), PP (polypropylene), PPA (polyphthalamide), PPS (polyphenylene sulfide), PS (polystyrene crystal), HIPS (high impact polystyrene), PSU (polysulfone), PVC (polyvinylchloride), PVDF (polyvinylidene fluoride), SAN (styrene acrylonitrile), TPE (thermoplastic elastomer), TPU (thermoplastic polyurethane elastomer), copolymers thereof, metal foils, and mixtures thereof.

In some embodiments, the bottom layer can be subject to different surface treatments. For example, the bottom layer can be subject to a ozonation treatment. In some embodiments, the bottom layer can be subject to one or more surface treatments that can increase the hydrophilicity of the layer, and can in some cases, improve wetting properties of the layer. In some embodiments, the surface treatment can aid in prevent air pockets or bubbles from forming at an opening when the apparatus is exposed to a liquid.

In some embodiments, the bottom layer comprises a thickness ranging from about 50 microns to about 1000 microns. In some embodiments, the bottom layer comprises a thickness ranging from about 200 microns to about 400 microns. In some embodiments, the bottom layer can have a thickness of about 100 microns or less, 200 microns or less, 400 microns or less, 600 microns or less, 800 microns or less, or 1000 microns or less.

The apparatus described herein can also include an activation means. In some embodiments, the activation means may be a removable layer. The removable layer can provide a layer that provides an external barrier on the apparatus, and then may be removed prior to use of the apparatus when checking for the presence of a particular substance or compound.

In some embodiments, the removable layer can be coupled to a top surface of a detection layer. In some embodiments, the removable layer can be coupled directly to the top surface of the detection layer. In other embodiments, the removable layer can be coupled indirectly to the top surface of the detection layer, for example, coupled to a top layer that may be positioned between the removable layer and the detection layer. In some embodiments, the removable layer can be removed from the apparatus to expose at least a portion of the detection layer for use to detect the presence of a target compound in a liquid. For example, in some embodiments, the removable layer can be peeled off exposing the remaining portion of the apparatus, and then inserted into a liquid. In other embodiments, the removable layer can be removed by sliding the removable layer and in turn exposing the remaining portion of the apparatus. In other embodiments, the removable layer can be removed by scratch-off type activation, for example, a wax layer that can be scratched-off to expose the remaining portion of the apparatus. In other embodiments, the removable layer can be dissolvable layer that can be removed by exposing the layer to a stimulus. In yet other embodiments, the removable layer can be removed by breaking off or snapping off a portion of the removable layer and in turn exposing the remaining portion of the apparatus, for example, breaking off a portion of a drink stirrer to expose and activate the remaining portion of the apparatus.

In some embodiments, the removable layer comprises a peelable adhesive. In other embodiments, the removable layer comprises a layer of nail polish configured to be peeled off of the apparatus. In some embodiments, the removable layer can be coupled to the detection layer or top layer using an adhesive. In some embodiments, the adhesive can comprise acrylate copolymer microspheres, acrylic and methacrylic ester homo- or copolymers, butyl rubber based systems, silicones, urethanes, vinyl esters and amides, olefin copolymer materials, di-alkyl fumarates, natural or synthetic rubbers, and the like, including hot-melt adhesives.

In other embodiments, the removable layer can be coupled to the detection layer or top layer by heat sealing at least a portion of the respective layers, by ultrasonic welding the two layers, or through the use of pressure-sensitive adhesives. In some embodiments, other suitable binding material or methods known to those of skill in the art can be used to couple the detection layer to the bottom layer.

In some embodiments, the strength of adhesion between the removable layer and for example, the top layer, may be less than the strength of adhesion between for example the top layer and the detection layer or the bottom layer and the detection layer. The relative lower strength of adhesion coupling the removable layer in the apparatus (as compared to adhesion strength between the other layers) can permit the removal of the removable layer without decoupling the remaining layers of the apparatus.

In some embodiments, the removable layer can be coupled to the top layer by a complementary tongue and groove coupling. In some such embodiments, the removable layer can be removed by sliding the removable layer in a specific direction, i.e., along the plane of the groove, to permit the removal of the removable layer and exposing of the detection layer.

In some embodiments, the removable layer comprises a structure of sufficient rigidity to protect the detection layer or other layers from being damaged when not in use, for example, on a finger nail. In some embodiments, the removable layer can function as an insulating or barrier layer that protects the detection layer from the external environment prior to the apparatus being employed. For example, the removable layer can be impermeable to certain fluids or materials, such as fingernail polish. In some such embodiments, the removable layer can provide a layer that eliminates or minimizes any undesired interactions between the detection layer and the external environment. In some embodiments, the removable layer may be waterproof. In some such embodiments, the removable layer can cause the apparatus to be substantially waterproof. Upon removal of the removable layer, the apparatus can be activated and available for use, for example, exposed to a liquid to be tested.

In some embodiments, the removable layer provides a surface upon which the external appearance of the apparatus can be modified or customized. For example, the removable layer can provide a surface upon which a manufacturer can customize the appearance with different designs, decals, logos, colors, or other indicia. As another example, the removable layer can provide a surface upon which a user can apply fingernail polish.

In some embodiments, the removable layer comprises a thin film. The removable layer can be constructed of different materials. In some embodiments, the thin film may be comprised at least one of a metal material, polymeric material, ceramic material, inorganic material, and other suitable material. In some embodiments, the removable layer can comprise polyethylene, polyethylene terephthalate, polyvinyl chloride, polyurethane, polypropylene, copolymers thereof, metal foils, and mixtures thereof. In some embodiments, the removable layer can be subject to different surface treatments. For example, the removable layer can be subject to a ozonation treatment. In some embodiments, the removable layer can be subject to one or more surface treatments that can increase the hydrophilicity of the layer, and can in some cases, improve wetting properties of the layer. In some embodiments, the surface treatment can aid in prevent air pockets or bubbles from forming at an opening when the apparatus is exposed to a liquid.

In some embodiments, the removable layer comprises a thickness ranging from about 50 microns to about 1000 microns. In some embodiments, the removable layer comprises a thickness ranging from about 200 microns to about 400 microns. In some embodiments, the removable layer can have a thickness of about 100 microns or less, 200 microns or less, 400 microns or less, 600 microns or less, 800 microns or less, or 1000 microns or less.

In some embodiments, the apparatus can additionally include a layer comprising an opening. The layer can define a particular opening to facilitate the analysis of the test results. For example, the opening can be configured in words, such as "SAFE," "OK," "YES," or "NO," checkmarks, completing lines, logos, patterns or symbols, emoticons or symbols such as a "☺." Upon the movement of a marker or other indicator to the region of layer comprising an opening, the indicator or color dye can be visible to a user through the opening facilitating the reading of the test results. In some embodiments, the layer can be a discrete layer. In other embodiments, the layer can be integrated within other layers, for example, a top layer.

In some embodiments, the apparatus can additionally include a layer comprising a defined pattern of reagents positioned in a certain manner to facilitate the analysis of the test results. For example, the pattern of reagents can be configured in words, such as "SAFE," "OK," "YES," or "NO," checkmarks, completing lines, logos, patterns or symbols, emoticons or symbols such as a "☺." Upon the movement of a marker or other indicator to the region of layer comprising the pattern of reagents, the marker or other indicator can interact with the reagent and in turn display the pattern. When the pattern is displayed, a user can more easily analyze the results of the apparatus. In some embodiments, the layer can be a discrete layer. In other embodiments, the layer can be integrated within other layers, for example, a top layer.

In some embodiments, the apparatus can be positioned on the surface of an object. In some examples, the apparatus can be positioned within an object. In other examples, the apparatus can be positioned below the surface of an object. Suitable objects include, for example, a fingernail, an artificial fingernail, a layer of fingernail polish, a fingernail sticker, a fingernail decal, a sticker, a decal, a nail decal, a mesh nail wrap, a ring, a bracelet, a necklace, a charm, a lanyard, or any other appropriate surface. Other appropriate surfaces include items that could easily and discreetly be brought into contact with a suspect liquid, providing an improved degree of personal security for the liquid consumer.

Embodiments of an apparatus and multi-layer detection system are illustrated in the figures. As will be understood, the illustrated embodiments are provided as a way to illustrate the features and advantages of the present invention and should not be read as limiting the present invention to any particular examples. Further, the use of top, bottom and side in the following description of the figures is to aid understanding and should not be read as a geographic/orientation limitation of embodiments of the present invention.

Figure 2:
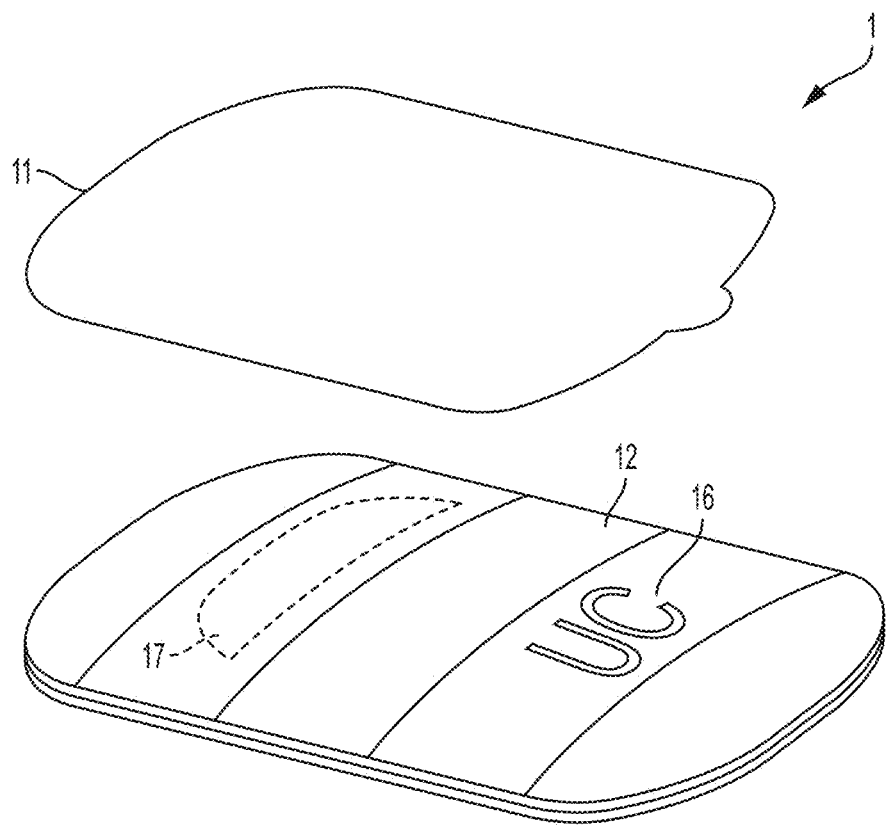
FIG. 2 shows a perspective view of an apparatus according to one embodiment of the present invention.

Turning to the figures, FIG. 1 shows an exploded view of apparatus 1 comprising a removable layer 11, a top layer 12, detection layer 13, and a bottom layer 14. FIG. 2 shows apparatus 1 in a partially assembled configuration with the removable layer 11 not being coupled to the top layer 12.

In FIG. 1, the detection layer 13 shows the direction in which a liquid travels upon exposing the apparatus to a liquid for testing. The top layer 12 comprises a window 16 at a first location and an opening 17 at a second location. The window 16 can be aligned with the detection layer 13 such that when the test is complete an indicator 15 can be visible to a user. For example, if the apparatus does not detect the presence of a certain compound in a liquid, an indication can be visible in the window 16. Window 16 is in the shape of the letters "OK," but other shapes of window 16 can be included in top layer 12. Opening 17 of the top layer can provide an opening through which liquid or other medium can travel to the detection layer 13 for testing.

Figure 3C:
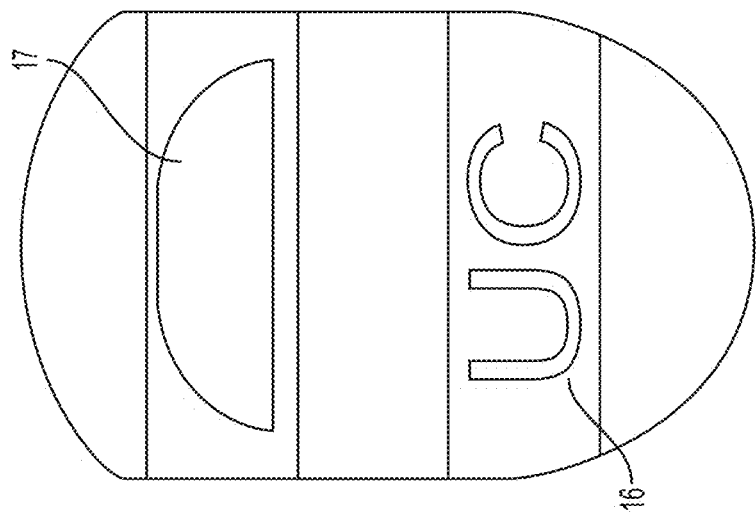
FIG. 3C shows a top view of an apparatus as described herein after conducting a test to detect a target substance with an indication that the target substance is present.
Figure 3B:
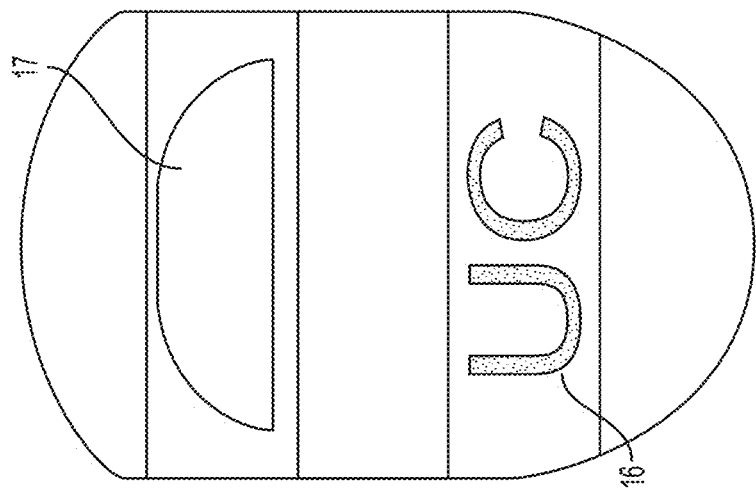
FIG. 3B shows a top view of an apparatus as described herein after conducting a test to detect a target substance with an indication that the target substance is not present.
Figure 3A:
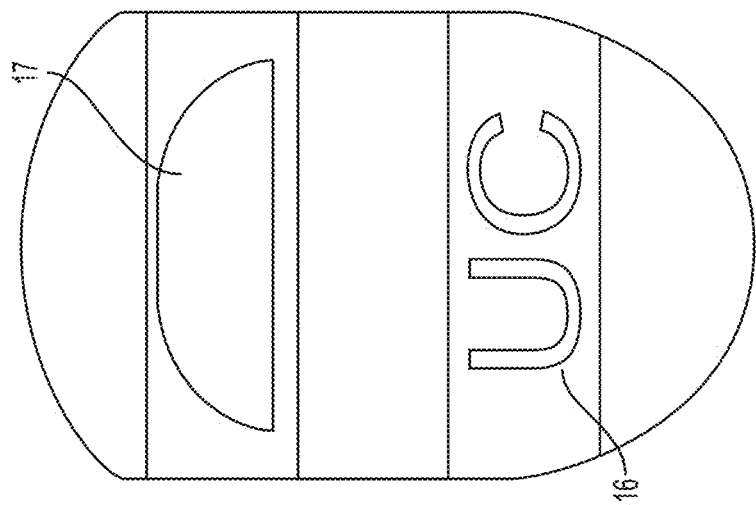
FIG. 3A shows a top view of an apparatus as described herein before initiating a test to detect a target substance.

FIGS. 3A to 3C show top views of the apparatus before and after different tests to detect a targeted substance. FIG. 3A shows the apparatus prior to testing. In FIG. 3B, the apparatus has been exposed to a liquid where the detection layer absorbs the liquid in question, and then displays the results of the test where the indicator has traveled the length of the detection layer resulting in the color being shown through the window 16. The indication shown in FIG. 3B corresponds to a test where the target substance is not present. In FIG. 3C, the apparatus has been exposed to a liquid where the detection layer absorbs the liquid in question, and then displays the results of the test where the indicator did not travel the length of the detection layer. The indication shown in FIG. 3C corresponds to a test where the target substance is present in the liquid.

Figure 5:
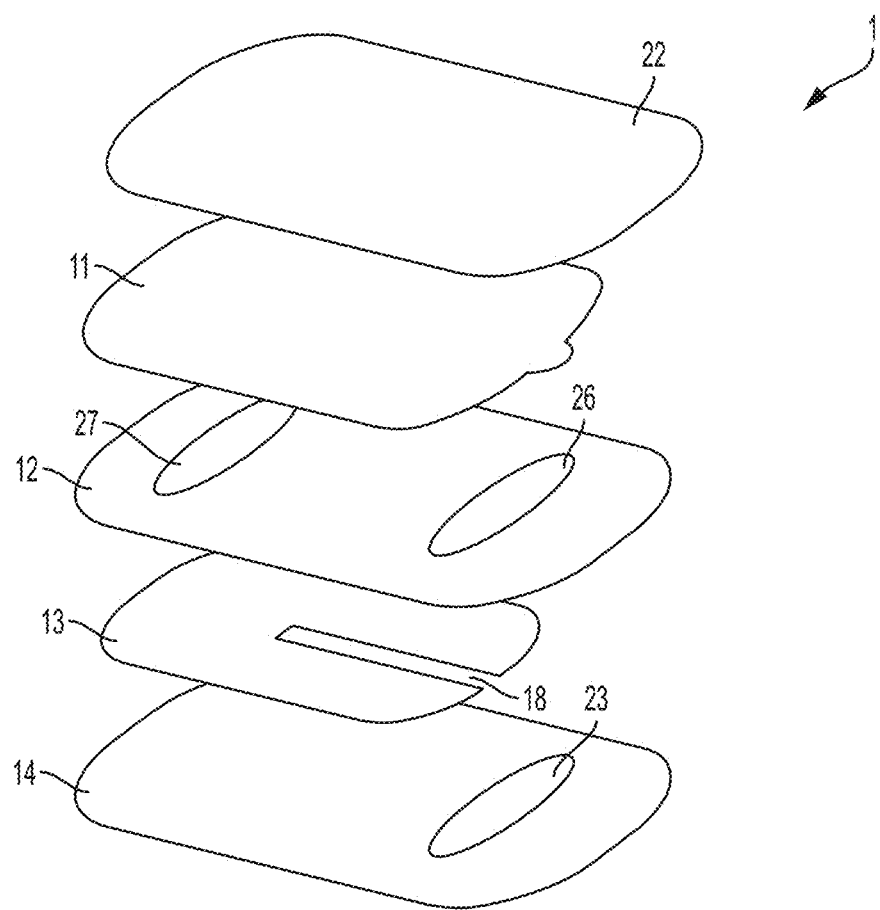
FIG. 5 shows an exploded view of an apparatus according to one embodiment of the present invention.

In some embodiments like that shown in FIG. 5, the detection layer 13 comprises a physical break that defines an optional slit 18. The slit 18 can divide the detection layer into two halves, for example, to be used to detect two target substances. The top layer 12 comprises a window 26 at a first location and a window 27 at a second location. The window 26 and window 27 can be aligned with the position of an indicator (not shown) of the detection layer 13. For example, if the apparatus does not detect the presence of a certain compound in a liquid, an indication can be visible in the window 26. In some embodiments, an optional layer 22 can be applied on the removable layer 11, such as finger nail polish, a sticker, a decal, or other materials. FIG. 5 also shows an optional window 23 positioned in the bottom layer 14. In some embodiments, the optional window 23 can be aligned with the position of an indicator (not shown) of the detection layer 13. The optional window 23 can positioned at different regions of the bottom layer 14, for example, at the opposite end of the bottom layer 14.

Figure 6:
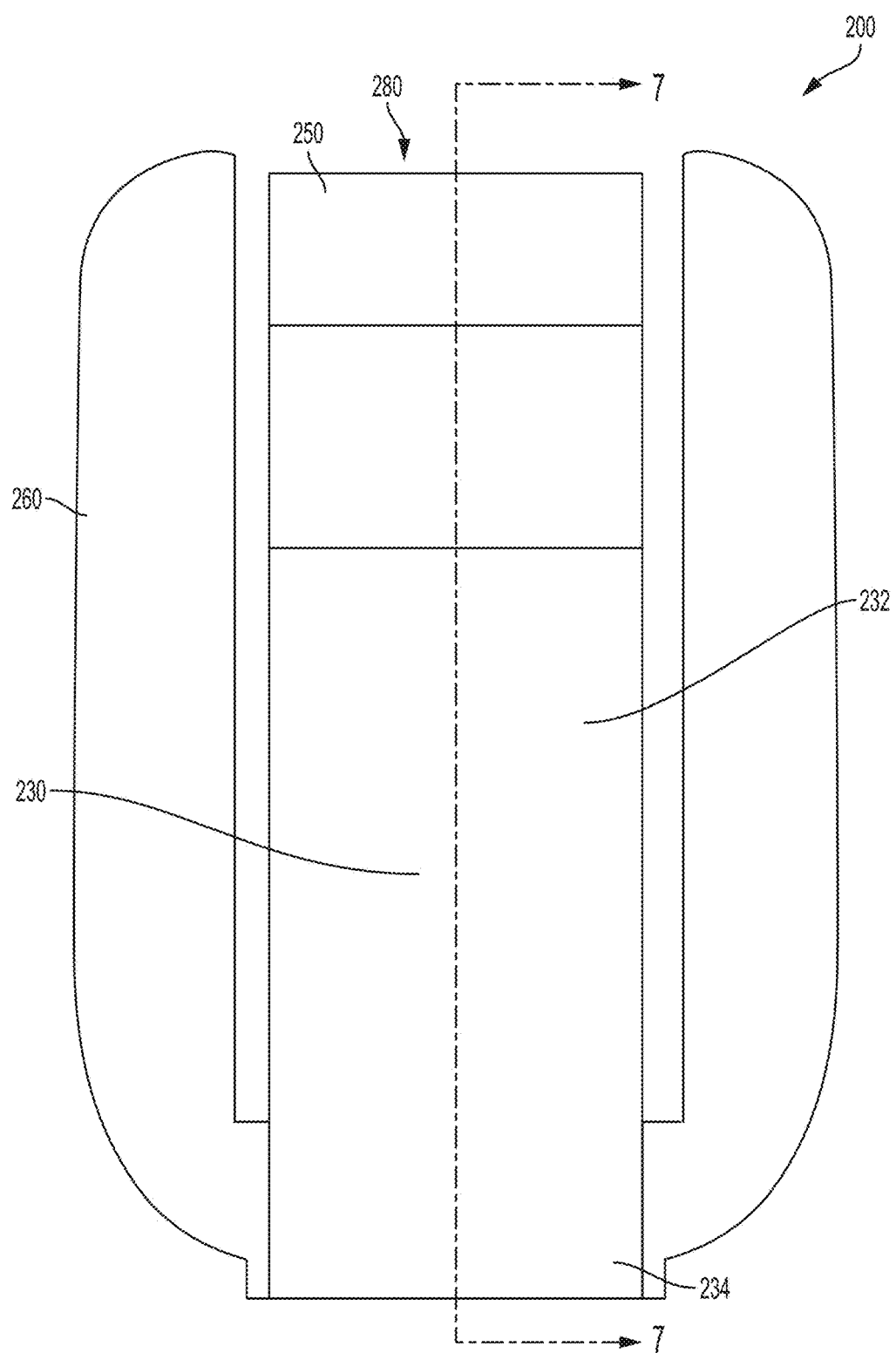
FIG. 6 shows a top view of an apparatus according to one embodiment of the present invention.

FIG. 6 shows a top view of a detection layer 200 according to one embodiment described herein. The detection layer 200 comprises an absorbent pad 260 (sometimes referred to as a wick) and a test strip 280. The test strip 280 comprises sample pad-conjugate pad 250 and a chromatographic membrane pad 230. The sample pad-conjugate pad 250 contacts the proximal end of chromatographic membrane pad 232. The sample pad-conjugate pad 250 may be separated from the absorbent pad 260. Liquid absorbed into the sample-conjugate pad 250 may flow to a distal end of the chromatographic membrane pad 234 and then flow outwardly through absorbent pad 260. The distal end of the chromatographic membrane 234 overlaps a portion of the u-shaped absorbent pad 260.

Figure 7:
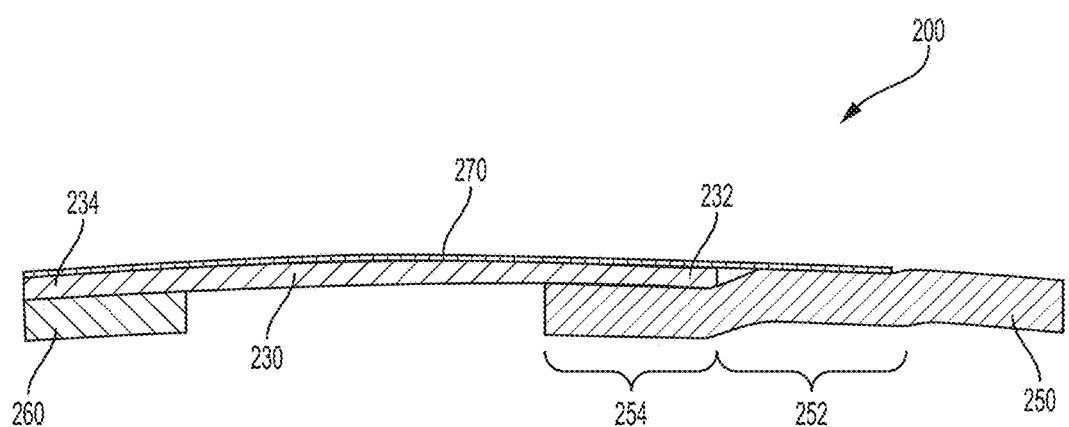
FIG. 7 shows a cross-sectional view of an apparatus according to one embodiment of the present invention.

FIG. 7 shows a cross sectional view of a detection layer 200 along the plane 7-7 shown in FIG. 6. Detection layer 200 comprises a sample pad-conjugate pad 250, a chromatographic membrane pad 230, and an absorbent pad 260. The sample pad-conjugate pad 250 overlaps with the proximal end of the chromatographic membrane pad 232 at conjugate area 254. Liquid absorbed into the sample-conjugate pad 250 may flow to a proximal end 232 of the chromatographic membrane pad 230 toward the distal end 234 of the chromatographic membrane pad 230. The distal end of the chromatographic membrane 234 overlaps a portion of the u-shaped absorbent pad 260. The absorbent pad 260 may absorb liquid from the chromatographic membrane pad 230 during use. Optionally, the detection layer 200 may have a top layer 270. In some embodiments, the top layer 270 may be adhesive. In some embodiments, the top layer 270 may be transparent. In some embodiments, the combined sample pad-conjugate pad 250 has a sample area 252 and a conjugate area 254 that do not overlap.

In some embodiments, the detection layer comprises a matrix. The matrix can include a marker. The marker can be included in the matrix by contacting the matrix with a composition comprising a marker. A marker refers to a compound, substance, or antibody coupled to a particular substance that can facilitate the detection of a target substance. For example, in some embodiments, the marker can include an antibody coupled to latex or polymer microbeads or gold nanoparticles. In some embodiments, the marker comprises carboxyfluorescein, 2,7-dichlorofluorescein, Eosin B, Eosin Y, erythrosine, fluorescein, fluorescein amidite, fluorescein isocyanate, merbromin, aptamers, antibodies, phloxine B, Rose Bengal, derivatives and salts thereof, or combinations thereof. In other embodiments, particles can be used as markers. The particle may be any colored nanoparticle such as gold and/or dye-infused polymer microbeads.

In some embodiments, the apparatus comprises a marker having the following formula:

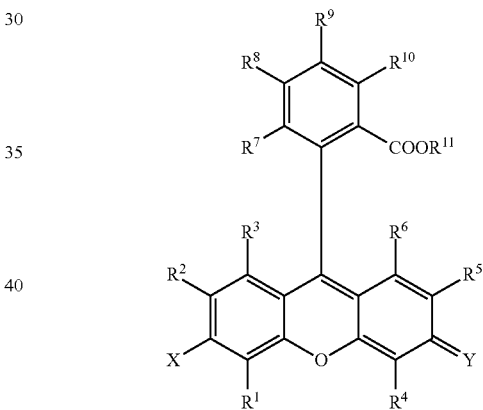

or a salt thereof, where $R^1$, $R^2$, $R^3$, $R^4$, $R^5$, $R^6$, $R^7$, $R^8$, $R^9$, and $R^{10}$ are each independently selected from the group consisting of hydrogen, halogen, hydroxyl, nitro, cyano, trifluoromethyl, substituted or unsubstituted amino, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted carbonyl, substituted or unsubstituted carboxyl, substituted or unsubstituted thio, and substituted or unsubstituted sulfonyl; $R^{11}$ is hydrogen or substituted or unsubstituted alkyl; X is hydroxyl or substituted or unsubstituted amino; and Y is O or $NR^{12}$, wherein $R^{12}$ is hydrogen or substituted or unsubstituted alkyl. In some such embodiments, the marker has the following formula:

In other embodiments, the marker has the following formula:

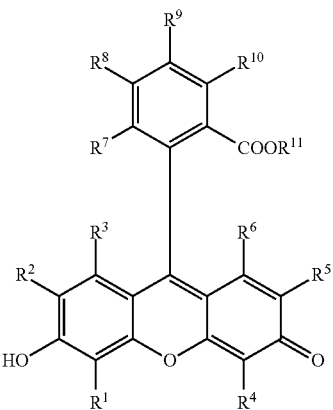

wherein $M^+$ is a cation. In some such embodiments, $M^+$ is selected from the group consisting of $Na^+$, $K^+$, $Li^+$, $Cs^+$, $Rb^+$, $Ag^+$, $Au^+$, $Cu^+$, $Fr^+$, $NH_4^+$, $NR_4^+$, and $NR_1R_2R_3^+$.

In other embodiments, the marker has the following formula:

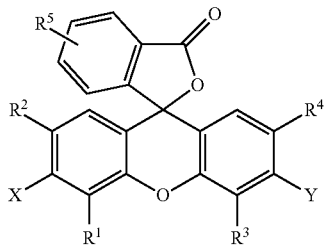

or a salt thereof, where $R^1$, $R^2$, $R^3$, $R^4$, and $R^5$ are each independently selected from the group consisting of hydrogen, halogen, hydroxyl, nitro, cyano, trifluoromethyl, substituted or unsubstituted amino, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted carbonyl, substituted or unsubstituted carboxyl, substituted or unsubstituted thio, and substituted or unsubstituted sulfonyl; and X and Y are each independently hydroxyl or substituted or unsubstituted amino.

In some embodiments, the marker can be included in the matrix by contacting the matrix with a composition comprising a marker. The marker can be present on the matrix at least a first location. For example, the marker composition can be loaded onto the matrix at the location 50 in the FIG. 4A. The amount of marker composition that can be loaded onto the matrix can be quantified by the size of the mark applied to the matrix. The amount of marker composition can be a quantity that is large enough to be visualized by the human eye. For example, the marker composition can be applied to the matrix as a dot of diameter in a range up to about 10 mm (e.g., from about 1 mm to about 10 mm or from about 1 mm to about 5 mm). The size of the applied composition can have a diameter of about 1 mm or less, 2 mm or less, 3 mm or less, 4 mm or less, 5 mm or less, 6 mm or less, 7 mm or less, 8 mm or less, 9 mm or less, or 10 mm or less. In some embodiments, the marker composition can be applied as a line in a range up to about 10 mm (e.g., from about 1 mm to about 10 mm or from about 1 mm to about 5 mm). The size of the applied composition can have a height of about 1 mm or less, 2 mm or less, 3 mm or less, 4 mm or less, 5 mm or less, 6 mm or less, 7 mm or less, 8 mm or less, 9 mm or less, or 10 mm or less.

In some embodiments, an apparatus for detecting the presence of a targeted substance comprises a length of less than about 25 millimeters, a width of about 15 millimeters, and a thickness of about 5 millimeters. In some embodiments the apparatus may be configured to detect a targeted substance present in a liquid when the targeted substance may be present in a concentration less than about 5 milligrams per milliliter. In some embodiments, the apparatus can detect the presence of the targeted substance upon being exposed to the targeted substance for less than ten seconds. In some embodiments, the apparatus can provide indication of the presence of the targeted substance in less than 5 minutes after being exposed to the liquid.

In some embodiments, the detection layers of the apparatuses according to the description herein comprise a matrix. The matrix can comprise one or more polymers. In certain embodiments, the one or more polymers comprise polysaccharides. Suitable polysaccharides for use in the matrix include agar, agarose, alginate, carrageenan, cellulose, chitosan, dextran, konjac, and mixtures thereof. In some embodiments, the matrix includes cellulose or cellulose derivatives, including surface-functionalized cellulose. Exemplary agarose polymers include, for example, carboxymethyl agarose, diethylaminoethyl agarose, and like derivatives. Optionally, the agarose polymers for use in the matrix are commercially available from Pharmacia Fine Chemicals, Inc. (Piscataway, N.J.). Exemplary cellulose polymers include, for example, cellulose esters (e.g., cellulose acetate, cellulose acetate butyrate, cellulose acetate propionate), carboxymethyl cellulose, diethylaminoethyl (DEAE) cellulose, nitrocellulose, phosphocellulose, quaternary ammonium substituted cellulose, and sulfoxyethyl cellulose. Optionally, the cellulose polymers for use in the matrix are commercially available from Whatman Co. (Whatman Paper Co., Ltd., Maidstone, England) or BioRad Corp. (Richmond, Calif.).

The matrix can further include an absorbent. In some embodiments, the matrix can comprise a plurality of absorbents. For example, the absorbent can include chromatography paper, filter paper, and other materials typically used for chromatography, such as for paper chromatography or thin layer chromatography (TLC). The chromatography paper and filter paper can be qualitative or quantitative filter paper, such as the chromatography paper and filter paper commercially available from Whatman Co. (Whatman Paper Co., Ltd., Maidstone, England).

Optionally, the absorbent comprises silica gel, alumina, high performance thin layer chromatography (HPTLC) silica gel, polysilicic acid, aluminum oxide, cellulose, polyamide, reversed phase silica Gel $C_2$ (dimethyl bonded), reversed phase silica gel $C_2$ (ethyl bonded), reversed phase silica gel $C_8$ (octyl bonded), reversed phase silica gel $C1_8$ (octadecyl bonded), acetylated cellulose, silica gel modified with amino groups, silica gel modified with cyano groups, Kieselghur impregnated with hydrocarbons, anionic and cationic anion exchange resins, diethylaminoethyl cellulose, and mixtures of the listed sorbents. The absorbent can be immobilized on an inert surface.

Optionally, the matrix can be pre-treated with a desiccant to integrate the desiccant into the matrix. The desiccant can be any desiccant as known to those of skill in the art, including, but not limited to, molecular sieves, silica gels, clays, synthetic polymers, and starches. For example, suitable desiccants include alumina, bauxite, anhydrous calcium sulfate, water-absorbing clays, silica gel, zeolite, and mixtures thereof.

Optionally, the matrix can be pre-treated with a buffering agent. The buffering agent can be, for example, acetic acid and a conjugate base thereof, citric acid and a conjugate base thereof, dibasic sodium phosphate, polyelectrolyte polymers, potassium hydrogen phthalate, sodium hydroxide, sodium phosphate, and combinations thereof. The matrix can be pre-treated with a buffering agent such that the matrix may be buffered at a pH ranging from about 3 to about 8 (e.g., from about 4 to about 6 or from about 4.5 to about 5.5). For example, the buffering agent can be added to the composition to provide a pH of about 3, about 3.5, about 4, about 4.5, about 5, about 5.5, about 6, about 6.5, about 7, about 7.5, about 8, about 8.5, or about 9. Buffers that can used in the described apparatus can include, for example, those described and set forth in a PCT patent application entitled "Methods and Apparatus for Detecting Compounds in Liquids," applied for by Undercover Colors, Inc. and filed on the same day as the present application, which is incorporated by reference in its entirety.

For example, a first buffer solution may be applied to a sample area to deposit buffering compounds and buffer additives selected to neutralize or counteract beverage components that might interfere with a test result. Another buffer solution may be applied to the chromatographic membrane to increase the viscosity of the beverage or liquid, for example to slow its migration across the chromatographic membrane. In some embodiments specific combinations of buffer solutions may be used in an apparatus where a first buffer solution is applied to the sample area, a second buffer solution is applied to the chromatographic membrane, and the first and second buffer solutions are different. Such combinations of buffer solutions can be used synergistically to improve the performance of the apparatus and methods across a wide range of test liquids.

In some embodiments, specific combinations of neutralizing agents, buffering agents, and surfactants are used synergistically to improve the performance of the assay across a wide range of sample matrices. Neutralizing agents can be used alone or in combination with buffering agents to improve assay performance across a diverse set of test liquids. Neutralizing reagents may include traditional buffering agents, such as Good's buffer salts, and other acidic or basic components which treat the sample prior to the sample encountering the detection means. Neutralizing reagents may consist of carboxylate salts such as sodium citrate or potassium carbonate. Buffering reagents create a stable and consistent environment for the detection means to function within and may consist of ionic or zwitterionic buffer salts. Alone buffering agents may not provide adequate neutralization of all sample types. Neutralizing agents alone may be too acidic or basic to be compatible with the detection means. For example, one potential combination of neutralizing agent and buffering agent is potassium carbonate (0.1 to 3M) and tris (0.1M to 3M), respectively, at any combination of neutralizing and buffering agent concentrations within the specified ranges. In some embodiments, the ratio of neutralizing agent to buffering agent is 2:1.

The neutralizing agent may be located in an assay component such as the sample pad or area which is separate from the buffering agent located in the conjugate pad or area. In some cases, the neutralizing agent is K2CO3 (0.1 to 3M) or other carboxylate salt. In some cases, the buffering agent is Tris (0.1M to 3M) or other Good's buffer agent. Separation of the neutralizing agent from the conjugate pad is of particular importance when the neutralizing agent is not compatible with the antibody-particle conjugate as is the case with K2CO3 and antibody-gold nanoparticle conjugates. The neutralizing agent may deposited on the same assay component but in a separate area from the detection means. In some cases, the neutralizing agent is K2CO3 (0.1 to 3M) or other carboxylate salt. In some cases, the buffering agent is Tris (0.1M to 3M) or other Good's buffer agent.

In some embodiments, certain combinations of non-ionic surfactants are particularly useful for ensuring an apparatus described herein is compatibile with a wide range of test liquids. These non-ionic surfactants may be used alone or in conjugation with neutralizing and buffering agents. In some examples, a first non-ionic surfactant is Pluronic F68 (0.1% to 2%) or other poloxamer and a second non-ionic surfactant is Triton X-100 (0.1% to 2%) or other polyethylene oxide phenyl ether at any combination of concentrations within the stated ranges for each compound. Buffer formulations and residual buffer formulation may comprise a first and a second non-ionic surfactant at any combination of concentrations within the stated ranges for each surfactant. The non-ionic surfactants may be located in the conjugate pad. The non-ionic surfactants may be located in the sample pad. One non-ionic surfactant may be located in the sample pad and one non-ionic surfactant may be located in the conjugate pad.

In some embodiments, combinations of neutralizing agents, buffering agents, and non-ionic surfactants were found to improve assay performance. For example, a useful combination includes the neutralizing agent K2CO3 (0.1 to 3M), buffering agent Tris (0.1M to 3M), the non-ionic surfactant Triton X-100 (0.1 to 2%), and a second non-ionic surfactant Pluronic F68. In some examples, an apparatus described herein includes a specific combination of residual buffer formulations that can render the apparatus compatible with a wide range of test fluids. For example, a first residual buffer formulation may be used at a location near the beginning of the liquid flow path, for example the sample area, to interact with components in the test fluid that could be detrimental to test results, such as acids, alcohol, and/or colorants, and a second residual buffer formulation may be used at a separate location further down the liquid flow path to buffer the test liquid near a certain pH so as not to denature proteins involved in the assay.

In addition, a specific combination of buffer formulations can allow combining multiple detection means (such as using two or more marker-test line combinations) for detecting multiple analytes, whereas in the absence of the specific combination of residual buffer formulations the different detection means would not be compatible with the same scope of test fluids. In one example, in the absence of a particular residual buffer formulation, a first detection means for detecting a first analyte is only compatible with test fluids A and B, and a second detection means for detecting a second analyte is only compatible with test fluids B and C. In that case, the first and second means could not be used in combination to simultaneously detect the first and second analytes in fluids A and C. But a single apparatus including an appropriate combination of residual buffer formulations is compatible with fluids A, B, and C, and can detect the first and the second analytes in all three fluids. This "multiplexing" is useful for the detection of multiple analytes with may require different detection means (such as different antibodies, aptamers, or markers) with a single apparatus. In some examples, an apparatus described herein may detect the presence of both benzodiazepines and ketamines.

In some embodiments, the methods and apparatuses described herein do not rely on the observation or measurement of color change of the markers to detect the presence of amine-containing compounds in a liquid. In some embodiments, the methods and apparatuses described herein do not rely on other techniques, such as electrophoresis. Instead, in some embodiments, the presence of a target substance may be indicated by changes in the movement of colored material or a complex through the matrix. When the matrix containing the marker is exposed to a liquid, if no target substance, is present in the liquid, the marker color will move freely with the solvent front 40 as it advances through the matrix. However, when one or more of the target substances is present in the liquid, the color will not advance with the solvent front 40 or it will advance only slowly relative to the rate of advance in a blank control sample.

Figure 4A:
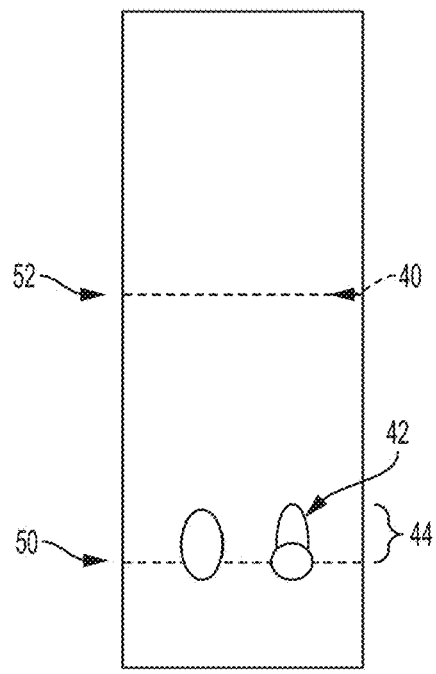
FIG. 4A is an illustration of an apparatus as described herein showing the presence of a compound in a liquid.
Figure 4B:
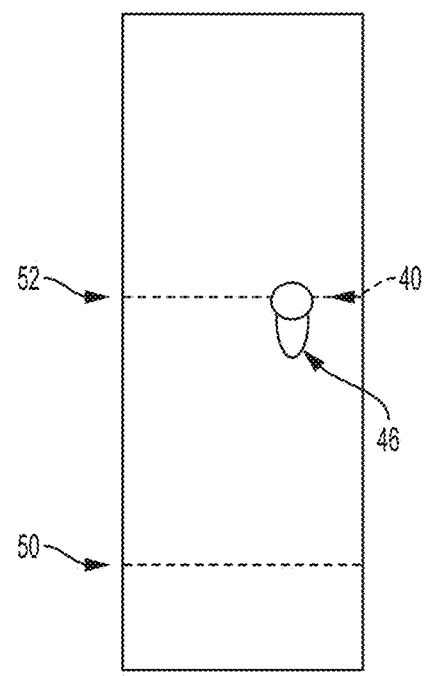
FIG. 4B is an illustration of an apparatus as described herein showing the absence of a compound in a liquid.

If a target substance to be detected is present, the small dot or line of marker 44 does not substantially move (see, for example, FIG. 4A). As defined herein, "does not substantially move" means that the small dot or line of marker at location 50 remains at location 50 or moves less than about 25% of the solvent front 40 distance relative to location 50. For example, the dot or line of marker 44 moves less than about 15%, less than about 10%, less than about 5%, less than about 4%, less than about 3%, less than about 2%, less than about 1%, or less than about 0.5%. In some examples, if a target substance to be detected is present and the marker does not substantially move, the marker can "tail" 42 as the solvent front 40 moves along the length of the matrix (see, for example, FIG. 4A). When the target substance is not present in the liquid in an amount that is detectable, the marker dot or line substantially moves with the liquid along the front 40, possibly with some tailing 46 behind the moving marker dot or line (see, for example, FIG. 4B). It should be appreciated that FIGS. 4A and 4B are intended to be generalized schematics of the method of detecting a target substance described herein, as understood by one skilled in the art.

In some embodiments, the detection layer comprises a lateral flow assay. In some embodiments, the lateral flow assay can rely on antibody-analyte interactions to determine the presence of drugs in an alcoholic or non-alcoholic beverage. In some embodiments, the lateral flow assay can rely on aptamer-analyte interactions to determine the presence of an analyte in a liquid. In some embodiments, the lateral flow assay can include an anti-drug antibody that is conjugated to colored particles which can be carried through a chromatographic membrane upon which a drug-conjugated protein (test line) and an anti-species antibody (control line) are immobilized. In some embodiments, the colored particles can include gold nanoparticles. In some embodiments, the colored particles can include dye-infused latex microbeads. In some embodiments, the chromatographic membrane can include cellulose, nitrocellulose, glass fiber, similar materials, or a combination of these materials. Lateral flow assays that can used in the described apparatus can include, for example, those described and set forth in a PCT patent application entitled "Methods and Apparatus for Detecting Compounds in Liquids," applied for by Undercover Colors, Inc. and filed on the same day as the present application, which is incorporated by reference in its entirety.

In some embodiments, upon exposure of the detection layer comprising a lateral flow assay to a beverage, the fluid absorbed by the detection layer can move through the detection layer carrying with it the anti-drug antibody-particle conjugate so that it passes over the immobilized drug-protein conjugate and anti-species antibody. If no drug is present the anti-drug antibody-particle conjugate will interact and bind to the drug-protein conjugate as well as the anti-species antibody which will cause the anti-drug antibody-particle conjugate to become immobilized as well. The immobilization of the anti-drug antibody-particle conjugate can result in the deposition of color on the areas where the drug-protein conjugate (test line) and anti-species antibody (control line) are located. In the case where drug is present in the beverage, the drug will bind the anti-drug antibody-particle conjugate in turn preventing the anti-drug antibody-particle conjugate from interacting with and binding the drug-protein conjugate (test line). Because the drug inhibits the interaction and binding between the anti-drug antibody-particle conjugate and the test line, no color will be deposited in this area. Because the interaction and binding of the anti-drug antibody-particle conjugate with the anti-species antibody (control line) is not impacted by the presence of drug, there will still be deposition of the color on the control line. In some embodiments, a result indicating no drug is present consists of two lines (test and control lines are colored) while a result indicating that drug is present consists of one lines (control line is colored). In other embodiments, a result indicating the target analyte is present consists of one line (control line is colored) while a result indicating that the analyte is not present consists of two lines (test and control lines are colored).

In some embodiments, the detection layer comprising a lateral flow assay includes a buffering agent. The buffering agent can modify the properties of the absorbed samples to make the solution compatible with the antibody-particle conjugate. The buffering agents can include additives such as organic and inorganic acids, salts, ionic and non-ionic detergents, sugars, and proteins. Buffers that can used in the described apparatus can include, for example, those described and set forth in a PCT patent application entitled "Methods and Apparatus for Detecting Compounds in Liquids," applied for by Undercover Colors, Inc. and filed on the same day as the present application, which is incorporated by reference in its entirety. In some embodiments, the additives can also serve the function of preparing the membrane(s) for the flow of the liquid sample through the matrix. These additives can facilitate flow of the sample through the membrane while simultaneously preventing unwanted interactions between the membrane and the anti-drug antibody-particle conjugate, drug-protein conjugate, and anti-species antibody. The concentrations and combination of reagents tend to be dictated by the sample matrix being tested.

In some embodiments, the detection layer comprising a lateral flow assay, the lateral flow assay can have a length of less than about 12 mm, a width of less than about 6 mm, and a thickness of less than about 1.5 mm. In some embodiments, the lateral flow assay can have a length of about 10 mm, a width of about 4 mm or less, and a thickness of about 1 mm or less. In some embodiments, the lateral flow assay can have a length of about 10 mm, a width of about 3 mm or less, and a thickness of about 1 mm or less. For example, the length of the lateral flow assay can be about 24 mm, 23, mm, 22 mm, 21 mm, 20 mm, 19 mm, 18 mm, 17 mm, 16 mm, 15 mm, 14 mm, 13 mm, 12 mm, 11 mm, 10 mm, 9 mm, 8 mm, 7 mm, 6 mm, or 5 mm. In other examples, the width of the lateral flow assay can be about 6 mm, 5 mm, 4 mm, 3 mm, 2 mm, or 1 mm.

In some embodiments, the detection layer comprising a lateral flow assay can comprise a linear flow channel. In other embodiments, the detection layer comprises a channel have a non-linear shape, for example, curved, spiral, angled shape, or U-shape. In other embodiments, the flow channel may split into multiple paths. In some of these embodiments, the multiple paths may curve and may be substantially parallel to the non-split flow path. In some embodiments, the multiple paths may flow counter-current to the non-split flow path.

In some embodiments, the lateral flow assay can comprise multiple drug detections configurations on a single assay.

In some embodiments, the lateral flow assay can have an extended storage life. In some embodiments, the detection layer comprising a lateral flow assay (and apparatus) can be laminated to provide protection from external environment without compromising the integrity of the test by permitting gas permeability during use.

In some embodiments, the apparatus comprising a lateral flow assay can include a stencil layer as described above to facilitate the readability of the results of the test.

As described above, the apparatus can be positioned on, within, and/or below a surface of an object. In some instances, the apparatus may be incorporated into a fingernail or an artificial fingernail. FIGS. 8-25 show examples of the apparatus embodied as fingernails.

Figure 8:
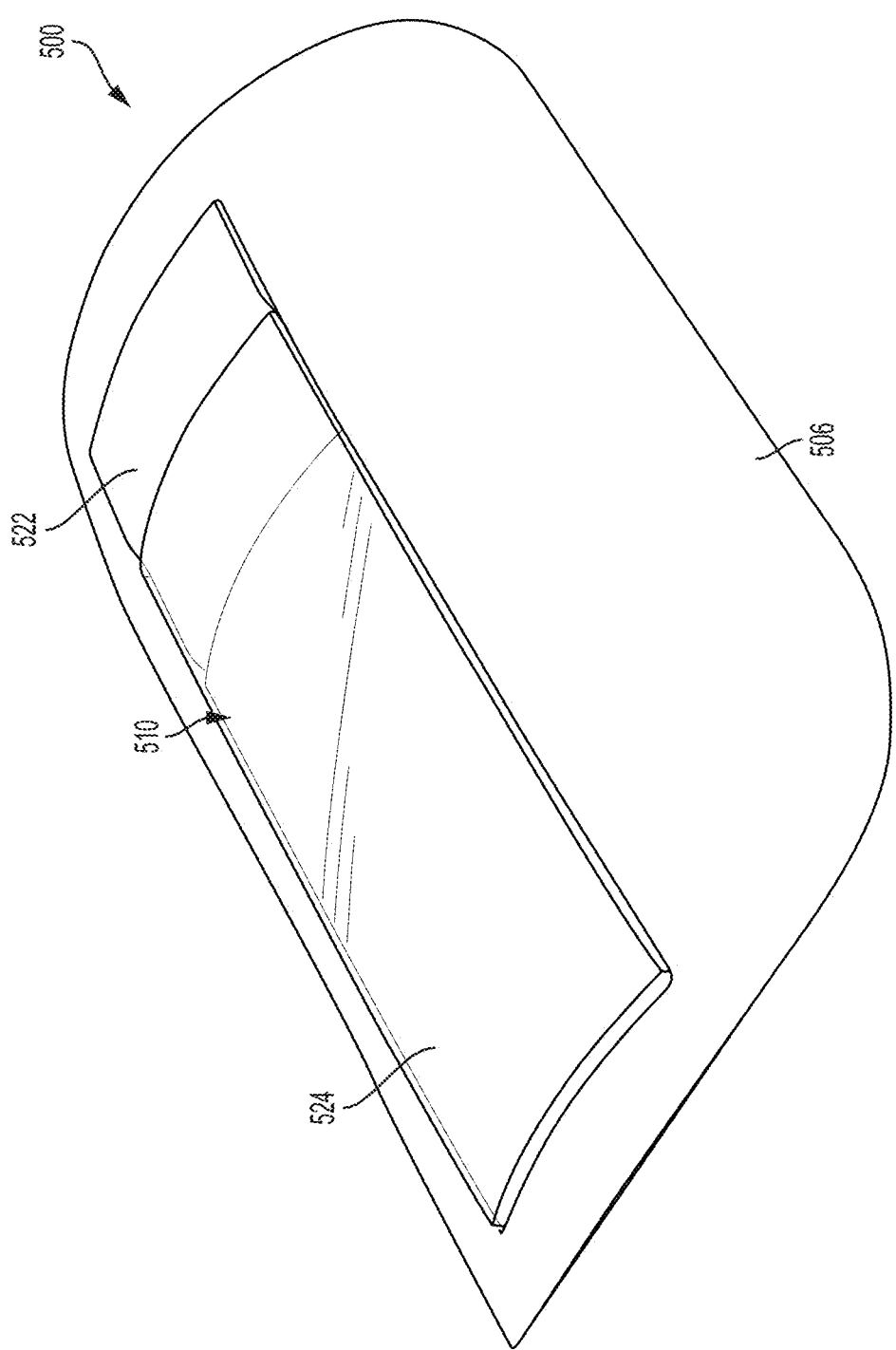
FIG. 8 shows a perspective view of an apparatus according to one embodiment of the present invention.

FIG. 8 shows a top, perspective view of an apparatus 500 with a test strip 510 comprising a sample pad-conjugate pad 522 and chromatographic membrane pad 524 in a cavity 514 of the first cassette structure 506. In some embodiments, the first cassette structure 506 may have an arcuate shape.

Figure 9:
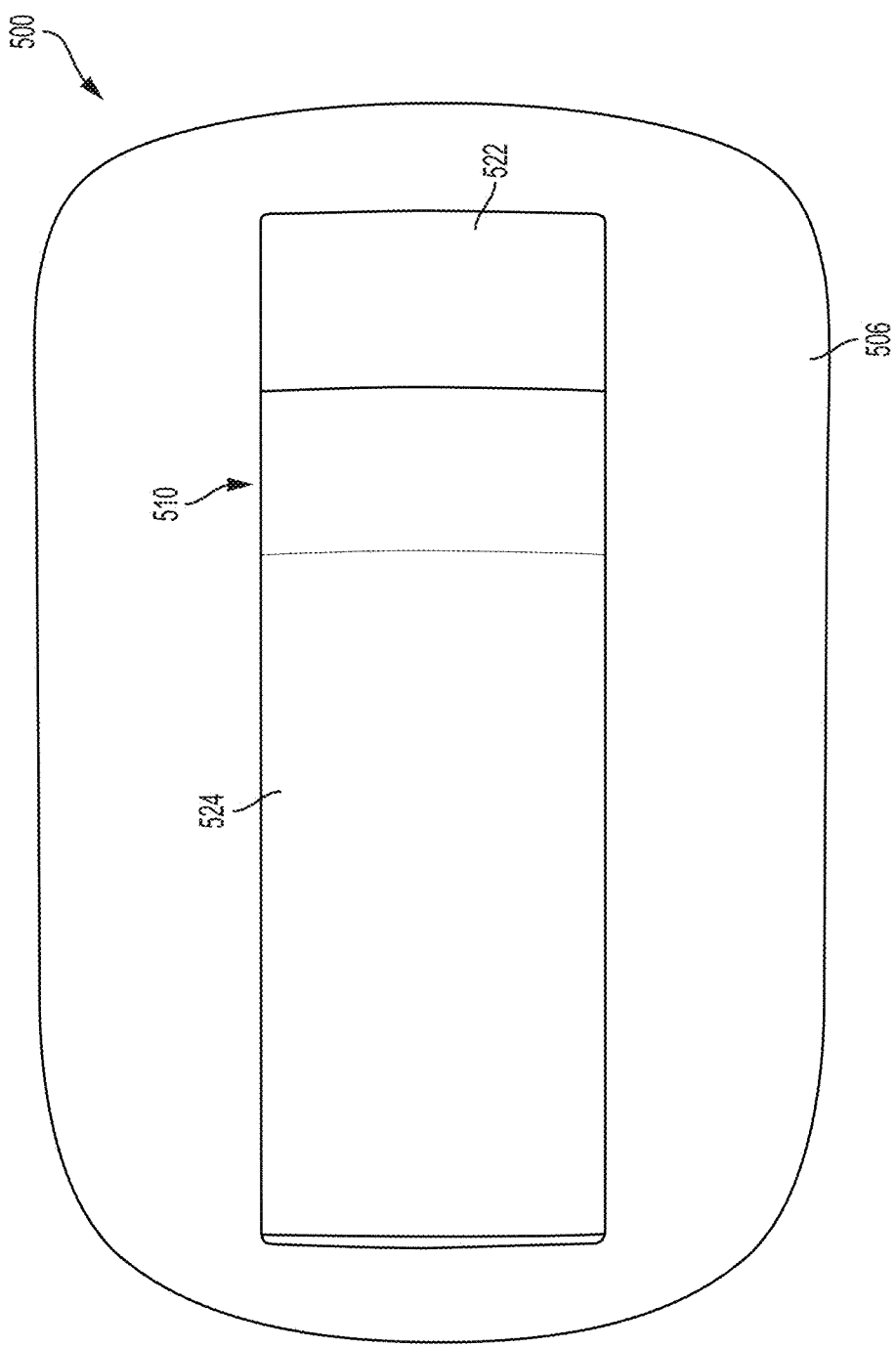
FIG. 9 shows a top view of an apparatus according to one embodiment of the present invention.

FIG. 9 shows a top view of an apparatus 500 with a test strip 510 comprising a sample pad-conjugate pad 522 and chromatographic membrane pad 524 in a cavity 514 of the first cassette structure 506. In some embodiments, the first cassette structure 506 may have an arcuate shape.

FIG. 10 shows a bottom, perspective view of an apparatus 500. In some embodiments, an adhesive strip 516 may be added to the center region 520 on the back side of the second cassette structure 508 to adhere the assembled apparatus 500 to a desired location for use. In some embodiments, the first cassette structure 506 may have an arcuate shape.

FIGS. 11A and 11B show an exploded view of an apparatus 500 according to one embodiment described herein. FIG. 11A shows an exploded view of the topside; FIG. 11B shows an exploded view of the underside. An absorbent pad/wick 504 is cut, formed and placed on the underside of a first cassette structure 506 partially encompassing a raised feature 518 in the first cassette structure 506 of the detection layer 502. In some embodiments, the first cassette structure 506 is arcuate shaped. The detection layer 502 is covered with a bottom layer, in some embodiments a second cassette 508. An Ultraviolet radiation curable adhesive is used on the surface of the first cassette 506 surrounding the absorbent pad 504 to couple the second cassette 508 to the first cassette structure 506 with UV radiation. Once cured, the absorbent pad 504 is coupled to the first cassette structure 506 and second cassette structure 508.

A top layer 512 may have an adhesive backing. In some embodiments, the top layer 512 includes an opening 526 and a window 528. Opening 526 of the top layer can provide an opening through which liquid or other medium can travel to the detection layer or detection subassembly for testing. The opening 526 generally overlaps the sample pad-conjugate pad 522 of the test strip 510. The opening 526 is generally circular, but other shapes of opening 526 can be included, for example, oval, rectangles, words, symbols, and emoticons can be used. Window 528 is in a rectangular shape, but other shapes of window 528 can be included in the top layer 512. Window 528 can be aligned with chromatographic membrane pad 524 of a detection layer 502 or detection subassembly such that when the test is complete, an indicator (not shown) can be visible to a user through the window 528. In FIGS. 11A and 11B one opening 526 is shown; in other embodiments, more than one opening can be included, for example, two three, four, five, six, or more openings. In some such embodiments, the size of the plurality of openings can be adjusted to a size sufficient to permit a liquid or other medium to travel to a detection layer or detection subassembly for testing and a size that minimize the aesthetic impact of the openings.

A test strip 510 comprising a sample pad-conjugate pad 522 and chromatographic membrane pad 524 is adhered to the underside of the top layer 512. The top layer 512 with connected test strip 510 is placed in a cavity 514 of the first cassette structure 506. The cavity 514 and the raised feature 518 are complementary features in the first cassette structure 506. An adhesive strip 516 may be added to the center region 520 on the back side of the second cassette structure 508 to adhere the assembled apparatus 500 to a desired location for use.

Figure 12A:
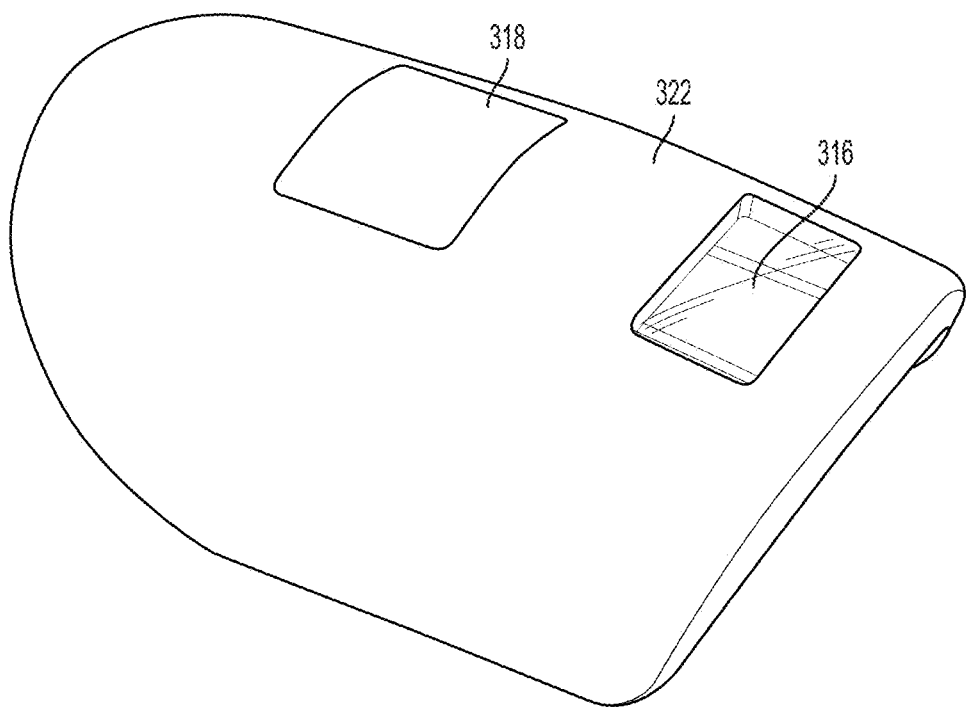
FIG. 12A shows a top layer and FIG. 12B shows a bottom layer.
Figure 12B:
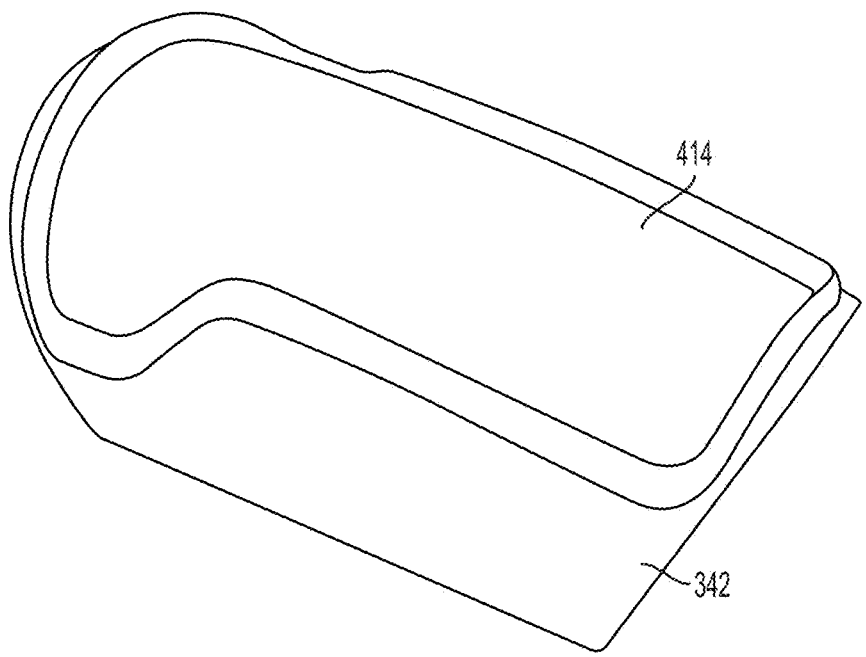

FIGS. 12A and 12B show top layer component 322 and bottom layer component 342 of an apparatus in an embodiment of the present invention in an exploded relationship. A detection layer (not shown) can be positioned on a top surface of the bottom layer 342. The bottom layer 342 includes a channel 414 that houses the detection layer 342. In some embodiments, the channel 414 is T-shaped and centered on the bottom layer 342. Opening 316 of the top layer 322 can provide an opening through which liquid or other medium can travel to the detection layer (not shown) or detection subassembly for testing. The opening 316 generally overlaps the detection layer. The opening 316 is generally rectangular, but other shapes of opening 316 can be included, for example, oval, circles, words, symbols, and emoticons can be used. The top layer 322 of the apparatus 312 may also include window 318 that allows viewing of an area beneath the top surface. Window 318 may be a void/opening, an aperture, a translucent solid or include optical properties e.g. a lens. In FIG. 12A, a window 318 is shown; in other embodiments, more than two openings can be included, for example, three, four, five, six, or more openings. Window 318 can be aligned with the detection layer or detection subassembly such that when the test is complete, an indicator (not shown) can be visible to a user through the window 318. In some embodiments, apparatus 312 may have an arcuate shape.

Figure 13A:
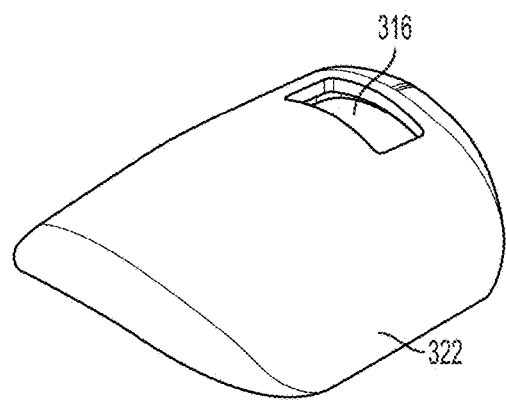
FIGS. 13A, 13B, 13C, and 13D show an apparatus according to one embodiment of the present invention.
Figure 13B:
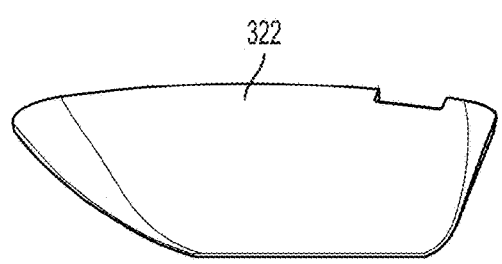
Figure 13C:
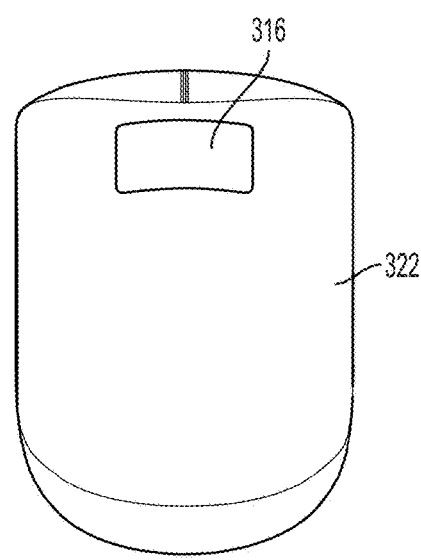
Figure 13D:
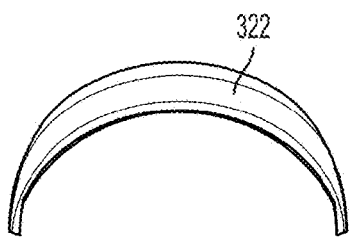

FIG. 13A shows a top layer component 322 of an apparatus 312 in an embodiment of the present invention. The top layer component 322 includes opening 316. FIGS. 13B, 13C and 13D show different perspectives of top layer component 322, with FIG. 13C being a top view. Opening 316 can provide an opening through which liquid or other medium can travel to the detection layer (not shown) for testing. The opening 316 generally overlaps the detection layer. In FIG. 13, opening 316 is in a rectangular shape, but other shapes of opening 316 can be included in the top layer 61. In some embodiments, apparatus may have an arcuate shape and may be thinner at the edge of the apparatus than in the center of the apparatus 312.

Figure 14B:
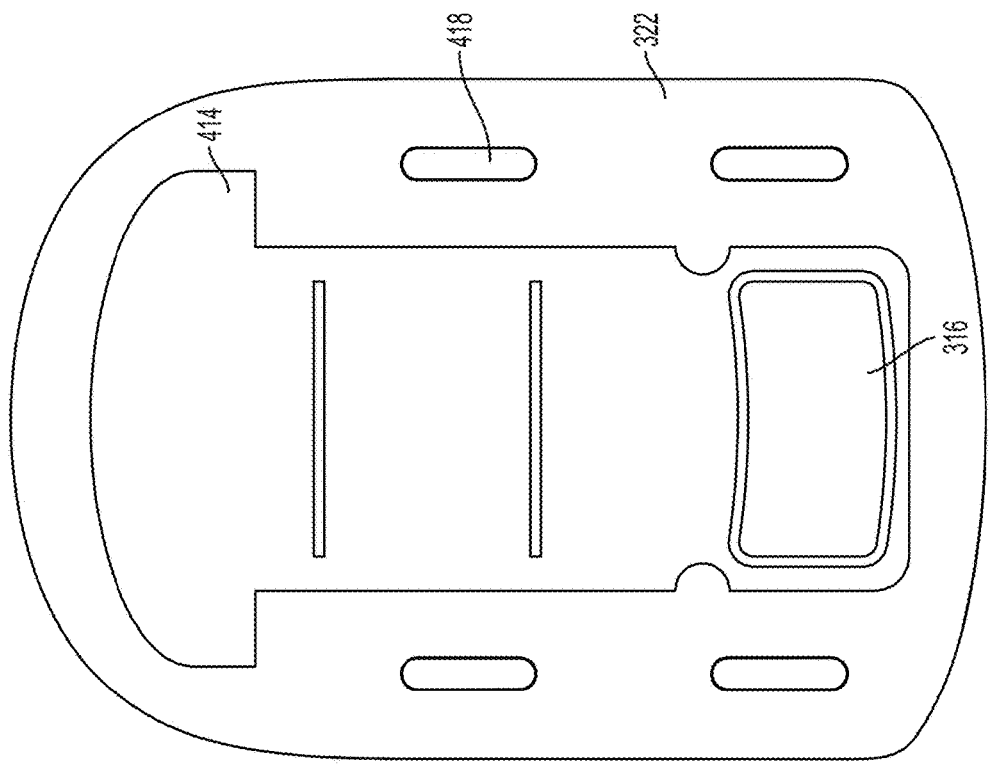
FIG. 14A and FIG. 14B show a top layer of an apparatus according to one embodiment of the present invention.
Figure 14A:
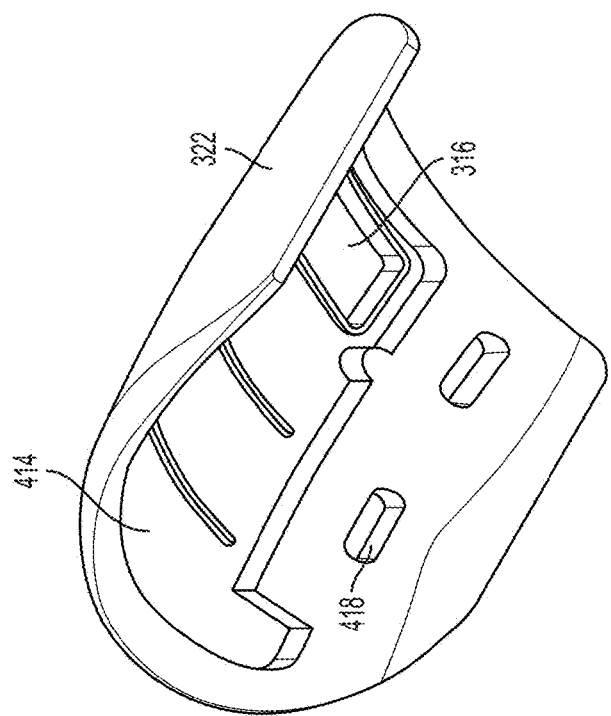

FIGS. 14A and 14B show the underside of a top layer component 322 of an apparatus 312 in an embodiment of the present invention. FIG. 14A is a perspective view and FIG. 14B is a top view of the underside. The underside of the top layer 322 may be configured with recessed areas to facilitate interconnection with other layers of the apparatus 312. A channel/series of grooves 414 is provided to allow a detection layer (not shown) to at least partially recess within the top layer 322. The channel 414 shaped matches the shape of the detection layer, in this embodiment, the channel 414 is T-shaped. Antistuds 418 are provided to mate with studs from other layers of the apparatus 312. In this embodiment, the anti-studs 418 are placed on either side of the channel 414 for the detection layer. The shape of the anti-stud 418 corresponds to the shape of the stud on the other layers of the apparatus 312. Opening 316 is shown at the edge of the top layer opposite of the widest portion of the channel 414.

Figure 15A:
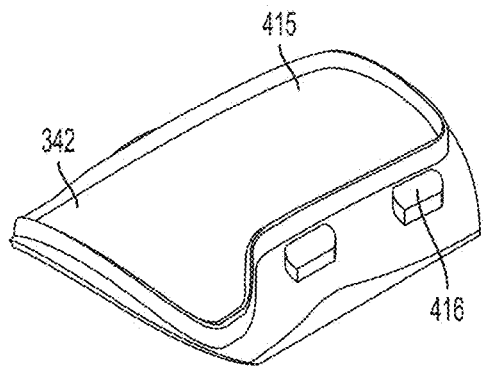
FIGS. 15A, 15B, 15C, and 15D show views of a bottom layer of an apparatus according to one embodiment of the present invention.
Figure 15B:
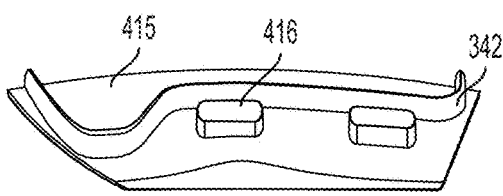
Figure 15C:
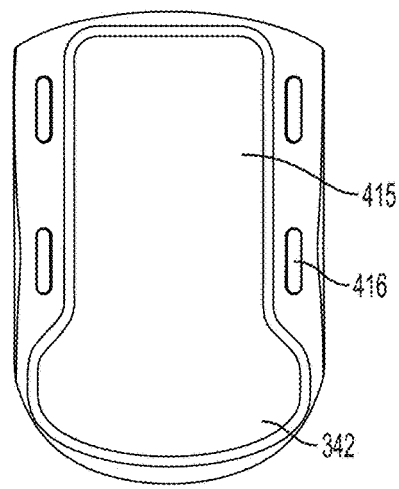
Figure 15D:
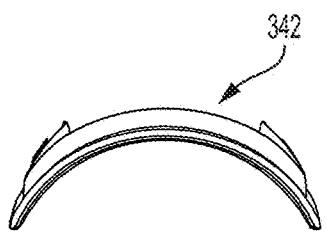

FIGS. 15A, 15B, 15C and 15D show a bottom layer component 342 of an apparatus in an embodiment of the present invention. FIG. 15B shows a side view, FIG. 15C shows a top view and FIG. 15D shows an alternative side view of a bottom layer component 342, respectively. As shown in the Figures, a bottom layer component 342 may include grooves, slots, cut-out areas and channels 415 and studs 416 to facilitate interconnection with other layers of the apparatus. In an embodiment, portions of the grooves, slots, cut-out areas and channels 415 on the top side of bottom layer component 342 correspond to portions of the grooves, slots, cut-out areas and channels 414 on the underneath side of top layer component 322. Similarly, portions of the anti-studs 418 on the top side of bottom layer component 342 correspond to portions of the studs 416 on the underneath side of top layer component 322. In some embodiments, the channel 415 may have a raised edge the may facilitate alignment of the detection layer within the apparatus 312. The underneath portion of bottom layer component 342 may be coupled with an adhesive to facilitate placement for use.

Figure 16B:
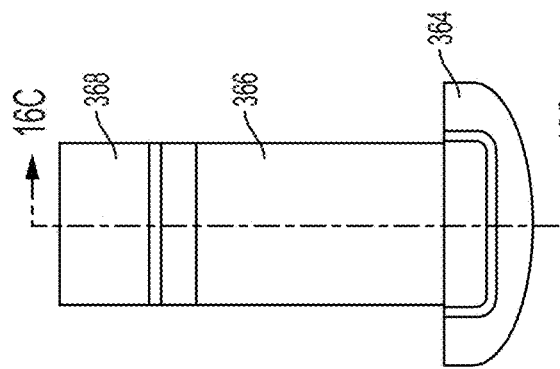
FIG. 16A, FIG. 16B, and FIG. 16C show a detection layer according to one embodiment of the present invention.
Figure 16A:
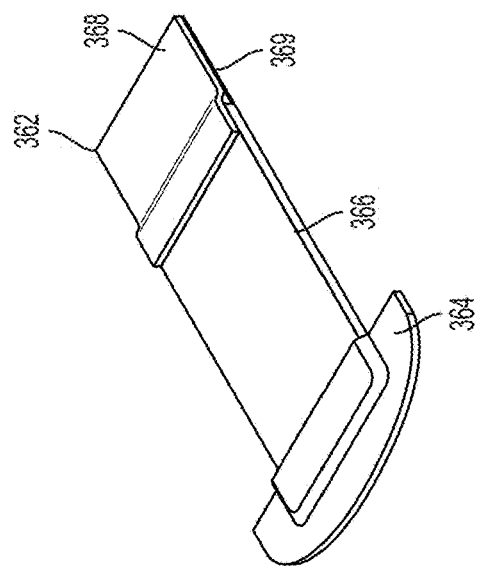
Figure 16C:
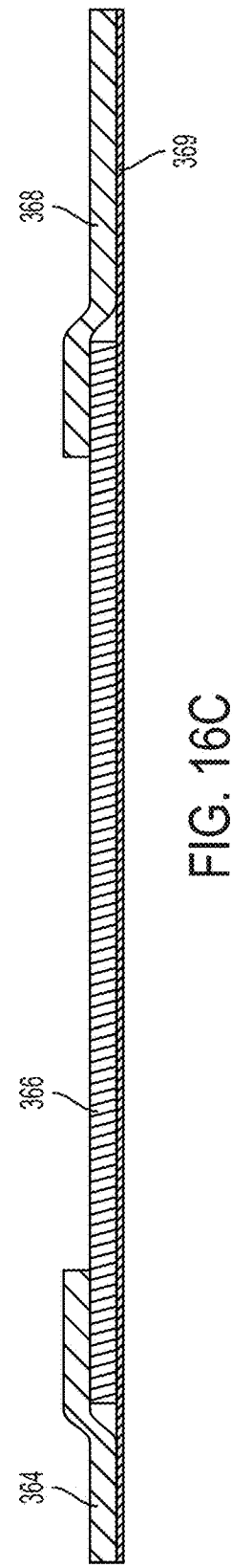

FIG. 16 shows detection layer that can be used in embodiments of apparatus described herein. FIG. 16A shows detection layer 362, with an absorbent pad 364 for facilitating receiving of a liquid. Detection layer 362 also includes chromatographic membrane 366 that allows for liquid migration, and a sample pad 368. A portion of the sample pad 368 overlaps the chromatographic membrane 366. Similarly, a portion of the absorbent pad 364 overlaps the chromatographic membrane 366. In some embodiments, the absorbent pad 364 may be wider than the chromatographic membrane 366 and sample pad 368, giving the detection layer a T-shaped appearance. As shown in FIG. 16C, the detection layer 362 may include a backing 369. FIG. 16B shows a top view of detection layer 362, and FIG. 16C shows a cross-sectional view of detection layer 362 along the line B-B in FIG. 16B.

Figure 17:
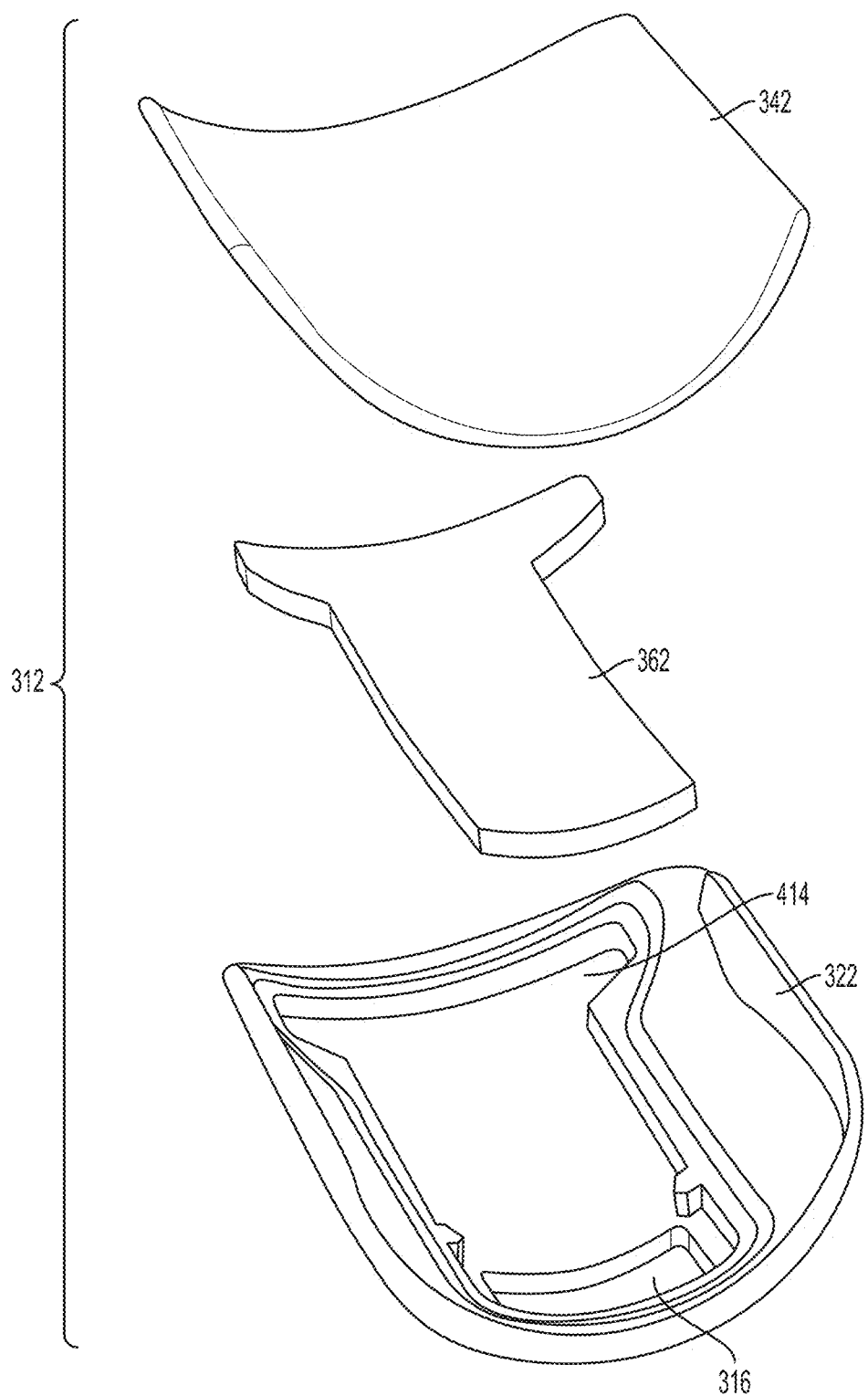
FIG. 17 shows an exploded view of a top layer, an detection layer, and a bottom layer of an apparatus according to one embodiment of the present invention.

FIG. 17 shows a bottom view of bottom layer component 342, detection layer 362, and the underneath of top layer component 322 in exploded view. In some examples, a detection layer can be an assay system. The channel 414 in the top layer permit alignment and coupling of the detection layer 362. The opening 316 can provide an opening through which liquid or other medium can travel to the detection layer 362 for testing.

Figure 18B:
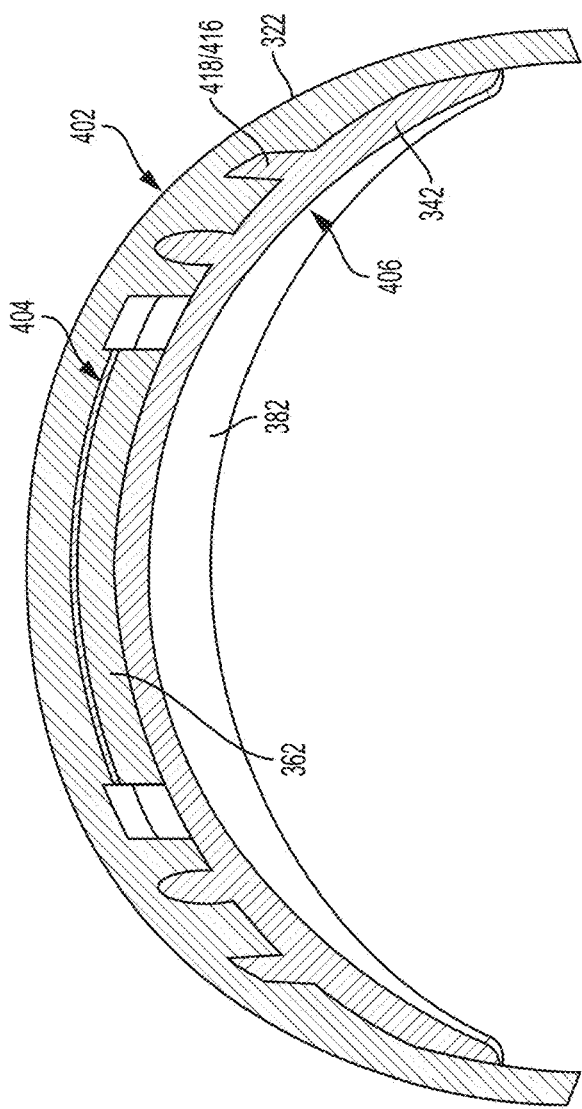
FIGS. 18A, 18B, and 18C show views of an embodiment of an apparatus according to one embodiment of the present invention.
Figure 18C:
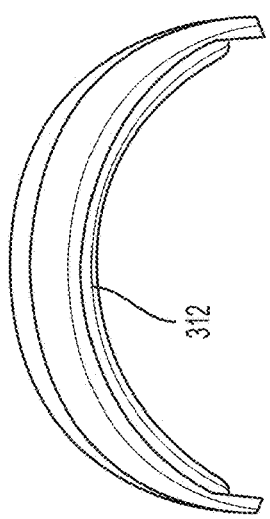
Figure 18A:
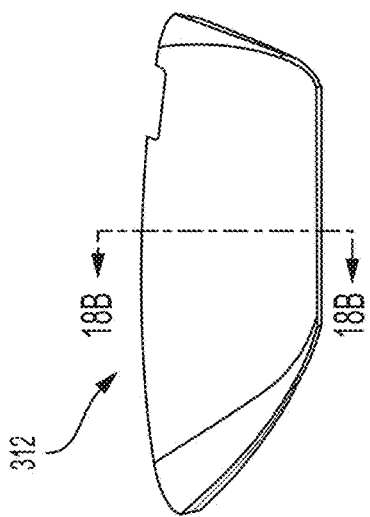

FIGS. 18A, 18B, and 18C show views of an apparatus 312, with a plurality of layers comprising a top layer component 322, detection layer 362, a bottom layer component 342 and further comprising an adhesive layer 382. FIG. 18A shows a side view of apparatus 312. FIG. 18B shows a cross-sectional view along the line A-A in FIG. 18A, that shows the relationships among the layers. FIG. 18C shows a front on view of apparatus 312. The shell top 402, shell bottom 406, and test strip assembly 404 are shown in FIG. 18B. The relationship of the studs 416 and anti-studs 418 are shown in the connected/mated top layer 322 and bottom layer 342. In some embodiments, the apparatus 312 may be thinner at the edges of the apparatus 312 as the layers decrease.

Figure 19:
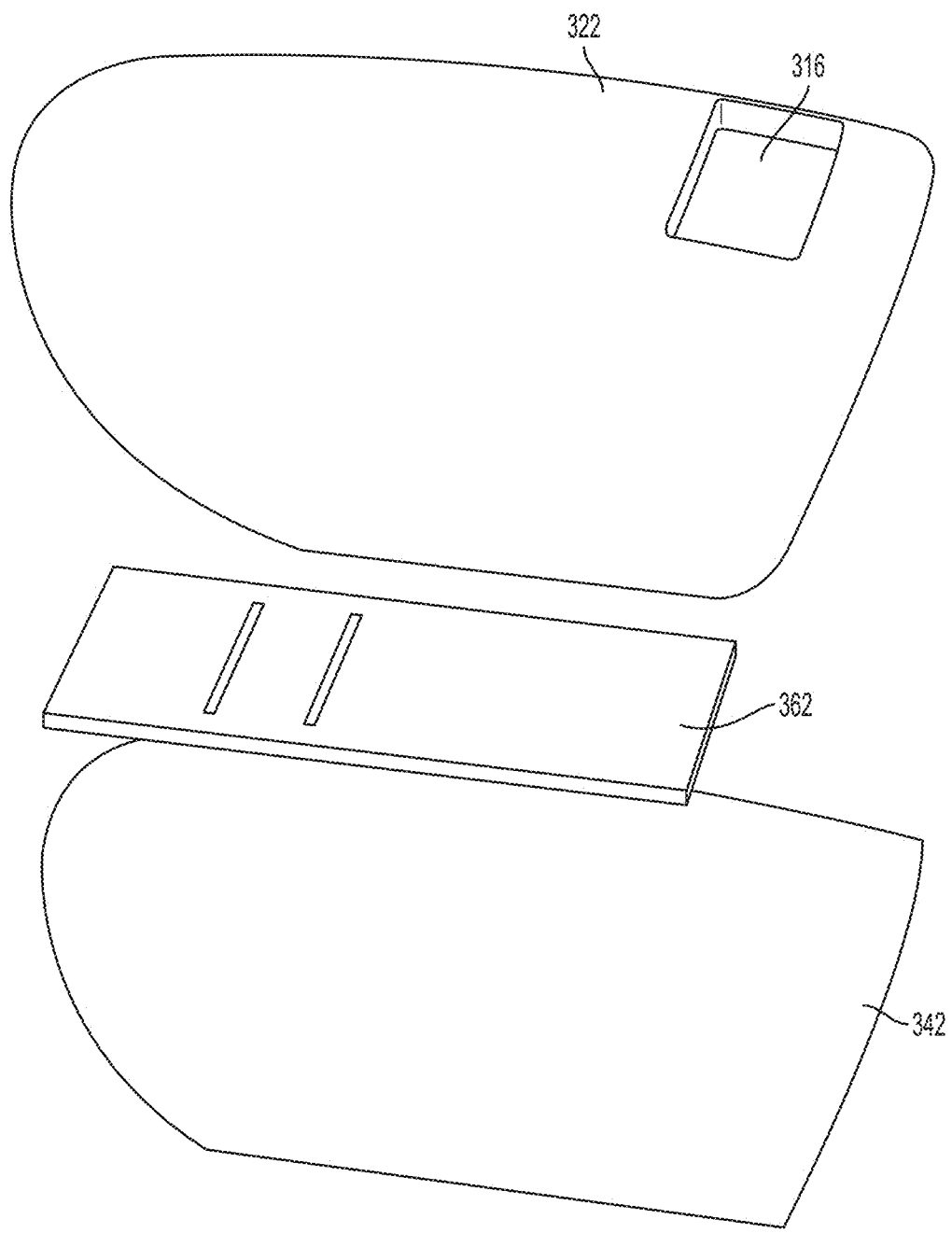
FIG. 19 shows an embodiment of an apparatus according to one embodiment of the present invention.

FIG. 19 shows top layer component 322, detection layer 362, and bottom layer component 342 of an apparatus in an embodiment of the present invention in an exploded relationship. Opening 316 can provide an opening through which liquid or other medium can travel to the detection layer 362 for testing. The opening 316 generally overlaps the detection layer 362. In some embodiments, the apparatus may have an arcuate shape.

Figure 20:
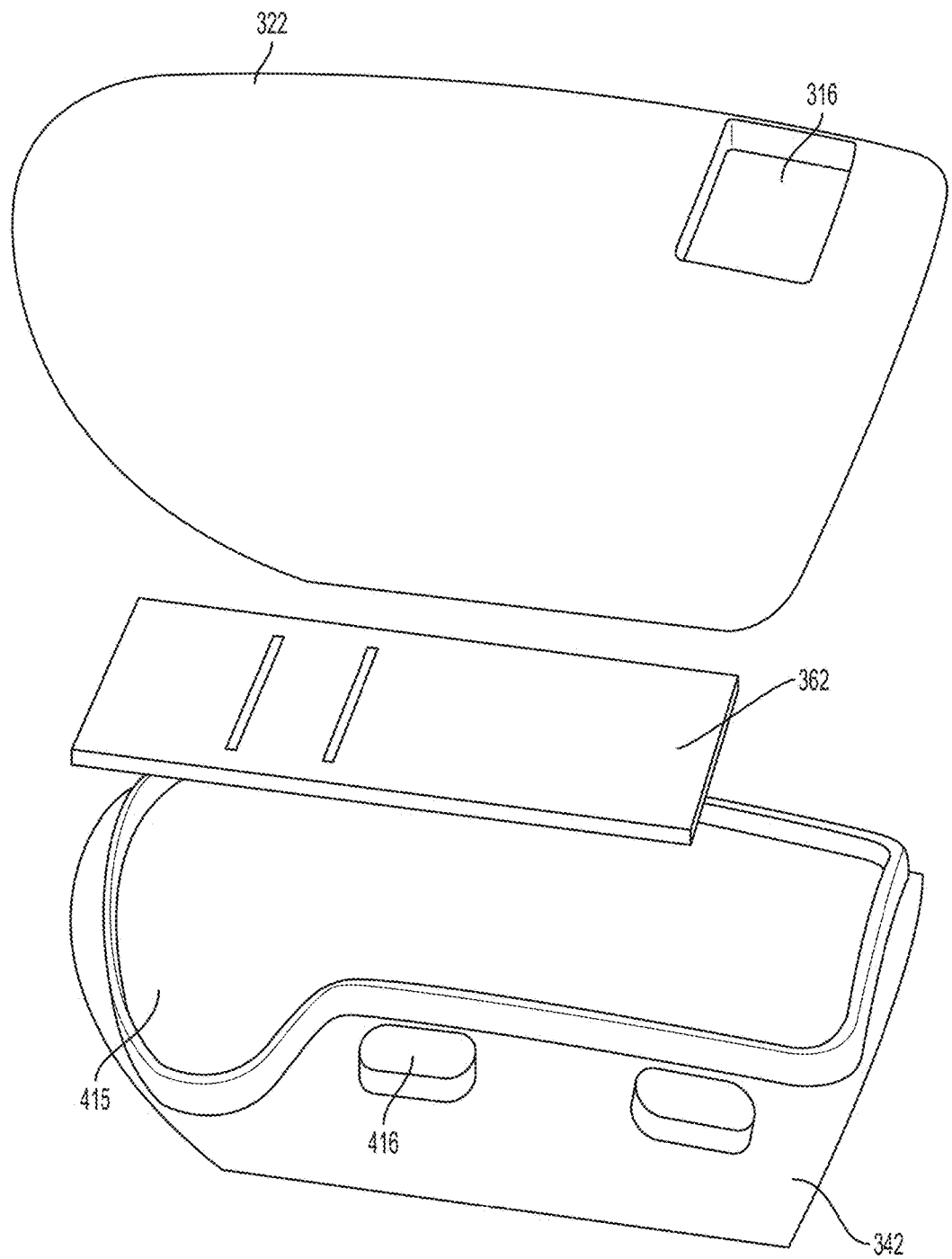
FIG. 20 shows an embodiment of an apparatus according to one embodiment of the present invention.

FIG. 20 shows top layer component 322, detection layer 362, and bottom layer component 342 of an apparatus in an embodiment of the present invention in an exploded relationship. In some embodiments, the detection layer 362 is rectangular in shape. As shown in the figure, a bottom layer component 342 may include grooves, slots, cut-out areas and channels 415 and studs 416 to facilitate interconnection with other layers of an apparatus and use of an assay. In an embodiment, portions of the grooves, slots, cut-out areas and channels 415 on the top side of bottom layer component 342 correspond to portions of the grooves, slots, cut-out areas and channels 414 on the underneath side of top layer component 322. The underneath portion of bottom layer component 342 may communicate with an adhesive to facilitate placement for use.

Figure 21:
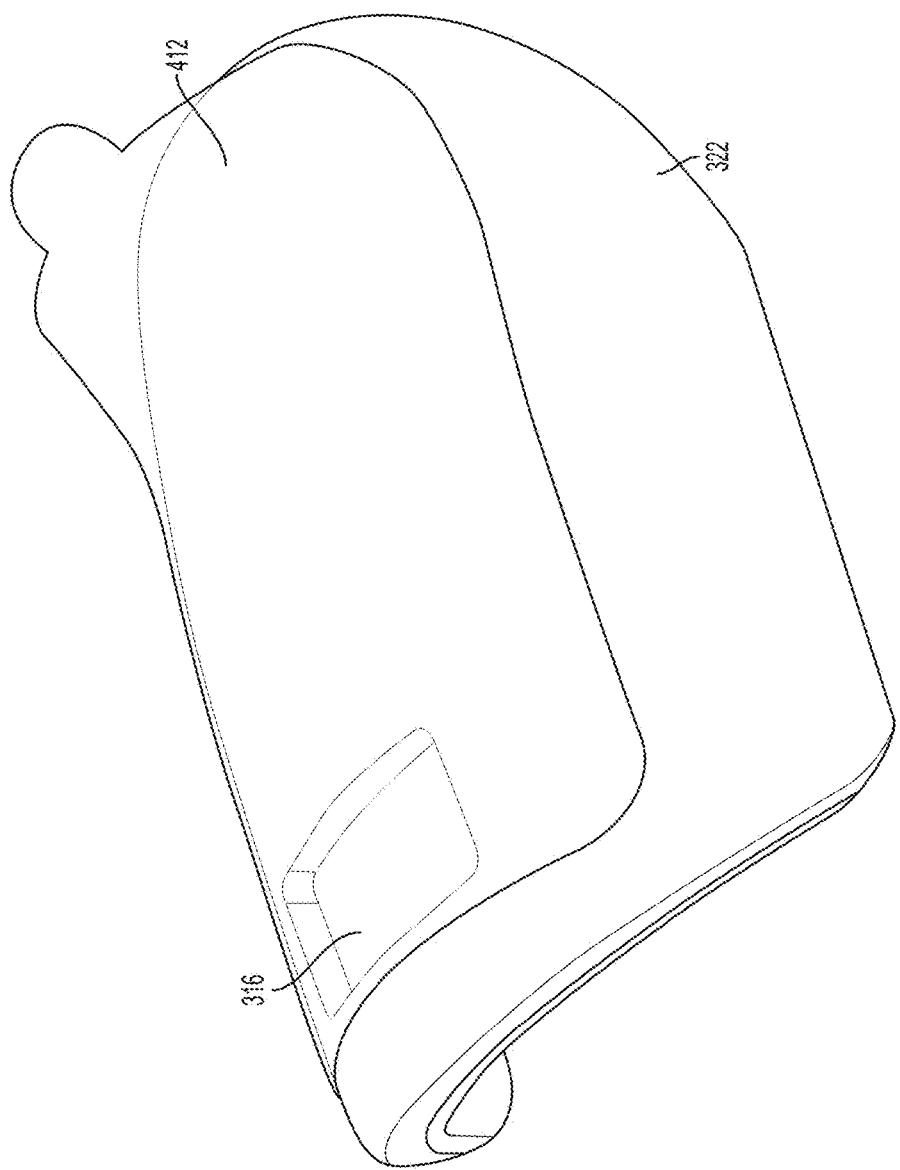
FIG. 21 shows an embodiment of an apparatus according to one embodiment of the present invention.

FIG. 21 shows top layer component 322 covered with protective layer 412. Protective layer 412 may be transparent or opaque, and in some cases may match the color or top layer component 322. This protective layer may also have decorative patterns, symbols, logos, or other designs. The shape of the protective layer 412 is substantially similar to the top layer 322 and may be arcuate, as in this embodiment.

Figure 22:
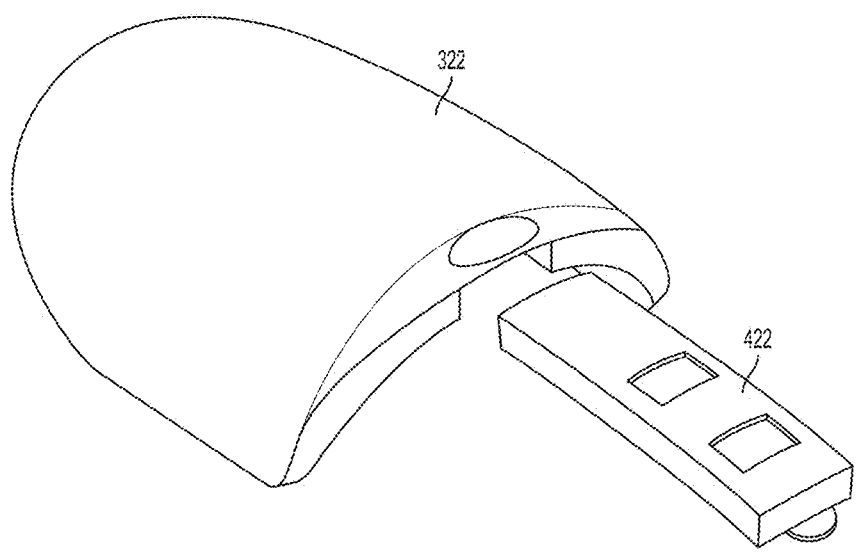
FIG. 22 shows an embodiment of an apparatus comprising an assay cartridge according to one embodiment of the present invention.

FIG. 22 shows top layer component 322, which may contain a channel 414 for receiving cartridge 422. In some embodiments, the detection layer 362 may be in cartridge form. In an embodiment, top layer component 322 is reusable, while cartridge 422 is disposable. Test cartridge 422 may contain test strip 404 as described herein.

Figure 23A:
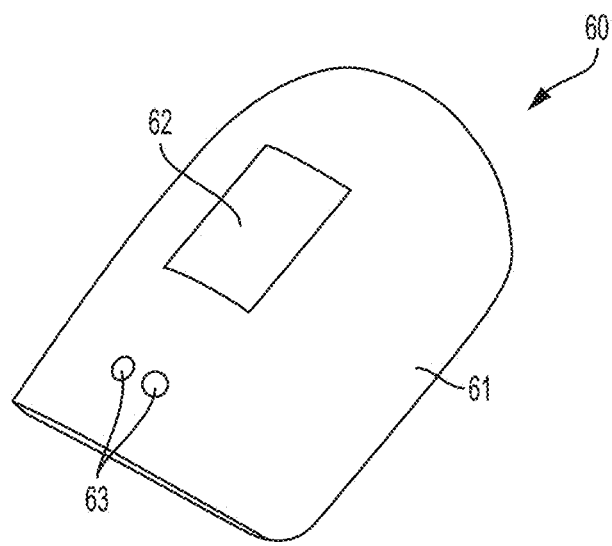
FIGS. 23A and 23B show an apparatus according to one embodiment of the present invention.
Figure 23B:
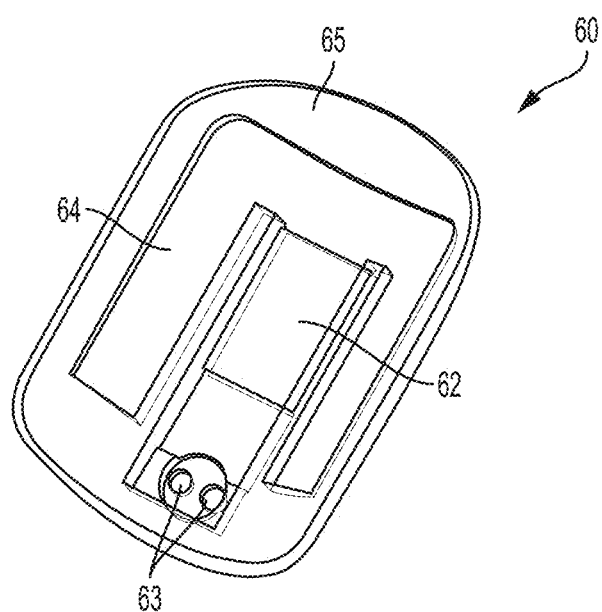

FIGS. 23A and 23B show another apparatus that can be used according to embodiments described herein. FIG. 23A shows apparatus 60 from a top perspective view having a top layer 61. The top layer 61 can be include features of the top layer described herein. In some embodiments, the top layer 61 can be a decorative layer. In some embodiments, an optional peelable layer (not shown) may be adhered to the top side of the top layer 61. The top layer 61 includes an window 62 and two openings 63. Window 62 is in a rectangular shape, but other shapes of window 62 can be included in the top layer 61. Window 62 can be aligned with a detection layer or detection subassembly such that when the test is complete, an indicator (not shown) can be visible to a user through the window 62. Openings 63 of the top layer can provide an opening through which liquid or other medium can travel to the detection layer or detection subassembly for testing. The openings 63 are generally circular, but other shapes of openings 63 can be included, for example, oval, rectangles, words, symbols, and emoticons can be used.

In FIG. 23A two openings 63 are shown; in other embodiments, more than two openings can be included, for example, three, four, five, six, or more openings. In some such embodiments, the size of the plurality of openings can be adjusted to a size sufficient to permit a liquid or other medium to travel to a detection layer or detection subassembly for testing and a size that minimize the aesthetic impact of the openings. In the embodiment shown in FIG. 23A and FIG. 23B, the detection subassembly is not shown.

FIG. 23B shows apparatus 60 from a bottom perspective view, that is the side of the apparatus that is position proximate to the user. The apparatus 60 includes substrate 65 where the detection subassembly (not shown) can be positioned, for example in a channel 64. Other configurations of the substrate 65 and channel 64 can be utilized. Although not shown, a bottom layer or film can be placed on the apparatus 60 that can be positioned on a user, for example, on a user's fingernail. The openings 63 provide a channel through which the liquid or other medium can travel to from the top layer (i.e., the layer exposed to the environment) to a detection layer or a detection subassembly, for example, to a sample pad of a detection subassembly.

Figure 24A:
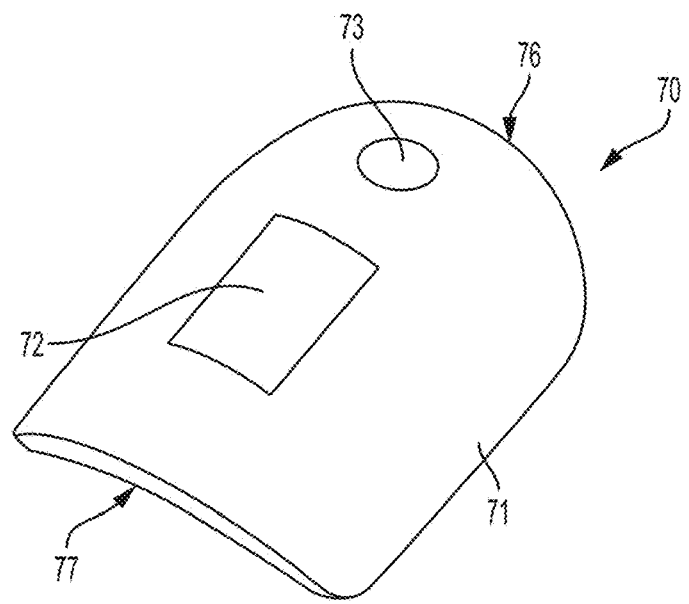
FIGS. 24A and 24B show an apparatus according to one embodiment of the present invention.
Figure 24B:
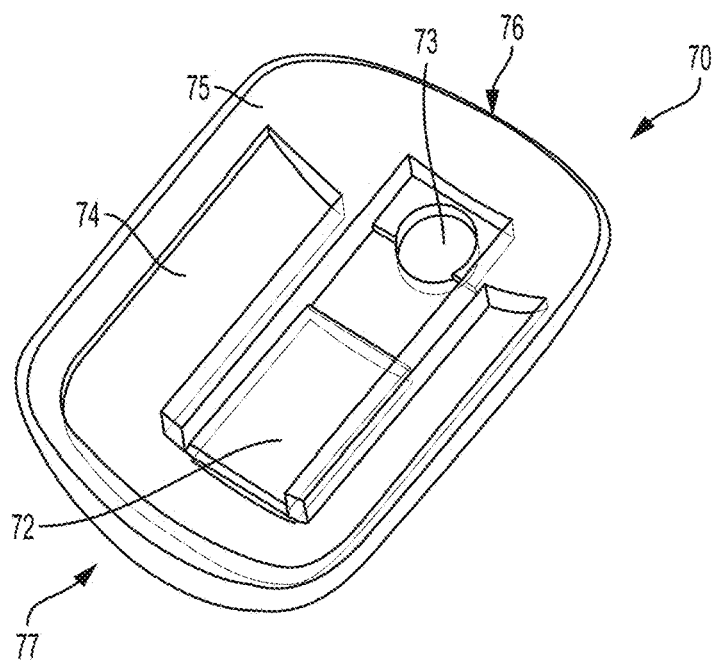

FIGS. 24A and 24B show another apparatus that can be used according to embodiments described herein. FIG. 24A shows apparatus 70 from a top perspective view having a top layer 71. The apparatus has a first end 76 and a second end 77. In some embodiments, when positioned on a user, the first end 76 is positioned proximate to a user's cuticle, and the second end 77 is positioned distal to a user's cuticle. The top layer 71 can be include features of the top layer described herein. In some embodiments, the top layer 71 can be a decorative layer. In some embodiments, an optional peelable layer (not shown) may be adhered to the top side of the top layer 71. The top layer 71 includes an window 72 and opening 73. In the embodiment shown in FIGS. 24A and 24B, when positioned on a user's fingernail, the opening 73 is positioned at a first end 76 proximate to a user's cuticle. In some such embodiments, the opening 73 being positioned near the cuticle can facilitate flow of the liquid into the apparatus in order to be tested. For example, when a user places her finger into a beverage, the second end 77 of the apparatus 70 is positioned in below the first end 76. As the fingernail in which the apparatus 60 is applied is submerged in the beverage, the liquid can enter into the opening 73 while also permitting any gas within a detection subassembly, for example in a cavity or channel, to escape and not be trapped in the detection subassembly.

Window 72 is in a rectangular shape, but other shapes of window 72 can be included in the top layer 71. Window 72 can be aligned with a detection layer or detection subassembly such that when the test is complete, an indicator (not shown) can be visible to a user through the window 72. Opening 73 of the top layer can provide an opening through which liquid or other medium can travel to the detection layer or detection subassembly for testing. The opening 73 is generally circular, but other shapes of opening 73 can be included, for example, oval, rectangles, words, symbols, and emoticons can be used.

In FIG. 24A a single opening 73 is shown; in other embodiments, more than one opening can be included, for example, two, three, four, five, six, or more openings. In some such embodiments, the size of the opening can be adjusted to a size sufficient to permit a liquid or other medium to travel to a detection layer or detection subassembly for testing and a size that minimize the aesthetic impact of the openings. In the embodiment shown in FIG. 24A and FIG. 24B, the detection subassembly is not shown.

FIG. 24B shows apparatus 70 from a bottom perspective view, that is the side of the apparatus that is position proximate to the user. The apparatus 70 includes substrate 75 where the detection subassembly (not shown) can be positioned, for example in a channel 74. Other configurations of the substrate 75 and channel 74 can be utilized. Although not shown, a bottom layer or film can be placed on the apparatus 70 that can be positioned on a user, for example, on a user's fingernail. The opening 73 provides a channel through which the liquid or other medium can travel from the top layer (i.e., the layer exposed to the environment) to a detection layer or a detection subassembly, for example, to a sample pad of a detection subassembly.

Figure 25:
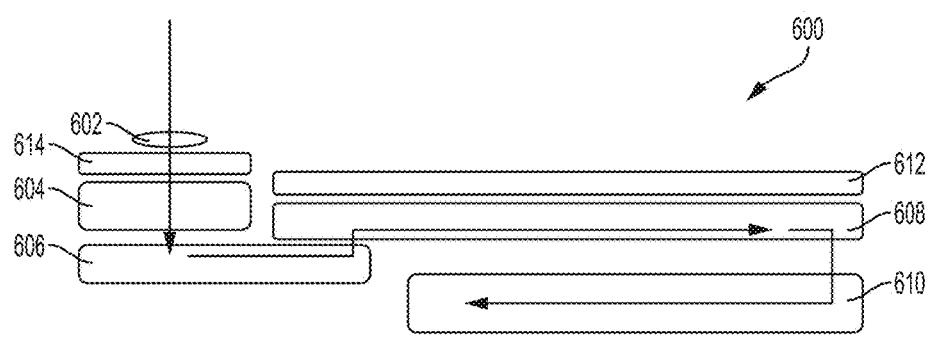
FIG. 25 shows a cross sectional view of the detection layer and the direction of flow of a liquid through the detection layer according to one embodiment of the present invention.

FIG. 25 shows a cross sectional view of the detection layer and the general direction of flow of a liquid medium through the detection layer 600. The liquid enters the detection layer through opening/sample port 602. The liquid flows from the opening to the sample pad 604, through the sample pad 604 to the conjugate pad 606, through the conjugate pad 606 to the chromatographic membrane pad 608, through the chromatographic membrane pad 608 to the absorbent pad 610, and finally diffuses within the absorbent pad 610. As shown in FIG. 25, the transitions to the subsequent pad in the flow path may be vertical, such as the flow from the conjugate pad 606 to the chromatographic membrane pad 608 and the chromatographic membrane pad 608 to the absorbent pad 610.

In FIG. 25, the configuration of the pads may also result in the flow path being counter-current in a portion of the detection layer as compared to the flow on a previous or subsequent pad of the detection layer. For example, the liquid in the absorbent pad/wick 610 flows counter-current to the direction of liquid flow in the chromatographic membrane pad 608. This configuration of the detection layer may allow for the overall length of the detection layer to be substantially less than a conventional detection layer that maintains a single flow path throughout the detection layer. This configuration allows for the overall length of the detection layer to be significantly reduced without reducing the overall flow path of the liquid. Thus, the configuration may achieve a detection layer in which the flow path of the liquid is longer than the overall length of the detection layer. In some examples, the length of the flow path may by two or three times the length of the detection layer. The optional untreated pad 614 may significantly reduce back flow through the opening 602 once the untreated pad 614 becomes fully saturated.

Figure 26:
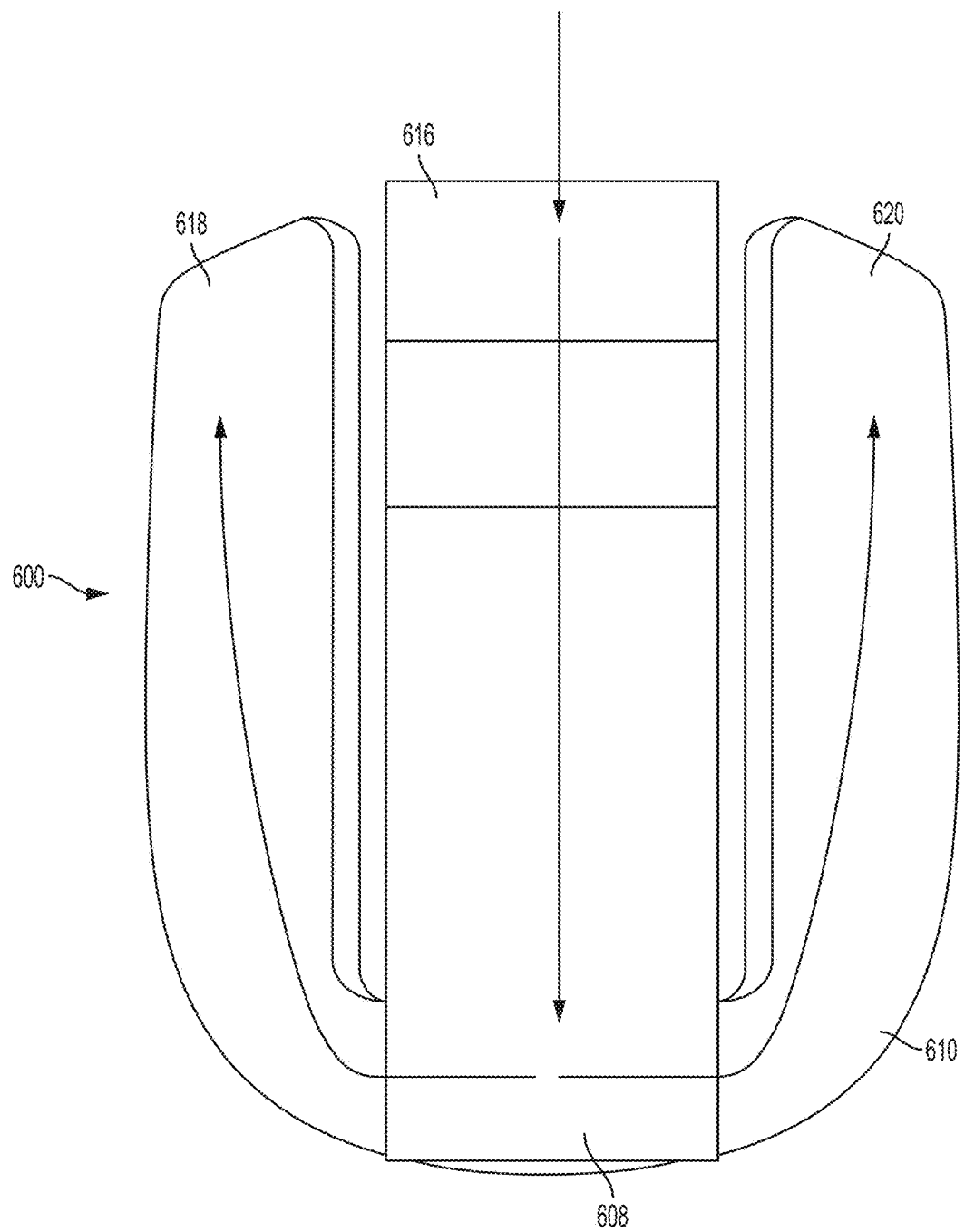
FIG. 26 shows the top view of the detection layer and the direction of flow of a liquid through the detection layer according to one embodiment of the present invention.

FIG. 26 shows the top view of the detection layer and the direction of flow of a liquid through the detection layer 600. The liquid enters the detection later and flows to the sample pad-conjugate pad 616, through the sample pad-conjugate pad 616 to the chromatographic membrane pad 608, through the chromatographic membrane pad 608 to the absorbent pad 610, and finally diffuses in the absorbent pad 610. As shown in FIG. 26, a flow path may be curved, such as the flow through the absorbent pad 610. Where the absorbent pad 610 is substantially U-shaped, the flow path of the liquid may be curved to substantially match the U-shaped of the absorbent pad 610. Furthermore, the flow direction of the liquid through the absorbent pad 610 may be counter-current to the flow direction of the liquid through the chromatographic membrane pad 608. In FIG. 26, the flow of liquid from the chromatographic membrane pad 608 splits when transitioning to the absorbent pad 610 with a portion of the liquid flowing to the proximal end of the absorbent pad 618 and a portion of the liquid flowing to the distal end of the absorbent pad 620.

Figure 27:
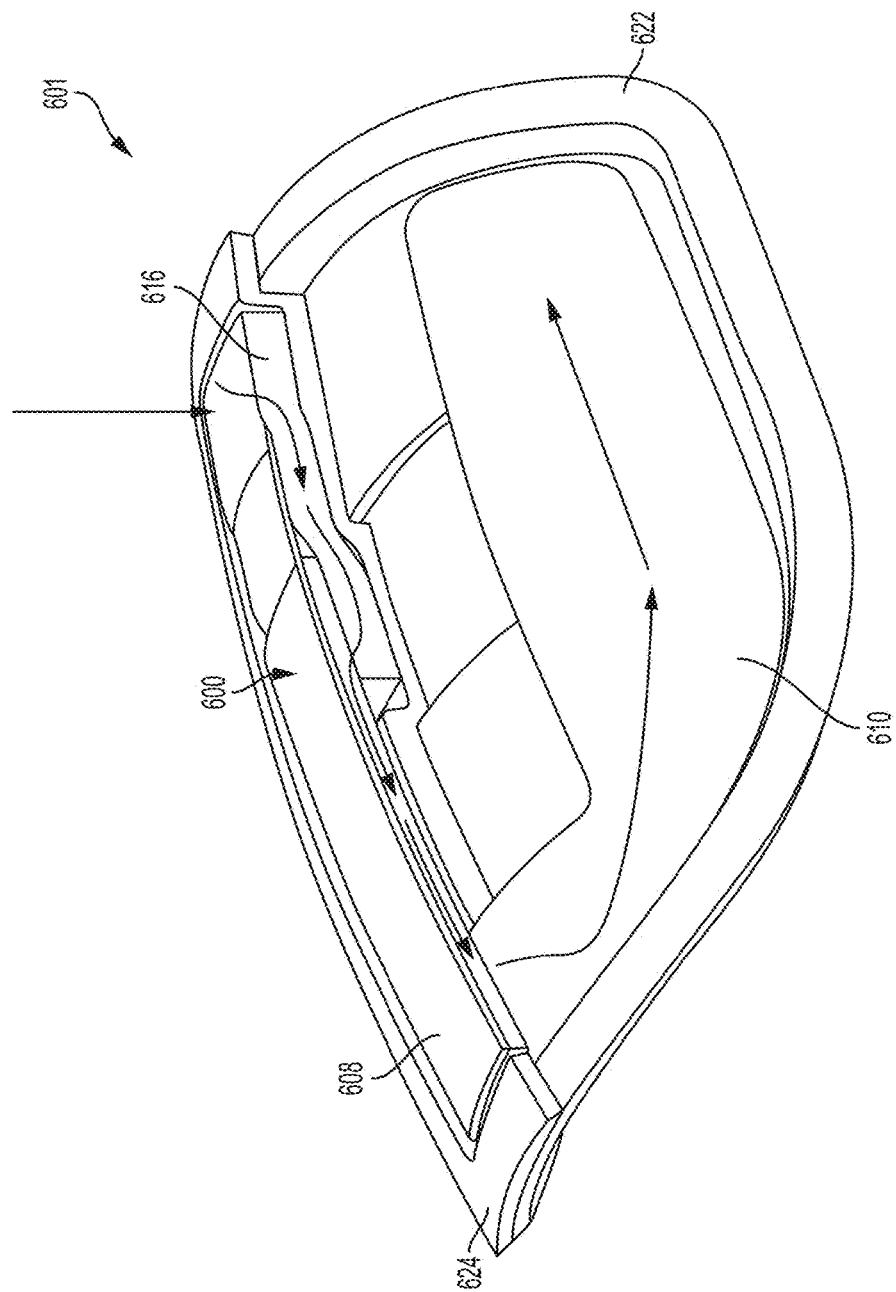
FIG. 27 shows cut away perspective view of the apparatus and the direction of flow of a liquid through the apparatus according to one embodiment of the present invention.

FIG. 27 shows cut away perspective view of the apparatus 601 and the direction of flow of a liquid through the apparatus 601. The liquid enters the detection layer 600 through opening 602 (not shown). The liquid flows down to the sample pad-conjugate pad 616, through the sample pad-conjugate pad 616, up to chromatographic membrane pad 608, through the chromatographic membrane pad 608, down to absorbent pad 610, and diffuses through the absorbent pad 610. In FIG. 27, the flow path may be curved, as seen in the absorbent pad 610. Where the absorbent pad 610 is substantially U-shaped, the flow path of the liquid may be curved to substantially match the U-shaped of the absorbent pad. Furthermore, the flow direction of the liquid in the absorbent pad 610 may be counter-current to the flow direction of the liquid in the chromatographic membrane pad 608. In some cases, the flow of liquid in the absorbent pad 610 may be substantially parallel to the flow of liquid in the chromatographic membrane pad 608.

Figure 28:
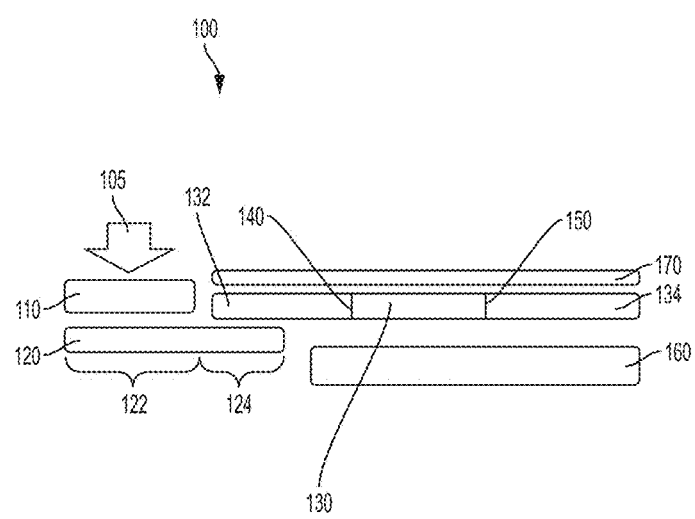
FIG. 28 shows an exploded cross-sectional view of the detection layer according to one embodiment of the present invention.

FIG. 28 is an exploded cross-section view of an apparatus 100 according to one embodiment described herein. Apparatus 100 comprises a sample pad 110, a conjugate pad 120, a detection layer 130 and an absorption pad or wick 160. The sample pad 110 is adjacent to a first portion 122 of the conjugate pad 120 so that in use a liquid is absorbed into the conjugate pad 120 from the sample pad 110. A second portion 124 of the conjugate pad is adjacent to the chromatographic membrane 130 at a proximal end 132 of the chromatographic membrane 130 so that in use a liquid is absorbed into the chromatographic membrane at the proximal end 132 and moves through the chromatographic membrane toward the distal end 134 of the chromatographic membrane 130. Between the proximal and distal ends the chromatographic membrane includes at least one test line 140 where an analyte-conjugated protein is deposited and at least one control line 150 where an anti-species antibody is deposited. The apparatus also comprises an absorption pad or wick 160 adjacent to the chromatographic membrane 130 so that in use liquid is absorbed into the wick from the chromatographic membrane 130. In some embodiments multiple test lines may be present to test for a plurality of targeted substances. Optionally, the apparatus may have a clear cover layer 170.

The design of the apparatus is not limited by the designs described in the Figures. The system may be produced by any technique known in the art.

In other embodiments, a method of making an apparatus is described herein. In some embodiments, the method of making an apparatus comprises providing a detection layer configured to detect the presence of a targeted substance; coupling a top layer to a top surface of the detection layer; and coupling a bottom layer to a bottom surface of the detection. In some embodiments, the method of making also includes coupling a removable layer to the top layer. In some embodiments, the strength of the coupling of the removable layer to the top layer may be less than the strength of the coupling of the top layer to the detection layer.

Turning to FIG. 11, the method of making an apparatus 500 for detecting the presence of a targeted substance comprises preparing a detection layer 502 by cutting, forming, and placing an absorbent pad/wick 504 on the underside of a first cassette structure 506. An Ultraviolet radiation curable adhesive is applied to the surface of the first cassette 506 surrounding the absorbent pad 504. The detection layer 502 is covered with a bottom layer by placing a second cassette 508 on the UV adhesive. The second cassette 508 is coupled to the first cassette structure 506 with UV radiation. Once cured, the absorbent pad 504 is coupled to the first cassette structure 506 and second cassette structure 508. The preparation of the detection layer 502 continues by adhering a test strip 510 to the underside of a top layer 512 and placing the top layer 512 with attached test strip 510 within a designed cavity 514 of the topside of the first cassette 506. An adhesive strip 516 may be added to adhere the apparatus 500 to the desired location for use.

The method for making the apparatus may further comprise applying a marker composition. Optionally, the method for making the apparatus may include applying the marker composition to more than one locations of the matrix. For example, the marker composition can be applied to two locations of the matrix, three locations of the matrix, four locations of matrix, five locations of the matrix, six locations of the matrix, seven locations of the matrix, eight locations of the matrix, nine locations of the matrix, or ten locations of the matrix.

The method of making the matrix can further include drying the marker composition on the matrix. Optionally, the humidity conditions for the drying step can be between 30% and 70% relative humidity (e.g., between 40% and 50% relative humidity). The marker composition can be dried on the matrix by allowing the composition to dry at room temperature. Optionally, the composition can be dried on the matrix by heating the composition to an elevated temperature. The temperature for drying the matrix can be from about 30° C. to about 100° C. (e.g., from about 40° C. to about 90° C., from about 50° C. to about 80° C., or from about 60° C. to about 70° C.). For example, the temperature for drying the matrix can be about 90° C. or lower, 80° C. or lower, 70° C. or lower, 60° C. or lower, 50° C. or lower, 40° C. or lower, or 30° C. or lower.

The composition may be dried on the matrix for a period of time ranging from five seconds to several hours. For example, the composition can be dried on the matrix for a period of time of 5 seconds, 10 seconds, 20 seconds, 30 seconds, 40 seconds, 50 seconds, 1 minute, 2 minutes, 3 minutes, 4 minutes, 5 minutes, 10 minutes, 15 minutes, 30 minutes, 1 hour, 2, hours, 3 hours, 4 hours, or 5 hours.

In yet further embodiments, a method of using an apparatus to detect a targeted substance is described herein. In some embodiments, the method of using comprises providing an apparatus described herein, exposing a portion of the apparatus to a medium, and observing an indication to determine the presence or absence of the targeted substance. In some embodiments, the method of using comprises removing a removable layer from the apparatus to expose at least a portion of the detection layer. In some embodiments, the method of using comprises observing a visual indication. In some embodiments, the method of using comprises exposing an apparatus to a liquid medium. In some embodiments, the method of using can be exposed to a medium comprising at least one of beer, cider, energy drinks, flavored drinks, fruit drinks, liquor or other alcoholic beverages, milk, milk-containing beverages, soda, sports drinks, vegetable drinks, water, wine, and combinations thereof. In some embodiments, the medium can comprise at least one of non-consumable liquid (e.g., blood, non-potable water, organic solvents, potable water, serum, treated waste water, untreated waste water, urine, vomit, sweat, tears, feces, reproductive fluids, other bodily secretions, or combinations thereof). In some embodiments, the medium can comprise at least one of a solution, a suspension, or an emulsion. In some embodiments, medium can contain at least one of solid particles, solid material, or ice suspended therein. In some embodiments, the targeted substance may comprise any one of illicit drugs, amine-containing compounds, benzodiazepines, analytes, narcotics, alcohol, date rape drugs.

In some embodiments, a multi-layered detection system for detecting the presence of a targeted substance is described herein. In some embodiments, the multi-layered detection system can include a detection means to test a medium for the presence of a targeted substance; an entry means through which the medium travels to the detection means; at least one outer surface; and at least one viewing area for viewing a signal indicating whether the target substance is present in the medium.

In some embodiments, the detection means can refer to an assembly of mechanical and/or chemical items that can detect or signal the presence of a target substance. Examples of the detection means and detection layers are described throughout this Detailed Description. The entry means can refer to an area within the at least one outer surface can permits a medium to pass or travel to the detection means to initiate the testing of the medium. Examples of the entry means include a void, hole, perforated region of the at least one outer surface, and other entry means described throughout this Detailed Description. The at least one outer surface can refer to a surface that may be exposed to the environment surrounding the system, for example, the surface may face outward from a human body or toward a human body. Examples of the at least one outer surface include the top layer, bottom layer, and removable layer described throughout this Detailed Description. The viewing area can refer to an area where visible signal can be viewed. Examples of viewing areas include a transparent area or the at least one outer surface, a window or opening and other viewing areas described throughout this Detailed Description.

In some embodiments, the multi-layered detection system can further include an activation means that covers at least a portion of the entry means. The activation means can provide a protective layer that can prevent unintentional exposure of the entry means to the medium, prevent accidental or unintended testing of a medium, or otherwise protect the detecting means from damage.

In some embodiments of the multi-layered detection system, the matrix can be within a detection layer. The detection layer can comprise a first indicator and a second indicator, wherein the second indicator signals the presence of the targeted substance. Optionally, the first indicator and the second indicator are complementary such that when both the first indicator and the second indicator provide an indication, a joint indication provides notification to a user. The first indicator can be, for example, a control. The control can indicate that the detection means has been sufficiently exposed to a medium. The first indicator can signal a portion of at least one of a word, symbol, or character and the second indicator signals a different portion of the at least one of a word, symbol, or character. Optionally, the signal of the first indicator only signals to a user the presence of the targeted substance and wherein the joint signal of both the first indicator and the second indicator signals to a user the absence of a targeted substance.

In some embodiments, the detection means can display a signal. In some aspects, the detection means displays the signal upon a visible shift of at least part of the detection means. In some cases, the signal can include a color change. In some aspects, the signal can include the indicators described throughout this Detail Description. In some embodiments, the viewing area can be aligned with a portion of the detection means that displays the signal such that the signal may be visible through the viewing area.

In some aspects, the multi-layered detection system can positioned on a human body, for example, on a fingernail or as a patch on a user's skin. The system can be positioned on a human with the aid of an adhesive. In some embodiments, the system may have an arcuate shape. In some embodiments, the at least one outer surface of the multi-layered detection system may be a rigid material shaped in the form of a fake human fingernail. In other embodiments, the at least one outer surface of the multi-layered detection system may be a pliable material in the form of a human fingernail decal. In yet other embodiments, the at least one outer surface the multi-layered detection system may be applied as a coating, for example, as a liquid similar to fingernail polish. In other embodiments, the at least one outer surface of the multi-layered detection system may be in the form of a ring, a bracelet, a necklace, a charm, or a lanyard.

In some embodiments, the multi-layered detection system has sufficient structural strength to resist structural change from an external force that would damage the multi-layered detection system to the extent that the multi-layered detection system did not function to achieve an intended result. In some embodiments, the multi-layered detection system may protect the housed detection layer from damage, including damage from compressive forces, moisture damage, damage from liquids, and normal wear and tear. In some embodiments, the multi-layered detection system may be fully submersible in a liquid sample with minimal effect on the detection layer. In some embodiments, the multi-layered detection system may be fully submersible in a liquid sample with no effect on the detection layer. In some cases, the multi-layer detection system may have a boundary that prevents liquid entrainment when the system is fully submerged. As discussed in the Detailed Description, in some embodiments, the multi-layered detection system may sustain external perpendicular forces up to 2500 Newtons without impacting the ability of the system to detect the presence of a targeted substance. In some embodiments, the multi-layered detection system may sustain external axial compressive force of >60 Newtons without impacting the ability of the system to detect the presence of a targeted substance. The physical characteristics of the multi-layered detection system may be selected by selection of a suitable polymeric material or polymeric material blend as detailed above.

In some embodiments, the detection means of the multi-layered detection system may be limited to a one-time use to detect the presence of a targeted substance. In other embodiments, the detection means of the multi-layered detection system can be employed for multiple uses to detect the presence of a targeted substance. In some embodiments, the at least one outer surface can be used with a plurality of detection means.

In some embodiments, the at least one outer surface can be used with a plurality of detection means. For example, the at least one outer surface can be removed from a first detection means and applied to a second detection means.

In some embodiments, the apparatus and systems described herein may comprise a lateral flow assay. Other assays may be used with the apparatus described herein. In some embodiments, the apparatus and systems described herein may comprise one or more of a colorimetric assay, an electrochemical assay, a fluorescent assay, a radiolabeled assay, a magnetic assay, a lateral flow immunoassay, or the like.

In some embodiments, the apparatus and systems described herein can detect the presence of a targeted substance after being exposed to the target substance for less than 10 seconds, in other embodiments, less than 5 seconds, in yet other embodiments, less than 3 seconds, and in yet further embodiments, less than about 1 second.

In some embodiments, after being exposed to a liquid to be tested for a targeted substance, the apparatus and systems described herein can provide the results to a user in less than about 5 minutes, in other embodiments, less than about 1 minute, in yet other embodiments, less than about 30 seconds, and in yet further embodiments, less than about 10 seconds.

In some embodiments, the apparatus and systems described herein can be characterized by as to the minimum concentration of a targeted substance that the apparatus can detect. For example, for a targeted substance of ketamine, the apparatus can be configured to detect ketamine present in a liquid when ketamine may be present in a concentration less than about 5 mg/mL, in other embodiments, less than about 1 mg/mL, in yet other embodiments, less than about 0.5 mg/mL, and in yet other embodiments, less than about 0.1 mg/mL. As another example, for a targeted substance of benzodiazepine, the apparatus can be configured to detect benzodiazepine present in a liquid when benzodiazepine may be present in a concentration less than about 5 mg/mL, in other embodiments, less than about 1 mg/mL, in yet other embodiments, less than about 0.5 mg/mL, in yet other embodiments, less than about 0.05 mg/mL, and in yet further embodiments, less than about 0.005 mg/mL. As another example, for a targeted substance of GHB, the apparatus can be configured to detect GHB present in a liquid when GHB may be present in a concentration less than about 100 mg/mL, in other embodiments, less than about 50 mg/mL, in yet other embodiments, less than about 25 mg/mL, and in yet other embodiments, less than about 10 mg/mL. As another example, for a targeted substance of MDMA, the apparatus can be configured to detect MDMA present in a liquid when MDMA may be present in a concentration less than about 20 mg/mL, in other embodiments, less than about 10 mg/mL, in yet other embodiments, less than about 5 mg/mL, in yet other embodiments, less than about 1 mg/mL, and in yet further embodiments, less than about 0.5 mg/mL.

In some embodiments, the apparatus and systems described herein can have a shelf-life of up to about 1 year, in other embodiments, up to about 60 days, in yet other embodiments, up to about 30 days, and in yet further embodiments, up to about 15 days.

In some embodiments, the apparatus and systems described herein can detect the presence of a targeted substance in up to about 50% of commercially available beers, wines, liquor, or other alcoholic beverages, in other embodiments, up to about 75% of commercially available beers, wines, liquor, or other alcoholic beverages, in yet other embodiments, up to about 90% of commercially available beers, wines, liquor, or other alcoholic beverages, and in yet further embodiments, up to about 99% of commercially available beers, wines, liquor, or other alcoholic beverages.

Some embodiments of the apparatus described herein can provide a low cost device as compared to other detection devices. The apparatus can provide a discrete device for a user to test a substance in question, for example, by positioning the apparatus on a user's finger, the user can test a liquid with the simple insertion of the fingernail with the apparatus into a liquid for a short period of time in plain sight without having to leave his or her position. The apparatus can provide indication and feedback to the user in a relatively short period of time in a discrete manner. The apparatus described herein do not require a trained analyst to review the results, but instead an untrained user or intoxicated user can view the apparatus to determine if a target substance may be present or not. For example, the apparatus can provide a user with a qualitative indication of being clear of a targeted substance rather than a quantitative measurement that may be more cumbersome or confusing to analyze.

In some embodiments, the apparatus can provide clear results to a user. For example, if a color change or other indication is positively shown, then no drug is present. Such embodiments can provide a user greater confidence in the affirmative indication of a safe liquid. In embodiments where the targeted substance is a drug, the indication mechanism where a color change signifies that no drug is present can provide a user with greater confidence in the safety of the liquid, and thus minimizing the likelihood of reliance on false positive tests.

Because the methods may rely on marker movement and not on marker color change, the method in some embodiments may be useful for individuals who may be color blind or who are in a poorly lit environment.

In some embodiments, the methods, systems, and apparatuses described herein could provide preliminary forensic analyses that would be of assistance to law enforcement or forensic experts, e.g., quickly identifying the presence of a target substance in the blood, urine, vomit, or cup of someone that may have ingested one of the target substances identified herein. Advantageously, the methods and apparatuses described herein allow for the real-time determination of target substance, such as illicit drugs, in liquids, or certain proteins and allergens, in a substance. In some embodiments, the liquid tested may comprise other target substances that may be present naturally in the liquid.

EXAMPLES

Example 1

In one example, the methods and apparatus can be used to detect an amine-containing compound or drug. An "amine-containing" compound or drug, as referred to herein, includes species having at least one primary, secondary, and/or tertiary amine, and/or salts thereof. The amine formula can be represented by $NR^1R^2R^3$, wherein $R^1$, $R^2$, and $R^3$ can be the same or different from one another. The amine salts as described herein can be represented as $(HNR^1R^2R^3)^+X^-$, where $X^-$ is a counterion. $R^1$, $R^2$ and $R^3$ can include, but are not limited to, hydrogen, substituted and unsubstituted straight-chained or branched $C_1$-$C_6$ alkyls (e.g., methyl, ethyl, propyl, butyl, pentyl, hexyl), substituted and unsubstituted $C_6$-$C_{10}$ aryls (e.g., benzyl), substituted and unsubstituted straight-chained or branched $C_1$-$C_6$ alkanols (e.g., methanol, ethanol, propanol, butanol, pentanol, hexanol), substituted and unsubstituted $C_6$-$C_{10}$ aryl, substituted and unsubstituted heteroaryl, substituted and unsubstituted $C_4$-$C_8$ cycloalkyl, and combinations thereof, with the proviso that $R^1$, $R^2$ and $R^3$ cannot all be hydrogen. An amine-containing compound as described herein does not include ammonia or uronium compounds or salts thereof, such as urea and derivatives and salts thereof, e.g., urea nitrate.

Examples of amine-containing compounds as described herein include, for example, amphetamine, cathinone, cyclobenzaprine, diphenhydramine, doxylamine, ephedrine, ketamine, lysergic acid diethylamide (LSD), methamphetamine, 3,4-methylenedioxyamphetamine (MDA), 3,4-methylenedioxy-methamphetamine (MDMA), methcathinone, tetrahydrozoline and salts thereof, and combinations thereof.

In some embodiments, amine-containing compounds that can be detected according to the methods of using the apparatus described herein include, for example, narcotics, depressants, stimulants, hallucinogens, cannabinoids, and cathionones. Exemplary types of narcotics include opiates, heroin, hydrocodone, and morphine. An exemplary depressant includes cyclobenzaprine. Stimulants for detection according to the methods described herein include cocaine, amphetamines, 3,4-methylenedioxy-amphetamine (MDA), and 3,4-methylenedioxy-methamphetamine (MDMA). Hallucinogens for detection according to the methods described herein include psilocybin, lysergic acid diethylamide (LSD), and phencyclidine. Cannabinoids include natural and synthetic cannabinoids. Cathinones include natural and synthetic cathinones.

Optionally, the amine-containing compounds include amphetamine, cathinone, cyclobenzaprine, diphenhydramine, doxylamine, ephedrine, ketamine, lysergic acid diethylamide (LSD), methamphetamine, 3,4-methylenedioxyamphetamine (MDA), 3,4-methylenedioxy-methamphetamine (MDMA), methcathinone, tetrahydrozoline and salts thereof, and combinations thereof.

The apparatus for detecting an amine-containing compound can include a detection layer comprising a matrix having a marker. In some embodiments, the marker has the following formula:

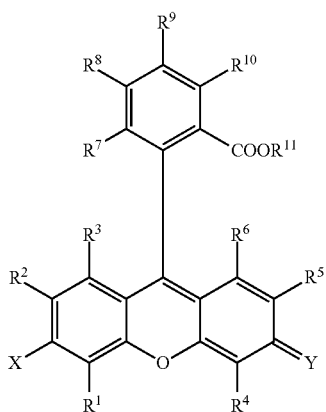

or a salt thereof, wherein: $R^1$, $R^2$, $R^3$, $R^4$, $R^5$, $R^6$, $R^7$, $R^8$, $R^9$, and $R^{10}$ are each independently selected from the group consisting of hydrogen, halogen, hydroxyl, nitro, cyano, trifluoromethyl, substituted or unsubstituted amino, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted carbonyl, substituted or unsubstituted carboxyl, substituted or unsubstituted thio, and substituted or unsubstituted sulfonyl; $R^{11}$ is hydrogen or substituted or unsubstituted alkyl; X is hydroxyl or substituted or unsubstituted amino; and Y is O or $NR^{12}$, wherein $R^{12}$ is hydrogen or substituted or unsubstituted alkyl.

In some embodiments, the marker has the following formula:

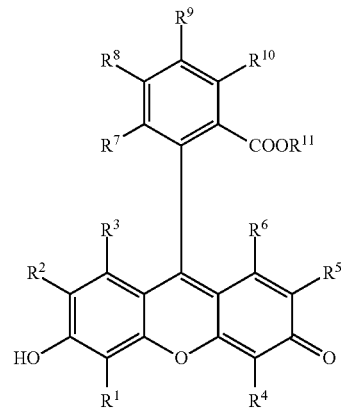

or a salt thereof, wherein: $R^1$, $R^2$, $R^3$, $R^4$, $R^5$, $R^6$, $R^7$, $R^8$, $R^9$, and $R^{10}$ are each independently selected from the group consisting of hydrogen, halogen, hydroxyl, nitro, cyano, trifluoromethyl, substituted or unsubstituted amino, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted carbonyl, substituted or unsubstituted carboxyl, substituted or unsubstituted thio, and substituted or unsubstituted sulfonyl; and $R^{11}$ is hydrogen or substituted or unsubstituted alkyl.

In some embodiments, the marker has the following formula:

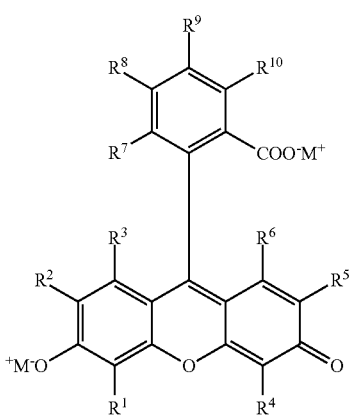

wherein $R^1$, $R^2$, $R^3$, $R^4$, $R^5$, $R^6$, $R^7$, $R^8$, $R^9$, and $R^{10}$ are each independently selected from the group consisting of hydrogen, halogen, hydroxyl, nitro, cyano, trifluoromethyl, substituted or unsubstituted amino, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted carbonyl, substituted or unsubstituted carboxyl, substituted or unsubstituted thio, and substituted or unsubstituted sulfonyl; and $M^+$ is a cation. In some such embodiments, $M^+$ is selected from the group consisting of $Na^+$, $K^+$, $Li^+$, $Cs^+$, $Rb^+$, $Ag^+$, $Au^+$, $Cu^+$, $NH_4^+$, $NR_4^+$, and $NR_1R_2R_3^+$.

The marker for use in the marker composition described herein includes compounds represented by the following formula:

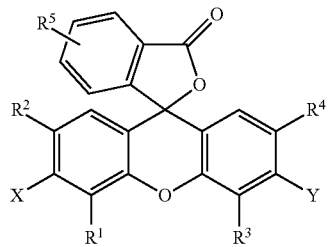

or a salt thereof, wherein $R^1$, $R^2$, $R^3$, $R^4$, and $R^5$ are each independently selected from the group consisting of hydrogen, halogen, hydroxyl, nitro, cyano, trifluoromethyl, substituted or unsubstituted amino, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted carbonyl, substituted or unsubstituted carboxyl, substituted or unsubstituted thio, and substituted or unsubstituted sulfonyl. In some embodiments, X and Y are each independently hydroxyl or substituted or unsubstituted amino.

The apparatus comprising the detection layer including the marker can be exposed to a liquid. If no amine-containing compound (e.g., amine-containing drug), is present in the liquid, the marker color will move freely with the solvent front as it advances through the matrix. However, when one or more amine-containing compounds (e.g., an amine-containing drug) is present in the liquid, the color will not advance with the solvent front or it will advance only slowly relative to the rate of advance in a blank control sample.

If an amine-containing compound to be detected is present, the small dot or line of marker does not substantially move (see, for example, like that shown in FIG. 4A). When an amine-containing compound is not present in the liquid in an amount that is detectable, the marker dot or line substantially moves with the liquid along the front, possibly with some tailing behind the moving marker dot or line (see, for example, like that shown in FIG. 4B). Other indicators as described and shown herein can be used in embodiments, for example the display of "OK" like that shown in FIG. 3B.

While the substance to be tested may include other substances, the method and apparatuses described herein is able to detect the "club drugs" and other hallucinogens, psychotropic drug, and dissociative drugs because the amount of same is much greater than the amine-containing compounds that may be naturally present in beer, wine, etc. For example, a ketamine dosage is typically on the order of 40-250 mg, a MDMA dosage is typically 30-200 mg, an MDA dosage is typically 30-200 mg, a methamphetamine dosage is typically 5-150 mg, and an amphetamine dosage is typically 10-200 mg. These amounts, when taken or surreptitiously slipped into a beverage can be in some cases up to 100 times (or more) greater than any naturally present amine-containing compounds.

In another example, the apparatus for detecting a target substance can include a detection layer comprising a lateral flow assay, for example, like those described and set forth in a PCT patent application entitled "Methods and Apparatus for Detecting Compounds in Liquids," applied for by Undercover Colors, Inc. and filed on the same day as the present application, which is incorporated by reference in its entirety. In certain embodiments, the apparatus can detect an amine-containing compound. In some such embodiments, the detection layer can be prepared as follows.

Example 2

A lateral flow immunoassay of the invention was prepared as follows. A benzo test line solution was prepared using (Benzodiazepine-BSA, 5:1 ratio) solution diluted to 2 mg/mL with pH 7.4 Phosphate Buffered Saline (1×). A benzo control line solution was prepared using Goat Anti-Mouse Antibody solution diluted to 1 mg/mL with pH 7.4 Phosphate Buffered Saline (1×). A test line of the diluted benzo test line solution was printed 12 mm from the bottom of the FF120HP (GE Healthcare) nitrocellulose strip, which has a capillary rise time of about 120 seconds for 4 cm. A control line of diluted benzo control line solution was printed 1.5 mm above the test line. The printed strip was placed in a forced air oven to dry for 60 minutes at 10% humidity and 37° C., and then it was stored in a desiccator at 20% humidity until used. The printed FF120HP nitrocellulose strip was treated with the Abcam Immunoassay Buffer (BSA Free), and was placed in a forced air oven to dry for 60 minutes at 10% humidity and 37° C., and then it was stored in a desiccator at 20% humidity until used.

Monoclonal Mouse Anti-Benzodiazepine Antibody-Gold NP conjugate was prepared by first desalting the Monoclonal Mouse Anti-Benzodiazepine Antibody solution using a Zeba spin columns (Thermo Scientific, PN: 89882) to replace the stock buffer with 100 mM, pH 7.4 sodium phosphate buffer. The desalted Monoclonal Mouse Anti-Benzodiazepine Antibody solution in PBS was then conjugated to 40 nm colloidal gold nanoparticles in 50 mM Sodium Borate Buffer. During the conjugation process the 5 mM Sodium Borate buffer with 5% BSA is added to the conjugation solution. Upon completion of the conjugation of the Monoclonal Mouse Anti-Benzodiazepine Antibody to the 40 nm gold NP, the Monoclonal Mouse Anti-Benzodiazepine Antibody-Gold NP conjugate was concentrated and subsequently diluted to OD10 with 100 mM Sodium Borate buffer containing 0.5% Fish Skin Gelatin and 0.1% Tween 80.

A conjugate pad was prepared by pretreating a strip of Ahlstrom 8964 glass fiber pad with 50 mM Sodium Borate containing 1% BSA, 5% Sucrose, 2% Trehalose, 0.25%

Tween 20, and 0.15M KCl, and then the pretreated 6614 strip was placed in a forced air oven for 60 minutes at 10% humidity and 37° C., and then stored in a desiccator at 20% humidity until used. The buffered diluted conjugate solution was printed continuously across the 8864 strip at a rate of 8 uL per centimeter, and then the strip was placed in a forced air oven for 60 minutes at 10% humidity and 40° C., and then stored in a desiccator at 20% humidity.

To prepare the sample pad a strip of CF4 (GE Healthcare) was treated with 1M K2CO3, and then the strip was placed in a forced air oven for 60 minutes at 10% humidity and 40° C., and then stored in a desiccator at 20% humidity. The master card was assembled by applying a printed strip of nitrocellulose to an adhesive backing. The conjugate pad was applied so as to achieve an overlap of 2 mm with the bottom of the nitrocellulose. The sample pad was applied so as to achieve an overlap of 2 mm with the bottom of the conjugate pad. An Ahlstrom 319 wicking pad was applied as to achieve an overlap of 2 mm with the top of the nitrocellulose. The master card was then cut into 4 mm wide strips.

Example 3

Buffer solutions were prepared as follows:

Antibody Desalting Buffer Solution: A 100 mM sodium phosphate, pH 7.5 buffer was prepared by combining, in order: Molecular Biology Reagent Water (Sigma, PN: W4502) was added in the amount of: 080% of total batch volume; Sodium phosphate monobasic (Sigma, PN: S3139) was added in the amount of: 10.2 g/L×batch volume (L); Sodium phosphate dibasic (Sigma, PN: S9763 was added in the amount of: 58.91 g/L×batch volume (L); Molecular Biology Reagent Water (Sigma, PN: W4502) to final volume. pH was adjusted to 7.5 using NaOH or concentrated HCl.

Conjugation Blocking Buffer Solution: A 50 mM sodium borate, 10% BSA, pH 9.0 buffer was prepared by combining, in order: Sodium tetraborate decahydrate (Fisher, PN: AC41945-0010): 11.4 g/L; Boric acid (Fisher, PN: A74-1): 1 g/L; Bovine serum albumin (BSA, Equitech, PN: BAH64): 100 g/L; Molecular Biology Reagent Water (Sigma, PN: W4502) to final volume; pH was adjusted to 9.0 using NaOH or HCl, and then the buffer was filtered using a 0.2 μm filter (VWR, PN: 73520-994).

Conjugate Dilution Buffer Solution: A 50 mM sodium borate, 1% BSA, 5% trehalose, and 20% sucrose, pH 9.0 buffer was prepared by combining, in order: Sodium tetraborate decahydrate (Fisher, PN: AC41945-0010): 11.4 g/L; Boric acid (Fisher, PN: A74-1): 1 g/L; Bovine serum albumin (BSA, Equitech, PN: BAH64): 10 g/L; Sucrose (Sigma, PN: 84097); Trehalose (Sigma, PN: 90210); Molecular Biology Reagent Water (Sigma, PN: W4502) to final volume.

Chromatographic Membrane Buffer Solution: A 10 mM sodium phosphate, 0.1% sucrose, 0.1% BSA, 0.2% PVP-40, pH 7.5 buffer was prepared by combining, in order, per liter of buffer: Sodium phosphate monobasic (Sigma, PN: S3139), 0.204 g; Sodium phosphate dibasic (Sigma, PN: S9763), 1.178 g; Sucrose (Sigma, PN: 84097) 1.0 g; Bovine serum albumin (BSA, Equitech, PN: BA H64). 1.0 g; Poly(vinylpyrrolidone)-40 (PVP-40, Sigma, PN: PVP-40): 2.0 g; Molecular Biology Reagent Water (Sigma, PN: W4502) to one liter. pH was adjusted to 7.2 using NaOH or HCl, and then the buffer was filtered using a 0.2 μm filter (VWR, PN: 73520-994).

Conjugate Pad Buffer Solution: A 0.5 M Tris, 3% BSA, 1% PVP-40, 0.25% Triton X-100, 0.5% Pluronic F-68, pH 8.0 buffer was pre prepared by combining, in order: Tris base (Sigma, PN: T1375): 114.8 g/L; Bovine serum albumin (BSA, Equitech, PN: BAH64): 30 g/L; Polyvinylpyrrolidone-40 (PVP-40, Sigma, PN: PVP-40): 10 g/L; Triton X-100 (Sigma, PN: T8787): 2.5 g/L; Pluronic F-68 (Thermo Fisher, PN: 24040032): 5 g/L; Add Molecular Biology Reagent Water (Sigma, PN: W4502) to final volume.

Sample Area Buffer Solution: A 1.0 M Potassium Carbonate (K2CO3) buffer with 0.25% Triton X-305, pH 7.0 buffer was pre prepared by combining, in order: Potassium carbonate (Sigma PN: P1472): 138.2 g/L; Triton X-305 (Sigma, PN: X305): 3.6 g/L; Add Molecular Biology Reagent Water (Sigma, PN: W4502) to final volume.

Example 4

A lateral flow immunoassay of the invention with a combined sample-conjugate pad was prepared as follows. A benzo test line solution was prepared using (Benzodiazepine-BSA, 5:1 ratio) solution diluted to 4 mg/mL with pH 7.4 Phosphate Buffered Saline (1×). A benzo control line solution was prepared using Goat Anti-Mouse Antibody solution diluted to 1 mg/mL with pH 7.4 Phosphate Buffered Saline (1×). A test line of the diluted benzo test line solution was printed 5 mm from the bottom of the 8 mm wide CN095 (Sartorius) nitrocellulose strip, which has a capillary rise time of about 85±10 seconds for 4 cm. A control line of diluted benzo control line solution was printed 2 mm above the test line. The printed strip was placed in a forced air oven to dry for 30 minutes at 10% humidity and 40° C., and then it was stored for 16 hours in a desiccator at 20% humidity. The printed CN095 nitrocellulose strip (Sartorius) was treated with the Chromatographic Membrane Buffer described above in Example 3, and was placed in a forced air oven to dry for 30 minutes at 10% humidity and 40° C., and then it was stored for 16 hours in a desiccator at 20% humidity.

Monoclonal Mouse Anti-Benzodiazepine Antibody-Gold NP conjugate was prepared by first desalting the Monoclonal Mouse Anti-Benzodiazepine Antibody solution using a Zeba spin columns (Thermo Scientific, PN: 89882) to replace the stock buffer with 100 mM, pH 7.4 sodium phosphate buffer. The desalted Monoclonal Mouse Anti-Benzodiazepine Antibody solution in PBS was then conjugated to 40 nm colloidal gold nanoparticles. During the conjugation process the Conjugation Blocking Buffer is added to the conjugation solution. Upon completion of the conjugation of the Monoclonal Mouse Anti-Benzodiazepine Antibody to the 40 nm gold NP, the Monoclonal Mouse Anti-Benzodiazepine Antibody-Gold NP conjugate was concentrated and subsequently diluted to OD15 with the Conjugate Dilution Buffer as described above in Example 3.

A combined sample-conjugate pad was prepared by pretreating a strip of Ahlstrom 6614 polyester fiber pad with Conjugate Pad Buffer described above in Example 3, and then the pretreated 6614 strip was placed in a forced air oven for 60 minutes at 10% humidity and 40° C., and then stored for 16 hours in a desiccator at 20% humidity. To prepare the sample area of the combined sample-conjugate pad, only the sample area of an Ahlstrom 6614 polyester fiber pad was treated with the Sample Area Buffer described above in Example 3. The buffered diluted conjugate solution was printed continuously across the strip on 6614 in only the conjugate area at a rate of 5 uL per centimeter, and then the strip was placed in a forced air oven for 60 minutes at 10% humidity and 40° C., and then stored for 16 hours in a desiccator at 20% humidity.

The master card was assembled by applying a printed strip of nitrocellulose to an adhesive backing. The sample/conjugate pad was applied so as to achieve an overlap of 2 mm with the bottom of the nitrocellulose. An Ahlstrom 319 wicking pad was applied as to achieve an overlap of 2 mm with the top of the nitrocellulose. The master card was then cut into 4 mm wide strips.

Example 5

The effect of $K_2CO_3$ and TRIS sample pad treatment on lateral flow assay results are provided herein. Lateral flow assays were prepared by the process of Example 4, except that the assays of Table 1 had no sample pad/area pretreatment, and the assays of Table 2 were pretreated with a sample area buffer solution comprising potassium OK. A check indicates no assay failure. An X equals false negative results due to non-specific binding of conjugate to test line. The false negative results were overcome by pre-treatment, with one exception of hot coffee.

Procedure:
1.) Prepare assays according to the procedure described in Example 4. Prepare half of the assays without the addition of the Sample Area Buffer.
2.) Prepare individual spiked solutions of each beverage listed. The beverages are spiked with either Alprazolam, Diazepam, or Flunitrazepam to a final concentration of 1000 ng/mL.
3.) Deposit 20 μL of the designated blank beverage on the untreated sample area of three assays per designated beverage and record the results at 1 minute.
4.) Deposit 20 μL of the designated spiked beverage on the untreated sample area of three assays per designated beverage and record the results at 1 minute.
5.) Deposit 20 μL of the designated blank beverage on the treated sample area of three assays per designated beverage and record the results at 1 minute.
6.) Deposit 20 μL of the designated spiked beverage on the treated sample area of three assays per designated beverage and record the results at 1 minute.

TABLE 1

| | No potassium carbonate pre-treatment of sample pad/area. | | | |
|---|---|---|---|---|
| | | Valium (diazepam) | Xanax (alprazolam) | Rohypnol (flunitrazepam) |
| Beer/Other | Sam Adams Boston Lager | ✓ | ✓ | ✓ |
| | Guinness | ✓ | ✓ | ✓ |
| | Blue Moon | ✓ | ✓ | ✓ |
| | Big Boss Bad Penny | ✓ | ✓ | ✓ |
| | Lonerider Shotgun Betty Hefeweizen | ✓ | ✓ | ✓ |
| | Foothills People's Porter | ✓ | ✓ | ✓ |
| | Duck-Rabbit Amber | ✓ | ✓ | ✓ |
| | Sweetwater IPA | ✓ | ✓ | ✓ |
| | Sierra Nevada Pale Ale | ✓ | ✓ | ✓ |
| | Bell's Oberon | ✓ | ✓ | ✓ |
| | Mike's Hard Lemonade | X | X | X |
| | Angry Orchard Cider | X | X | X |
| White Wine | Yellowtail Pinot Grigio | X | ✓ | ✓ |
| | Barefoot Moscato | X | X | X |
| | Gallo Chardonnay | ✓ | ✓ | ✓ |
| | Mondavi Woodbridge Sauvignon Blanc | X | X | X |
| | Barefoot Riesling | X | X | ✓ |
| Rose Wine | Gallo White Merlot | X | X | X |
| | Sutter Home Pink Moscato | X | ✓ | X |
| | Yellowtail Pink Moscato | X | X | X |
| | Barefoot Red Moscato | ✓ | ✓ | ✓ |
| | Mondavi Woodbridge White Zinfandel | X | X | X |
| Red Wine | Yellowtail Merlot | X | X | X |
| | Sutter Home Pinot Noir | X | X | X |
| | Barefoot Shiraz | ✓ | ✓ | ✓ |
| | Mondavi Woodbridge Zinfandel | ✓ | ✓ | ✓ |
| | Gallo Cabernet Sauvignon | ✓ | ✓ | ✓ |
| Mixed Drinks | Rum and Coke | ✓ | ✓ | ✓ |
| | Martini | ✓ | ✓ | ✓ |
| | Mojito | X | X | X |
| | Old Fashioned | ✓ | ✓ | ✓ |
| | Long Island Iced Tea | X | X | X |
| | White Russian | ✓ | ✓ | ✓ |
| | Pina Colada | ✓ | ✓ | ✓ |
| | Jose Cuervo Ready to Drink Classic Margarita | ✓ | ✓ | ✓ |
| | Screwdriver | ✓ | ✓ | ✓ |
| | Cosmopolitan | ✓ | ✓ | ✓ |
| | Tequila Sunrise | ✓ | ✓ | ✓ |
| | Margarita | X | X | X |
| | Daiquiri | X | X | X |
| | Irish Coffee | X | X | X |
| | Bloody Mary | ✓ | ✓ | ✓ |
| Liquor | Smirnoff Vodka | ✓ | ✓ | ✓ |
| | Captain Morgan Spiced Rum | ✓ | ✓ | ✓ |
| | Jack Daniel's Whiskey | ✓ | ✓ | ✓ |
| | Jagermeister | ✓ | ✓ | ✓ |
| | Tanqueray Gin | X | X | X |
| | Bacardi Rum | ✓ | ✓ | ✓ |
| | Crown Royal Whisky | X | X | X |

TABLE 1-continued

No potassium carbonate pre-treatment of sample pad/area.

|  |  | Valium (diazepam) | Xanax (alprazolam) | Rohypnol (flunitrazepam) |
|---|---|---|---|---|
|  | Jim Beam Bourbon | ✓ | ✓ | ✓ |
|  | Jose Cuervo Tequila | ✓ | ✓ | ✓ |
|  | Fireball Cinnamon Whisky | ✓ | ✓ | ✓ |
|  | Dekuyper Peachtree | ✓ | ✓ | ✓ |
|  | Malibu Coconut Rum | ✓ | ✓ | ✓ |
| Mixers | Cranberry Juice | ✓ | ✓ | ✓ |
|  | Lemonade | ✓ | X | X |
|  | Hawaiian Punch | ✓ | ✓ | ✓ |
|  | Half and Half | ✓ | ✓ | ✓ |
|  | Coffee (hot) | X | X | X |
|  | Orange Juice | ✓ | ✓ | ✓ |
|  | Rose's Mojito Mix | X | X | X |
|  | Tonic Water | ✓ | ✓ | ✓ |
|  | Pineapple Juice | X | X | X |
|  | Coke | ✓ | ✓ | ✓ |
|  | V8 | ✓ | ✓ | ✓ |
|  | Club Soda | ✓ | ✓ | ✓ |
|  | Lime Juice | X | X | X |

TABLE 2

With potassium carbonate pre-treatment of sample pad/area.

|  |  | Valium (diazepam) | Xanax (alprazolam) | Rohypnol (flunitrazepam) |
|---|---|---|---|---|
| Beer/Other | Sam Adams Boston Lager | ✓ | ✓ | ✓ |
|  | Guinness | ✓ | ✓ | ✓ |
|  | Blue Moon | ✓ | ✓ | ✓ |
|  | Big Boss Bad Penny | ✓ | ✓ | ✓ |
|  | Lonerider Shotgun Betty Hefeweizen | ✓ | ✓ | ✓ |
|  | Foothills People's Porter | ✓ | ✓ | ✓ |
|  | Duck-Rabbit Amber | ✓ | ✓ | ✓ |
|  | Sweetwater IPA | ✓ | ✓ | ✓ |
|  | Sierra Nevada Pale Ale | ✓ | ✓ | ✓ |
|  | Bell's Oberon | ✓ | ✓ | ✓ |
|  | Mike's Hard Lemonade | ✓ | ✓ | ✓ |
|  | Angry Orchard Cider | ✓ | ✓ | ✓ |
| White Wine | Yellowtail Pinot Grigio | ✓ | ✓ | ✓ |
|  | Barefoot Moscato | ✓ | ✓ | ✓ |
|  | Gallo Chardonnay | ✓ | ✓ | ✓ |
|  | Mondavi Woodbridge Sauvignon Blanc | ✓ | ✓ | ✓ |
|  | Barefoot Riesling | ✓ | ✓ | ✓ |
| Rose Wine | Gallo White Merlot | ✓ | ✓ | ✓ |
|  | Sutter Home Pink Moscato | ✓ | ✓ | ✓ |
|  | Yellowtail Pink Moscato | ✓ | ✓ | ✓ |
|  | Barefoot Red Moscato | ✓ | ✓ | ✓ |
|  | Mondavi Woodbridge White Zinfandel | ✓ | ✓ | ✓ |
| Red Wine | Yellowtail Merlot | ✓ | ✓ | ✓ |
|  | Sutter Home Pinot Noir | ✓ | ✓ | ✓ |
|  | Barefoot Shiraz | ✓ | ✓ | ✓ |
|  | Mondavi Woodbridge Zinfandel | ✓ | ✓ | ✓ |
|  | Gallo Cabernet Sauvignon | ✓ | ✓ | ✓ |
| Mixed Drinks | Rum and Coke | ✓ | ✓ | ✓ |
|  | Martini | ✓ | ✓ | ✓ |
|  | Mojito | ✓ | ✓ | ✓ |
|  | Old Fashioned | ✓ | ✓ | ✓ |
|  | Long Island Iced Tea | ✓ | ✓ | ✓ |
|  | White Russian | ✓ | ✓ | ✓ |
|  | Pina Colada | ✓ | ✓ | ✓ |
|  | Jose Cuervo Ready to Drink Classic Margarita | ✓ | ✓ | ✓ |
|  | Screwdriver | ✓ | ✓ | ✓ |
|  | Cosmopolitan | ✓ | ✓ | ✓ |
|  | Tequila Sunrise | ✓ | ✓ | ✓ |
|  | Margarita | ✓ | ✓ | ✓ |
|  | Daiquiri | ✓ | ✓ | ✓ |
|  | Irish Coffee | ✓ | ✓ | ✓ |
|  | Bloody Mary | ✓ | ✓ | ✓ |
| Liquor | Smirnoff Vodka | ✓ | ✓ | ✓ |
|  | Captain Morgan Spiced Rum | ✓ | ✓ | ✓ |
|  | Jack Daniel's Whiskey | ✓ | ✓ | ✓ |
|  | Jagermeister | ✓ | ✓ | ✓ |

TABLE 2-continued

| | | Valium (diazepam) | Xanax (alprazolam) | Rohypnol (flunitrazepam) |
|---|---|---|---|---|
| | Tanqueray Gin | ✓ | ✓ | ✓ |
| | Bacardi Rum | ✓ | ✓ | ✓ |
| | Crown Royal Whisky | ✓ | ✓ | ✓ |
| | Jim Beam Bourbon | ✓ | ✓ | ✓ |
| | Jose Cuervo Tequila | ✓ | ✓ | ✓ |
| | Fireball Cinnamon Whisky | ✓ | ✓ | ✓ |
| | Dekuyper Peachtree | ✓ | ✓ | ✓ |
| | Malibu Coconut Rum | ✓ | ✓ | ✓ |
| Mixers | Cranberry Juice | ✓ | ✓ | ✓ |
| | Lemonade | ✓ | ✓ | ✓ |
| | Hawaiian Punch | ✓ | ✓ | ✓ |
| | Half and Half | ✓ | ✓ | ✓ |
| | Coffee (hot) | X | X | X |
| | Orange Juice | ✓ | ✓ | ✓ |
| | Rose's Mojito Mix | ✓ | ✓ | ✓ |
| | Tonic Water | ✓ | ✓ | ✓ |
| | Pineapple Juice | ✓ | ✓ | ✓ |
| | Coke | ✓ | ✓ | ✓ |
| | V8 | ✓ | ✓ | ✓ |
| | Club Soda | ✓ | ✓ | ✓ |
| | Lime Juice | ✓ | ✓ | ✓ |

With potassium carbonate pre-treatment of sample pad/area.

Example 6

Faster development of test results in inventive assays versus comparative assays are provided. Lateral flow assays were prepared by the process of Example 4 and were compared to commercial lateral flow assays (DBZ-114 distributed by Innovacon, San Deigo, Calif.) 30 seconds after exposure to a test fluid. The inventive assay results are fully developed by 30 seconds, whereas the comparative assays had not fully developed at 30 seconds.

Figure 29:
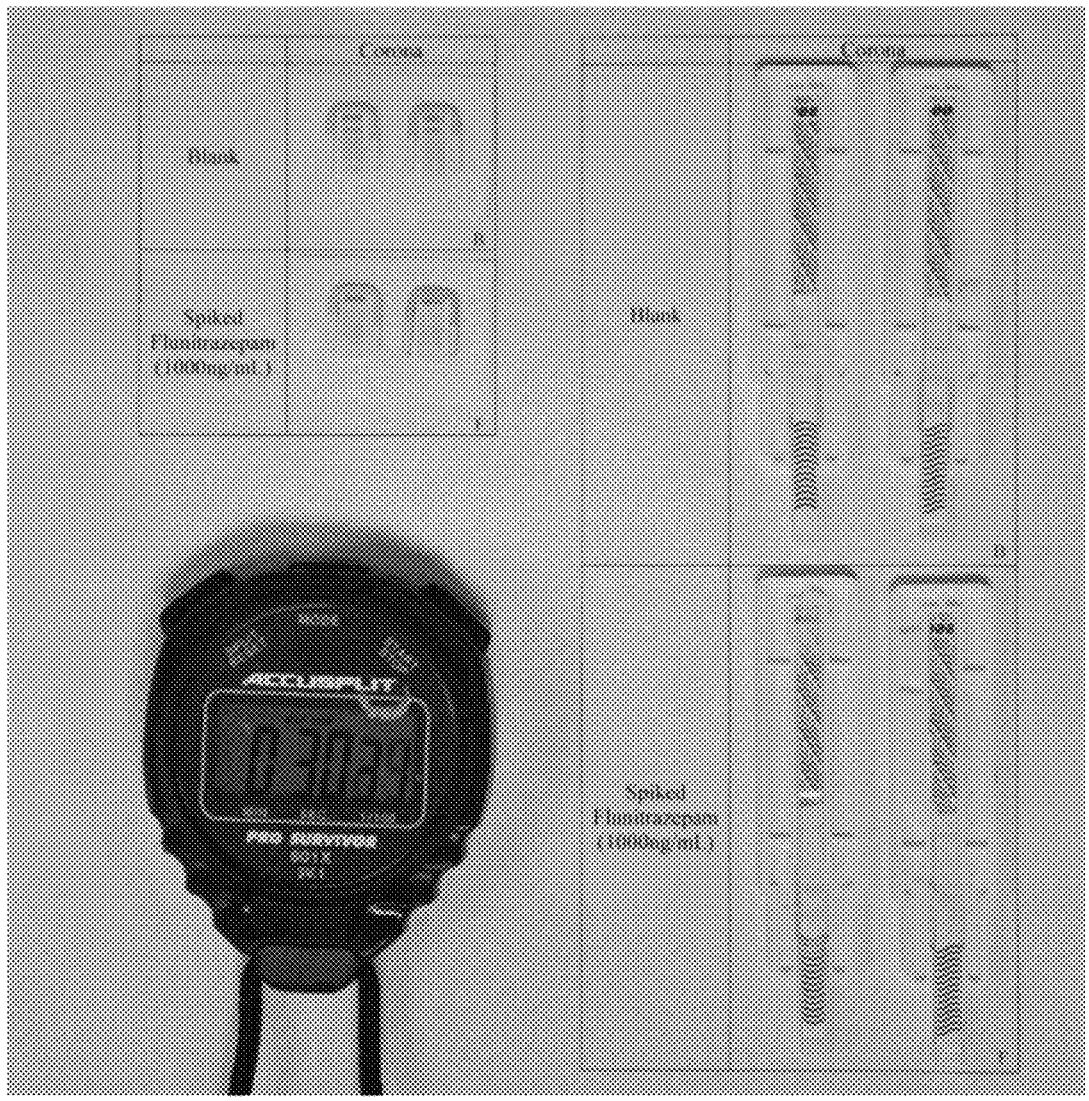
FIG. 29 shows test results of comparative assays and inventive assays according to some embodiments described herein.

Procedure:
1.) Prepare assays according to the procedure described in Example 3. To prepare linear assays use a rectangular Ahlstrom 319 wick. To prepare miniaturized assays use the U-shaped Ahlstrom 319 wick.
2.) Arrange the miniaturized and linear assays on the testing sheet.
3.) Deposit 20 μL of blank Corona beer on the sample area of the linear assays marked blank.
4.) Deposit 20 μL of Corona beer spiked with 1000 ng/mL Flunitrazepam on the sample area of the linear assays.
5.) Deposit 20 μL of blank Corona beer on the sample pad of the U-wick assays marked blank.
6.) Deposit 20 μL of Corona beer spiked with 1000 ng/mL Flunitrazepam on the sample pad of the U-wick assays.
7.) Take picture at 30 seconds Results are shown in FIG. 29 with the lateral flow assays prepared by Example 4 shown on the left and the commercial lateral flow assays shown on the right.

Example 7

Beverage components cause false negative results in comparative assays, but not in inventive assays. Comparative commercial assays as used in Example 6 fail (due to false negatives) in whiskey and moscato after 5 minutes of development due to specifications of the commercial assay. The commercial assay completely fails to run in daiquiri, and no results are visible after 5 minutes. The inventive assays (prepared as in Example 4) perform successfully in all cases, with no false negative results.

Procedure:
1.) Prepare miniature assays according to the procedure described in Example 3.
2.) Arrange the miniaturized and commercial assays on the testing sheet.
3.) Deposit 20 μL of the designated blank beverage on the sample area of the miniature assays marked blank.
4.) Deposit 20 μL of designated beverage spiked with 1000 ng/mL Flunitrazepam on the sample area of the miniature assays.
5.) Deposit 100 μL of designated blank beverage on the sample pad of the commercial assays marked blank.
6.) Deposit 100 μL of designated beverage with 1000 ng/mL Flunitrazepam on the sample pad of the commercial assays.
7.) Take picture at 5 minutes to allow time for the commercial assays to fully develop.

Figure 30:
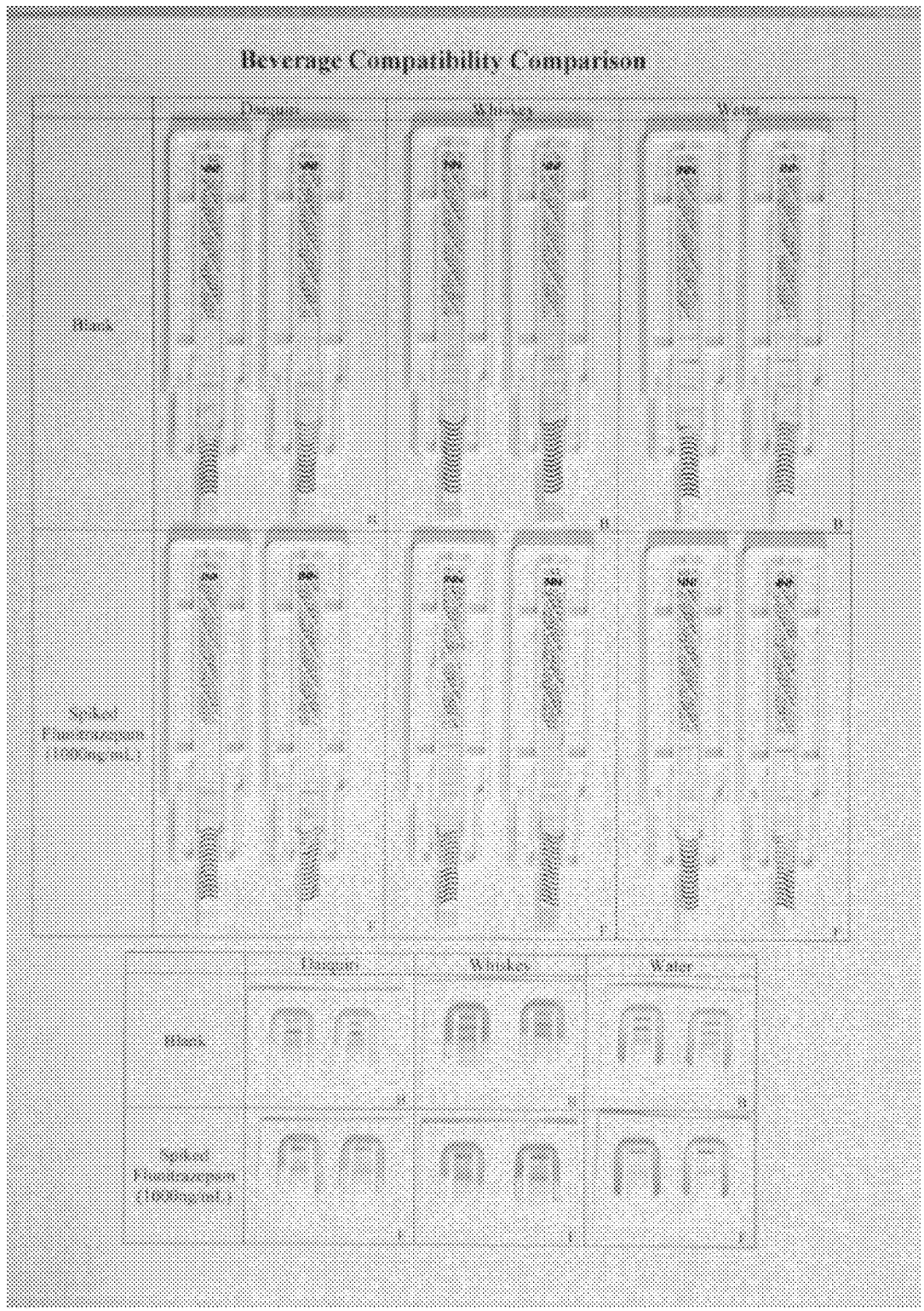
FIG. 30 shows test results of comparative assays and inventive assays according to some embodiments described herein.
Figure 31:
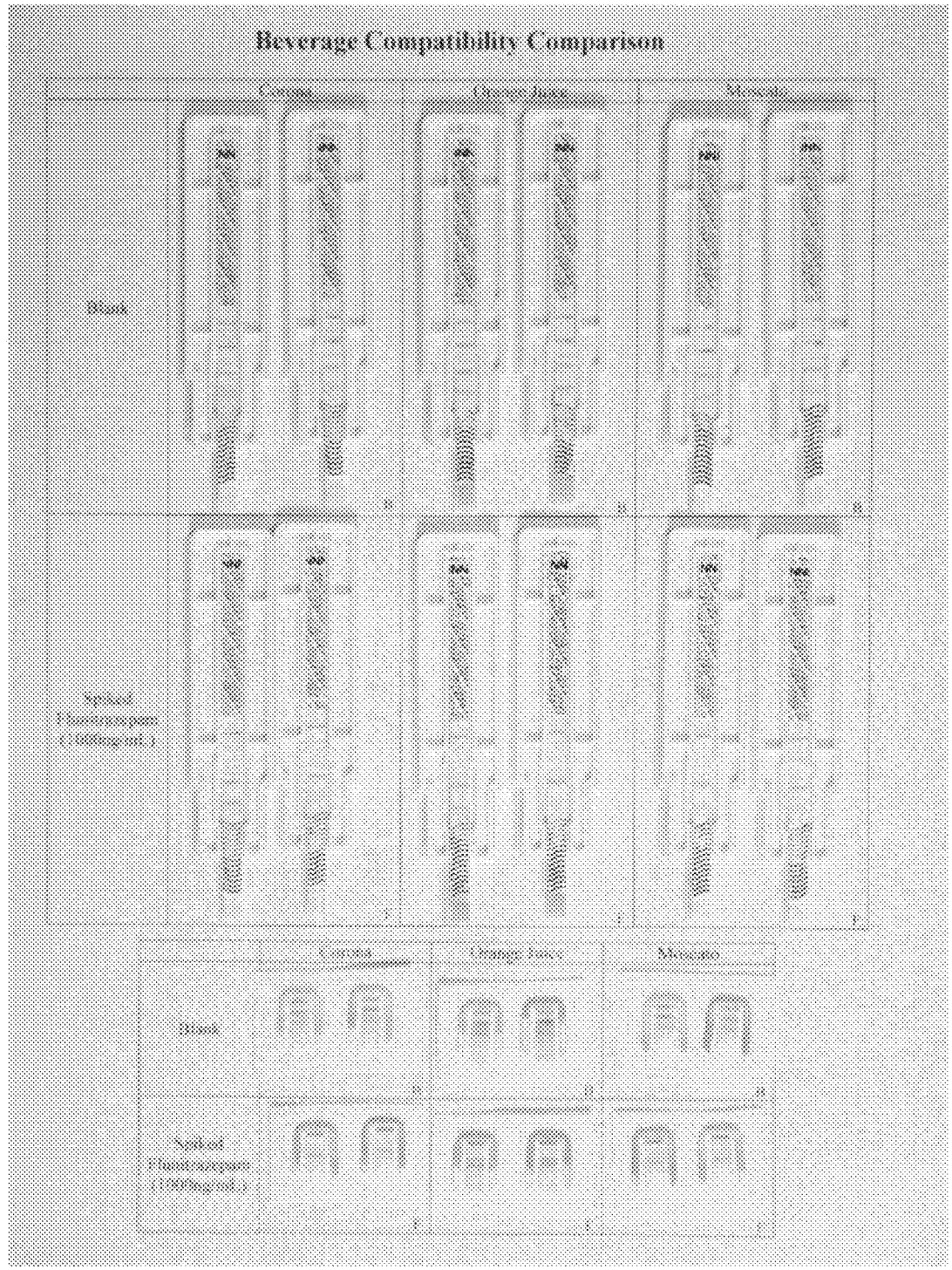
FIG. 31 shows test results of comparative assays and inventive assays according to some embodiments described herein.

Results are shown in FIG. 30 for daiquiri, whisky, and water, and in FIG. 31 for Corona, orange juice, and moscato, with the six commercial assays on top and the six inventive assays on the bottom in both Figures.

Example 8

U-shaped wick shortens assay length without affecting performance. Inventive assays (prepared as in Example 4) with a U-shaped wick (shown on right), where the fluid path is longer than the assay length, perform just as well as inventive assays (prepared as in Example 4) with a linear wick (shown on left), where the fluid path equals the assay length.

Procedure:
1.) Prepare assays according to the procedure described in Example 3. To prepare linear assays use a rectangular Ahlstrom 319 wick. To prepare miniaturized assays use the U-shaped Ahlstrom 319 wick.
2.) Arrange the miniaturized and linear assays on the testing sheet.
3.) Deposit 20 μL of blank Corona on the sample area of the linear assays marked blank.
4.) Deposit 20 μL of Corona spiked with 1000 ng/mL Flunitrazepam on the sample area of the linear assays.

Figure 32:
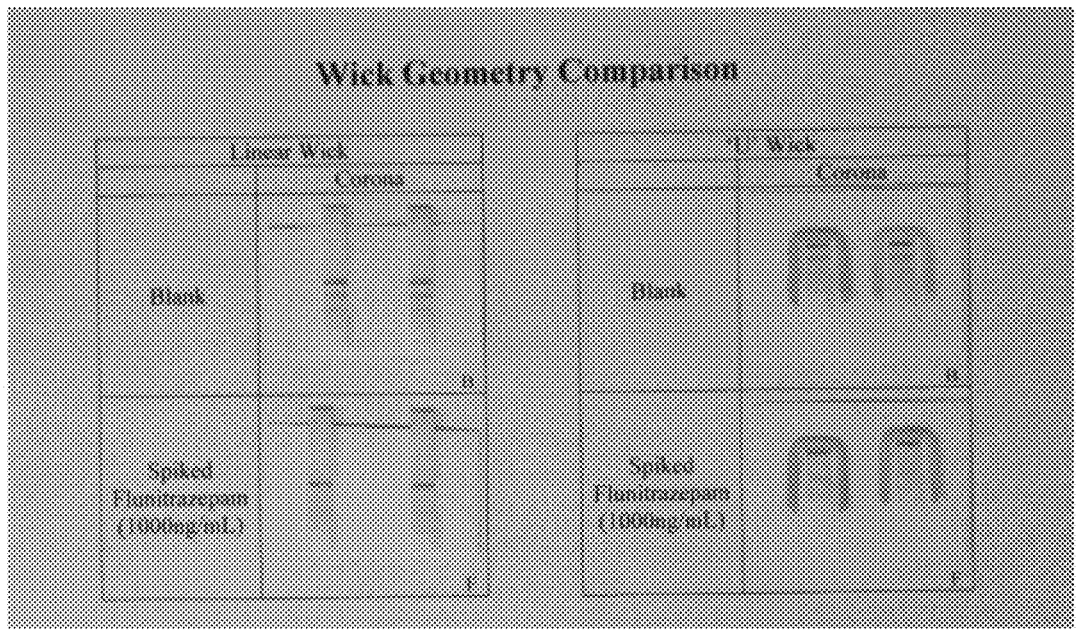
FIG. 32 shows of test results of comparative assays and inventive assays according to some embodiments described herein.

5.) Deposit 20 µL of blank Corona on the sample pad of the U-wick assays marked blank.
6.) Deposit 20 µL of Corona spiked with 1000 ng/mL Flunitrazepam on the sample pad of the U-wick assays.
7.) Take picture at 30 seconds Results are shown in FIG. 32 with the U-shaped wick assays on the right and the linear wick assays on the left.

The apparatus, systems, and methods of the appended claims are not limited in scope by the specific apparatus, systems, and methods described herein, which are intended as illustrations of a few aspects of the claims and any apparatus, systems, and methods that are functionally equivalent are intended to fall within the scope of the claims. Various modifications of the apparatus, systems, and methods in addition to those shown and described herein are intended to fall within the scope of the appended claims. Further, while only certain representative apparatus and system materials and method steps disclosed herein are specifically described, other combinations of the apparatus and system materials and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed.

That which is claimed:

1. An artificial fingernail comprising:
    a housing having an arcuate cross section and comprising an internal volume comprising an upper arcuate surface spaced apart from a lower arcuate surface by a thickness, such that the internal volume comprises a substantially arcuate cross-section;
    a detection layer comprising a lateral flow assay and disposed within the internal volume, wherein the detection layer comprises upper and lower surfaces having substantially the same arcuate curvature as the upper and lower arcuate surfaces of the internal volume, wherein the detection layer further comprises substantially the same thickness as the internal volume;
    a sample port positioned on the housing to permit fluid communication between a fluid external to the housing and the lateral flow assay; and
    an absorbent pad comprising first and second ends and a middle region between the first and second ends, wherein the middle region is in fluid communication with the lateral flow assay,
    wherein the lateral flow assay comprises a first longitudinal axis from a first end to a second end of the lateral flow assay that defines a first flow direction,
    wherein the absorbent pad comprises a second longitudinal axis from a first point in the middle region to the second end of the absorbent pad, wherein the second longitudinal axis defines a second flow direction, and
    wherein the first flow direction is substantially opposite the second flow direction.

2. The artificial fingernail of claim 1, further comprising a removable layer coupled to a top surface of the housing over the sample port.

3. The artificial fingernail of claim 1, wherein the lateral flow assay comprises a marker comprising a compound reactive with a targeted substance.

4. The artificial fingernail of claim 1, wherein the lateral flow assay comprises a marker comprising at least one of carboxyfluorescein, 2,7-dichlorofluorescein, Eosin B, Eosin Y, erythrosine, fluorescein, fluorescein amidite, fluorescein isocyanate, gold nanoparticles, aptamers, antibodies, merbromin, phloxine B, Rose Bengal, derivatives or salts thereof, or a combination thereof.

5. The artificial fingernail of claim 1, wherein the sample port is sized to limit a volume of fluid to the detection layer so the lateral flow assay can detect the presence of a targeted substance in a liquid after the artificial fingernail is fully submerged in the liquid.

6. The artificial fingernail of claim 1, wherein the housing further comprises a vent sized to allow a gas to escape the housing when the artificial fingernail is fully submerged in the liquid.

7. The artificial fingernail of claim 1, wherein the lateral flow assay comprises a chromatographic membrane pad comprising a marker, and the marker comprises a compound reactive with any one of: amine-containing compound, benzodiazepine, narcotic, alcohol, date rape drug, pesticide, steroid, steroid metabolite, bacteria, pathogen, fungus, poison, toxin, explosive, explosive precursor material, metal, protein, and sugars.

8. A method of detecting the presence of a targeted substance in a liquid medium, said method comprising:
    providing the artificial fingernail of claim 1;
    submerging at least a portion of the artificial fingernail in the liquid medium; and
    observing an indication to determine presence or absence of the targeted substance.

9. The method of claim 8, wherein the indication comprises any one of: an appearance of a colored dot or region, an absence of any appearance of a colored region, a completion of a pattern, a completion of a line, a completion of a logo, a completion of a symbol, a printing of a word, an appearance of a checkmark, an appearance of an emoticon, an appearance of a symbol, fluorescence, vibration, or sound.

10. The method of claim 8, wherein the indication is made by any one of: electrochemical detection, polymerization or de-polymerization in the presence of an analyte, endothermic reaction, exothermic reaction initiation, hydrogel formation, or electronic device-aided quantitation.

11. The method of claim 8, wherein submerging at least a portion of the artificial fingernail comprises submerging at least a portion of the artificial fingernail in any of: beer, cider, energy drink, flavored drink, fruit drink, liquor, alcoholic beverage, milk, milk-containing beverage, soda, sports drink, vegetable drink, water, wine, blood, non-potable water, organic solvent, potable water, serum, treated waste water, untreated waste water, urine, vomit, or a combination thereof.

12. The method of claim 8, wherein submerging at least a portion of the artificial fingernail comprises fully submerging the artificial fingernail in the liquid medium.

13. The method of claim 8, wherein the artificial fingernail substantially prevents the migration of an assay component into the liquid medium.

14. The artificial fingernail of claim 1, wherein the housing further comprises an internal substantially liquid-proof boundary surrounding the detection layer.

15. The artificial fingernail of claim 1, wherein the artificial fingernail further comprises an adhesive coupled to a bottom surface of the housing.

16. The artificial fingernail of claim 1, wherein a distance within the housing along one or more longitudinal axes of the detection layer starts at the sample port, extends through the lateral flow assay from the first end to the second end, extends through the absorbent pad from the middle region to the second end, and ends at the second end of the absorbent pad, wherein the distance is greater than any external dimension of the housing.

17. The artificial fingernail of claim 1, wherein the lateral flow assay comprises a substantially arcuate lateral cross-section and a substantially arcuate longitudinal cross-section.

* * * * *